(12) United States Patent
Braisted et al.

(10) Patent No.: US 6,197,927 B1
(45) Date of Patent: *Mar. 6, 2001

(54) PEPTIDE VARIANTS OF PROTEIN A

(75) Inventors: Andrew C. Braisted, San Francisco; Melissa A. Starovasnik; James A. Wells, both of Burlingame, all of CA (US)

(73) Assignee: Genentech Inc., So. San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/036,549

(22) Filed: Mar. 6, 1998

Related U.S. Application Data

(63) Continuation of application No. 08/657,983, filed on Jun. 4, 1996, now Pat. No. 6,013,763.

(51) Int. Cl.[7] ...................................................... C07K 5/12
(52) U.S. Cl. .......................... 530/317; 530/324; 530/350; 514/11; 514/12; 424/192.11; 424/193.1; 424/194.1
(58) Field of Search .................................... 530/317, 324, 530/350; 514/11, 12; 424/192.1, 193.1, 194.1

(56) References Cited

PUBLICATIONS

Rudinger, J 'Characteristics of amino acids as components of peptide hormones sequence' in Peptide Hormones, (ed. J.A. Parsons). University Park Press, Baltimore, pp. 1–7, 1976.*

Braisted et al., 'Minimizing a Binding Domain From Protein A', Proc. Nat. Acad. Sci. 93:5688–5692, Jun. 1996.*

Bottomley et al., "Elution of human IgG from affinity columns containing immobilised variants of protein A" Journal of Immunological Methods 182:185–192 (1995).

Bottomley et al., "The stability and unfolding of an IgG binding protein based upon the B domain of protein A from Staphylococcus aureus probed by tryptophan substitution and fluorescence spectroscopy" Protein Eng. 7(12):1463–1470 (1994).

Braisted & Wells, "Evolution of a Reduced Binding Epitope" 96th General Meeting of the Amer. Society for Microbiology (Presentation summary) (May 22, 1996).

Braisted et al., "Minimizing a binding domain from protein A" Proc. Natl. Acad. Sci. 93:5688–5692 (Jun. 11, 1996).

Braisted, A., "Evolution of a Reduced Binding Epitope" IBC Conference of Applied Molecular Evolution (Presentation summary) (Dec. 7, 1995).

Cedergren et al., "Mutational analysis of the interaction between staphylococcal protein A and human IgG$_1$" Protein Engineering 6 (4):441–448 (1993).

Diesenhofer, "Crystallographic Refinement and Atomic Models of a Human Fc Fragment and Its Complex with Fragment B of Protein A from Staphylococcus aureus at 2.9–and 2.8–Angstroms Resolution" Biochemistry 20 (9):2361–2370 (1981).

Djojonegoro et al., "Bacteriophage Surface Display of an Immunoglobulin–binding Domain of Staphylococcus aureus Protein A" Bio/Technology 12:169–172 (1994).

Gouda et al., "Three–Dimensional Solution Structure of the B Domain of Staphylococcal Protein A: Comparisons of the Solution and Crystal Structures" Biochemistry 31:9665–9672 (1992).

Hillson et al., "The Structural Basis of Germline–encoded $V_H3$ Immunoglobulin–Binding to Staphylococcal Protein A" Journal of Experimental Medicine 178:331–336 (1993).

Hjelm et al., "Protein A from Staphylococcus aureus. Its isolation by affinity chromatography and its use as an immunosorbent for isolation of immunoglubulins" FEBS Letters 28 (1):73–76 (1972).

Huston et al., "Multisite association by recombinant proteins can enhance binding selectivity" Biophysical Journal 62:87–91 (1992).

Langone, "Protein A of Staphylococcus aureus and Related Immunoglobulin Receptors Produced by Streptococci and Pneumonococci" Advances in Immunology 32:157–252 (1982).

Lofdahl et al., "Gene for staphylococcal protein A" Proc. Natl. Acad. Sci. (USA) 80:697–701 (1983).

Nilsson et al., "A synthetic IgG–binding domain based on staphylococcal protein A" Protein Eng. 1:107–113 (1987).

Nord et al., "A combinational library of an alpha–helical bacterial receptor domain" Protein Engineering 8 (6):601–608 (1995).

Popplewell et al., "Synthesis and mutagenesis of an IgG–binding protein based upon protein A of Staphylococcus aureus" Protein Engineering 4(8):963–970 (1991).

Sasso et al., "Human IgA and IgG F(ab')$_2$ that bind to staphylococcal protein A belong to the $V_H$III Subgroup" J. Immunol. 147(6):1877–1883 (1991).

(List continued on next page.)

Primary Examiner—Michael P. Woodward
Assistant Examiner—Anish Gupta
(74) Attorney, Agent, or Firm—Richard B. Love

(57) ABSTRACT

Z domain variants of staphylococcal protein A have significantly reduced size but possess IgG-binding affinity equivalent to the wild type Z domain. These Z domain variants are suitable for use in affinity chromatography purification of proteins and in the treatment of staphylococcic diseases.

8 Claims, 6 Drawing Sheets

(5 of 6 Drawing Sheet(s) Filed in Color)

PUBLICATIONS

Sisson and Castor, "An improved method for immobilizing IgG antibodies on protein A–agarose" *Journal of Immunological Methods* 127:215–220 (1990).

Torigoe et al., "Sequential $^1$H NMR Assignments and Secondary Structure of the B Domain of Staphylococcal Protein A: Structural Changes between the Free B Domain in Solution and the Fc–Bound B Domain in Crystal" *Biochemistry* 29:8787–8793 (1990).

Uhlen and Moks, "Gene Fusions for Purpose of Expression: An Introduction" *Methods in Enzymology* 185:129–161 (1990).

Uhlen et al., "Complete Sequence of the Staphylococcal Gene Encoding A, A Gene Evolved Through Multiple Duplications" *Journal of Biological Chemistry* 259(3) : 1695–1702 (1984).

* cited by examiner

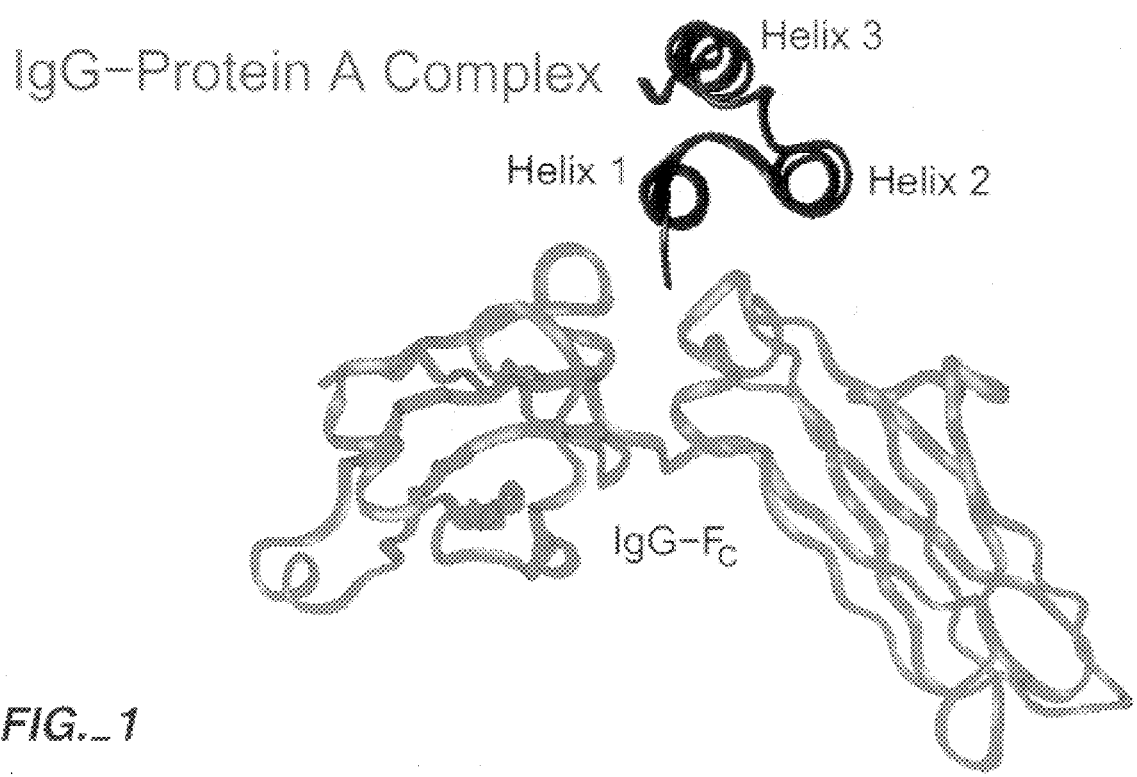
FIG._1

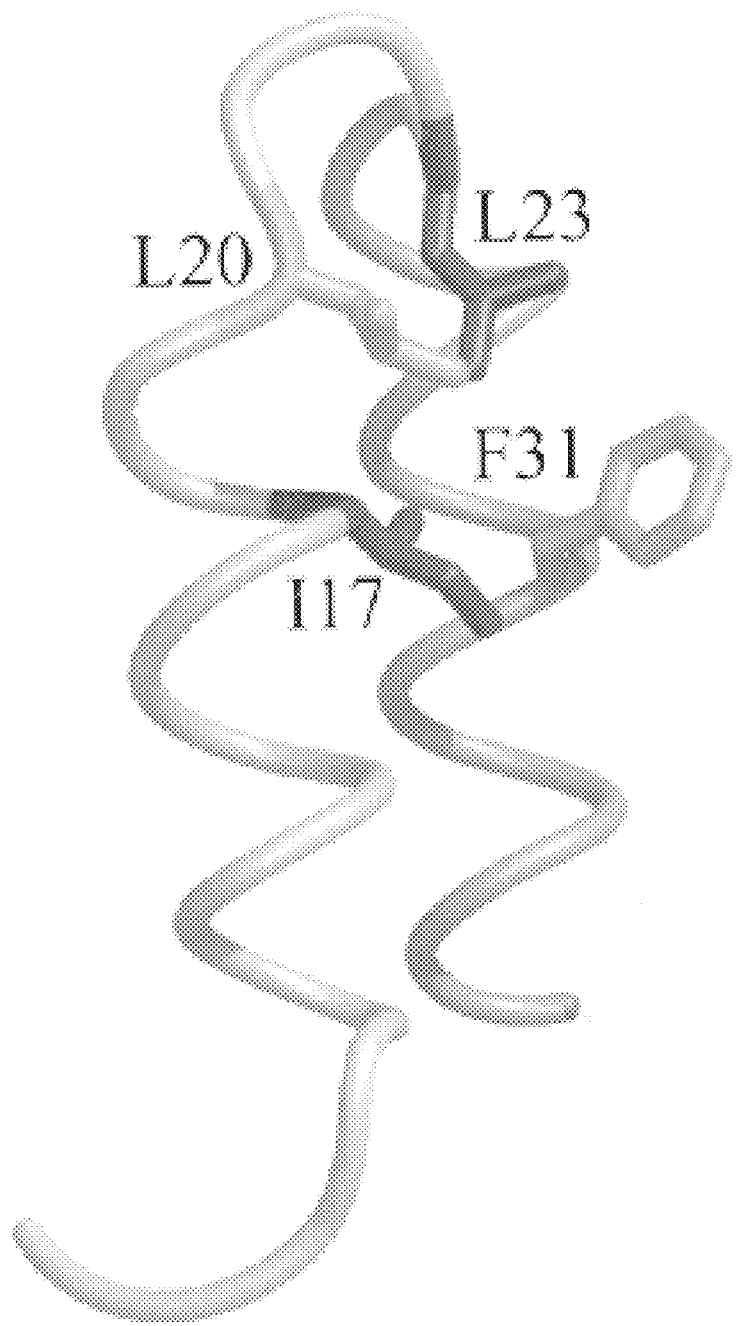
FIG._2A

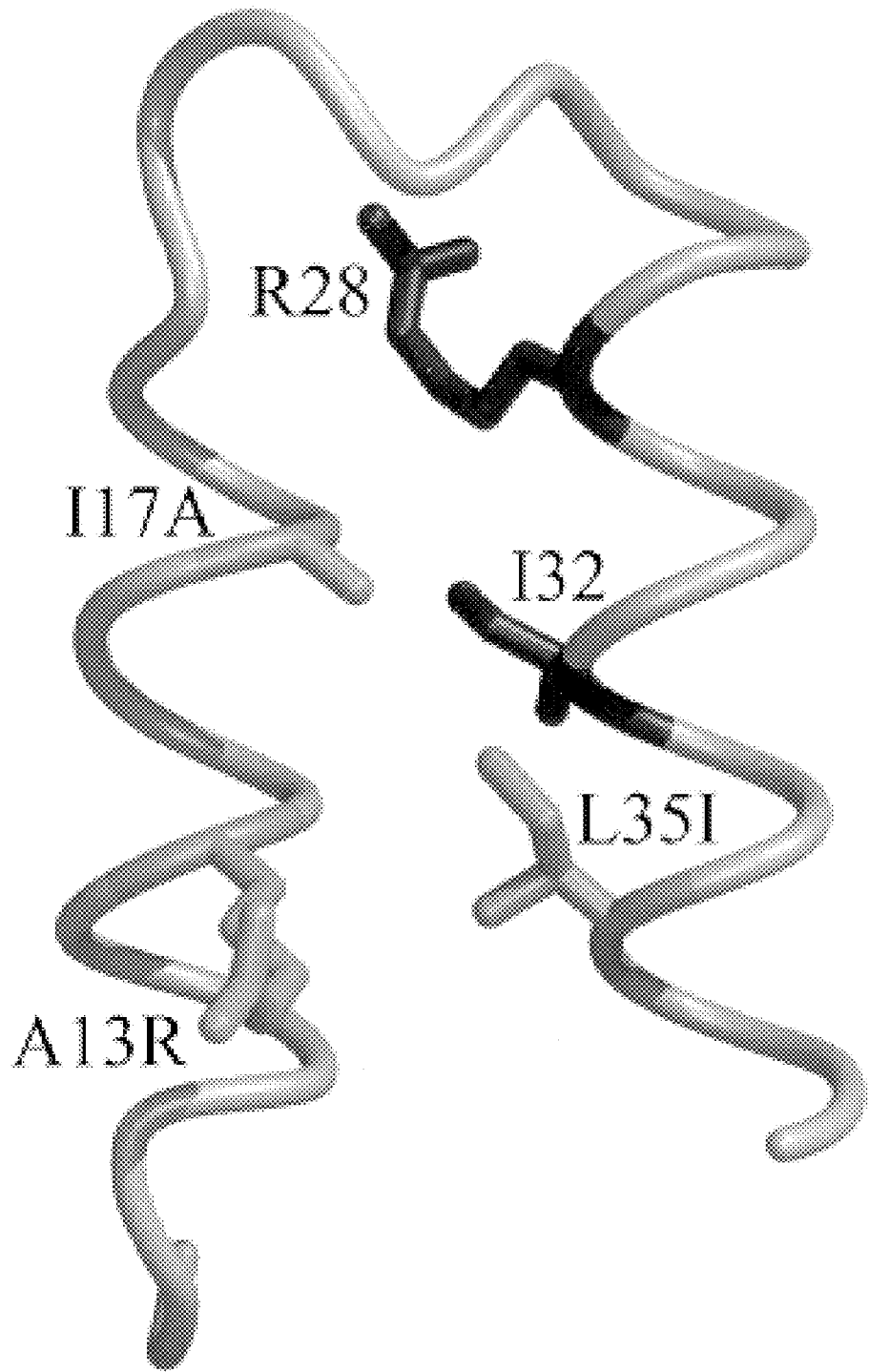
FIG._2B

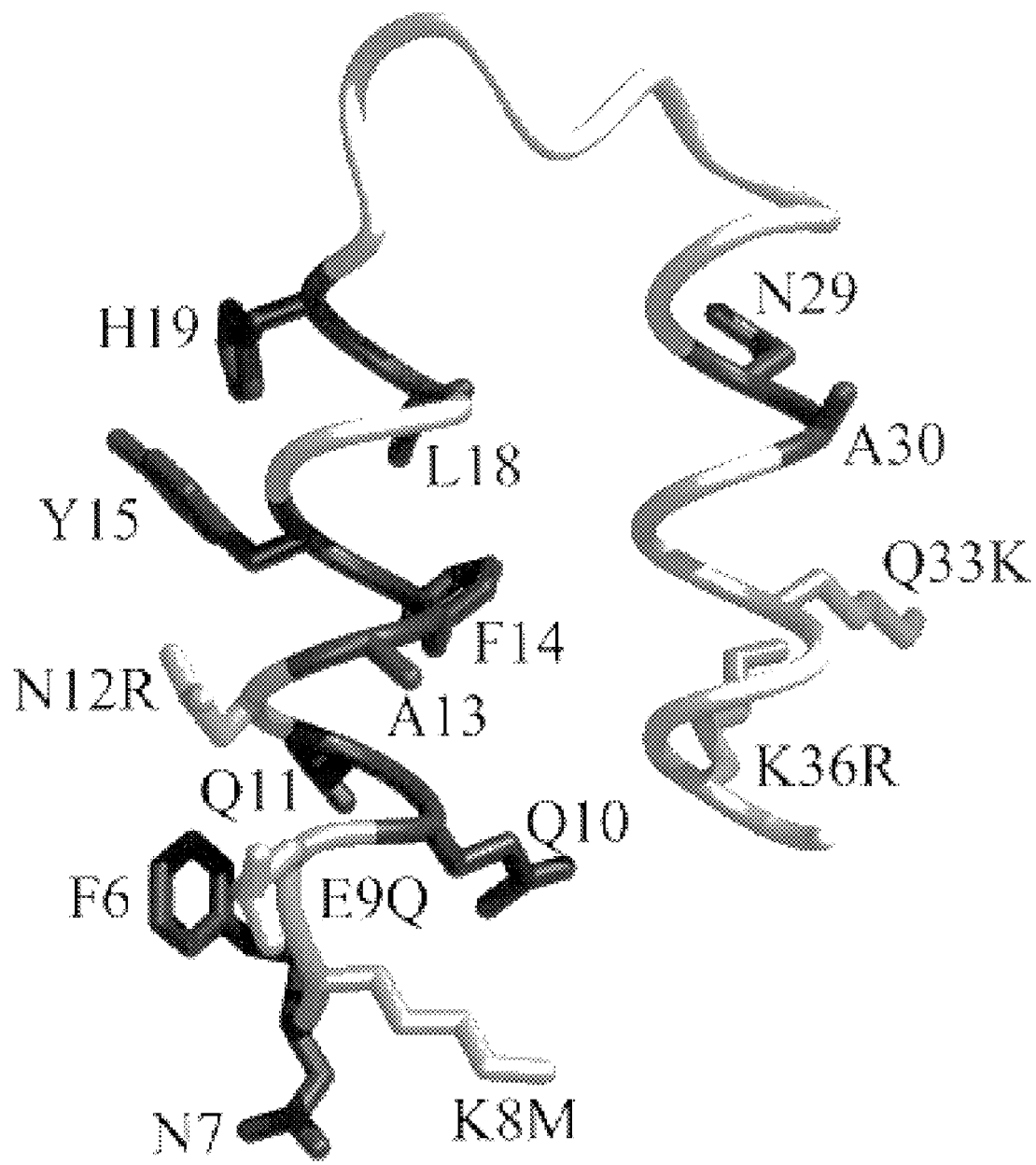
FIG._2C

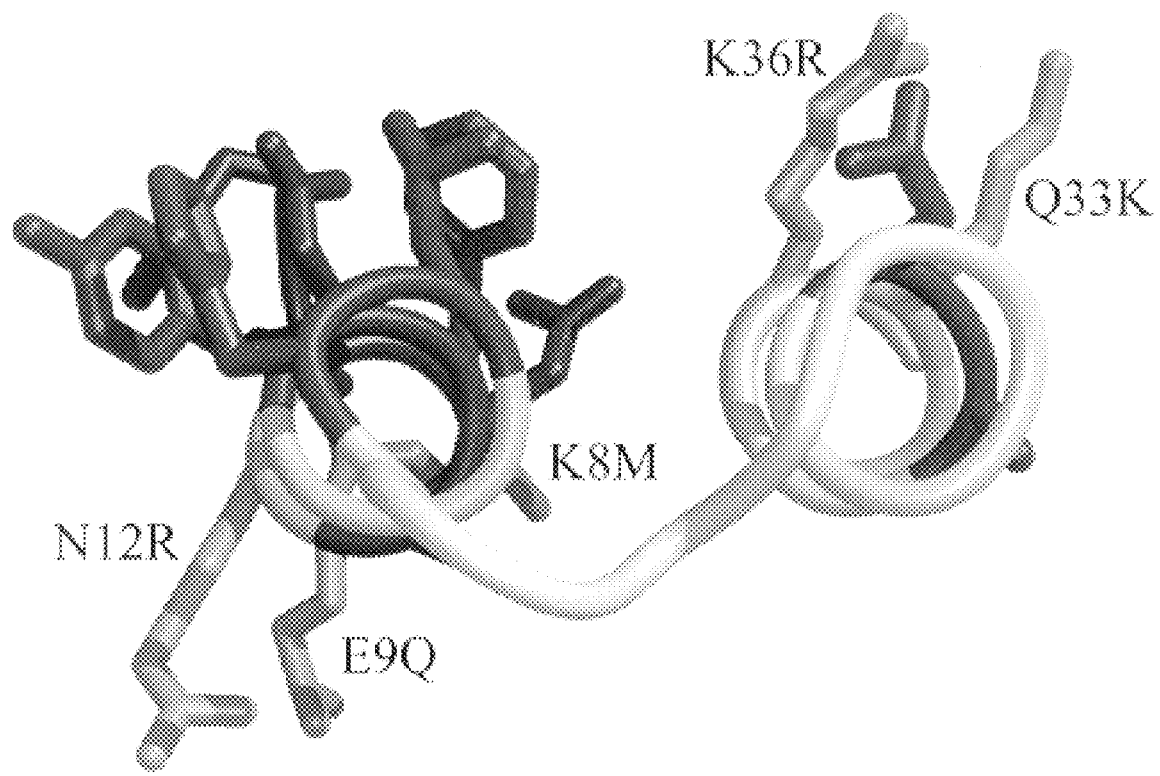
FIG._2D

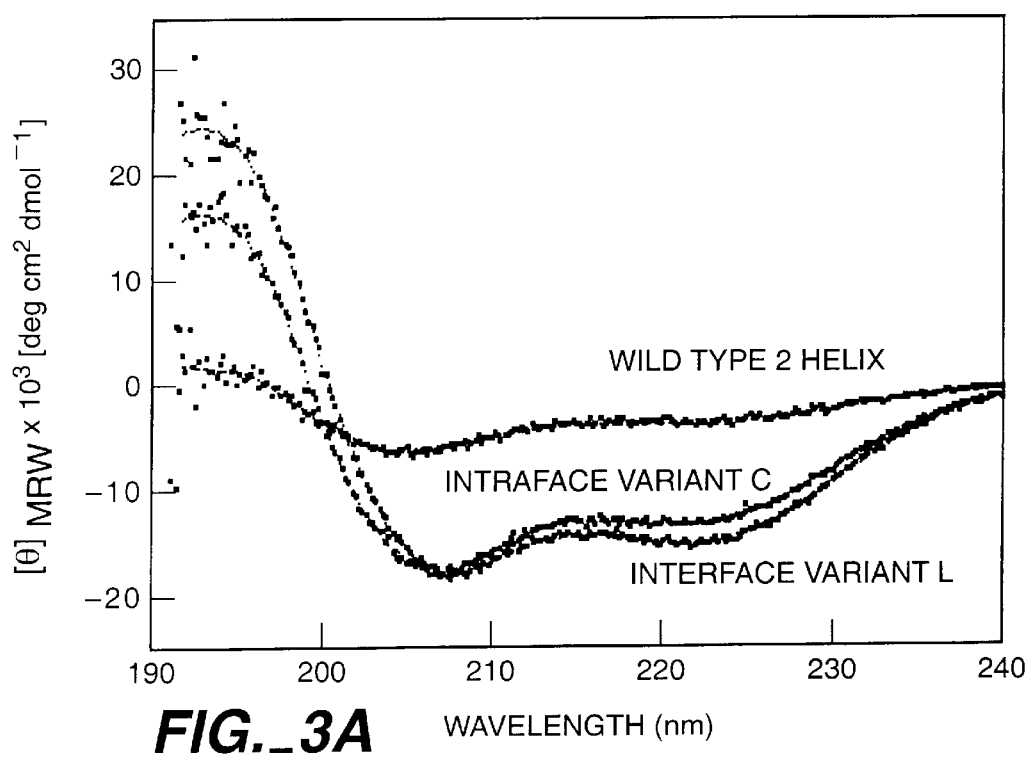
FIG._3A
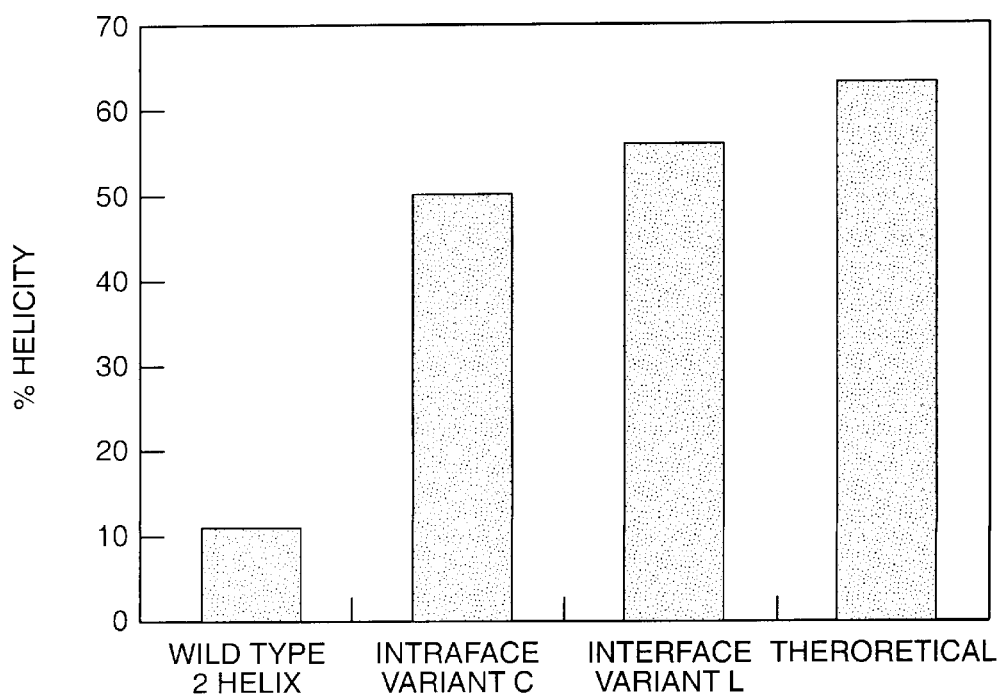
FIG._3B

SEQUENCE LISTING (1) GENERAL INFORMATION:

(iii) NUMBER OF SEQUENCES: 47

(2) INFORMATION FOR SEQ ID NO:1:

(i) SEQUENCE CHARACTERISTICS:
      (A) LENGTH: 33 amino acids
      (B) TYPE: Amino Acid
      (D) TOPOLOGY: Linear (xi) SEQUENCE DESCRIPTION: SEQ ID NO:1:

```
Xaa Xaa Xaa Xaa Gln Gln Xaa Xaa Phe Tyr Glu Ala Leu His Asp
 1               5                  10                  15

Pro Asn Leu Asn Glu Glu Gln Arg Asn Ala Lys Ile Xaa Ser Ile
                20                  25                  30

Xaa Asp Asp
        33
```

(2) INFORMATION FOR SEQ ID NO:2:

(i) SEQUENCE CHARACTERISTICS:
      (A) LENGTH: 5 amino acids
      (B) TYPE: Amino Acid
      (D) TOPOLOGY: Linear (xi) SEQUENCE DESCRIPTION: SEQ ID NO:2:

```
Ala Val Xaa Xaa Xaa
 1               5
```

(2) INFORMATION FOR SEQ ID NO:3:

(i) SEQUENCE CHARACTERISTICS:
      (A) LENGTH: 34 amino acids
      (B) TYPE: Amino Acid
      (D) TOPOLOGY: Linear (xi) SEQUENCE DESCRIPTION: SEQ ID NO:3:

```
Xaa Xaa Xaa Xaa Cys Gln Xaa Xaa Phe Tyr Glu Ala Leu His Asp
 1               5                  10                  15

Pro Asn Leu Asn Glu Glu Gln Arg Asn Ala Lys Ile Xaa Ser Ile
                20                  25                  30

Xaa Asp Asp Cys
            34
```

(2) INFORMATION FOR SEQ ID NO:4:

(i) SEQUENCE CHARACTERISTICS:
      (A) LENGTH: 59 amino acids
      (B) TYPE: Amino Acid
      (D) TOPOLOGY: Linear (xi) SEQUENCE DESCRIPTION: SEQ ID NO:4:

```
Ala Val Asp Asn Lys Phe Asn Lys Glu Gln Gln Asn Ala Phe Tyr
 1               5                  10                  15

Glu Ile Leu His Leu Pro Asn Leu Asn Glu Glu Gln Arg Asn Ala
```

```
                     20                  25                  30

Phe Ile Gln Ser Leu Lys Asp Asp Pro Ser Gln Ser Ala Asn Leu
                 35                  40                  45

Leu Ala Glu Ala Lys Lys Leu Asn Asp Ala Gln Ala Pro Lys
                 50                  55              59
```

(2) INFORMATION FOR SEQ ID NO:5:

(i) SEQUENCE CHARACTERISTICS:
        (A) LENGTH: 38 amino acids
        (B) TYPE: Amino Acid
        (D) TOPOLOGY: Linear (xi) SEQUENCE DESCRIPTION: SEQ ID NO:5:

```
Ala Val Asp Asn Lys Phe Asn Lys Glu Gln Gln Asn Arg Phe Tyr
 1               5                  10                  15

Glu Ala Leu His Asp Pro Asn Leu Asn Glu Glu Gln Arg Asn Ala
                 20                  25                  30

Lys Ile Gln Ser Ile Lys Asp Asp
                 35          38
```

(2) INFORMATION FOR SEQ ID NO:6:

(i) SEQUENCE CHARACTERISTICS:
        (A) LENGTH: 38 amino acids
        (B) TYPE: Amino Acid
        (D) TOPOLOGY: Linear (xi) SEQUENCE DESCRIPTION: SEQ ID NO:6:

```
Ala Val Arg Asn Gly Phe Asn Lys Glu Gln Gln Asn Arg Phe Tyr
 1               5                  10                  15

Glu Ala Leu His Asp Pro Asn Leu Asn Glu Glu Gln Arg Asn Ala
                 20                  25                  30

Lys Ile Gln Ser Ile Lys Asp Asp
                 35          38
```

(2) INFORMATION FOR SEQ ID NO:7:

(i) SEQUENCE CHARACTERISTICS:
        (A) LENGTH: 38 amino acids
        (B) TYPE: Amino Acid
        (D) TOPOLOGY: Linear (xi) SEQUENCE DESCRIPTION: SEQ ID NO:7:

```
Ala Val Ala Gln Ser Phe Asn Lys Glu Gln Gln Asn Arg Phe Tyr
 1               5                  10                  15

Glu Ala Leu His Asp Pro Asn Leu Asn Glu Glu Gln Arg Asn Ala
                 20                  25                  30

Lys Ile Gln Ser Ile Lys Asp Asp
                 35          38
```

(2) INFORMATION FOR SEQ ID NO:8:

(i) SEQUENCE CHARACTERISTICS:
        (A) LENGTH: 38 amino acids
        (B) TYPE: Amino Acid
        (D) TOPOLOGY: Linear (xi) SEQUENCE DESCRIPTION: SEQ ID NO:8:

```
Ala Val Asp Asn Lys Phe Asn Met Gln Gln Asn Arg Phe Tyr
 1               5                  10                  15

Glu Ala Leu His Asp Pro Asn Leu Asn Glu Glu Gln Arg Asn Ala
```

20                  25                  30

Lys Ile Gln Ser Ile Lys Asp Asp
                35          38

(2) INFORMATION FOR SEQ ID NO:9:

(i) SEQUENCE CHARACTERISTICS:
        (A) LENGTH: 38 amino acids
        (B) TYPE: Amino Acid
        (D) TOPOLOGY: Linear (xi) SEQUENCE DESCRIPTION: SEQ ID NO:9:

Ala Val Asp Asn Lys Gly Trp Met Arg Gln Gln Asn Arg Phe Tyr
 1               5                  10                  15

Glu Ala Leu His Asp Pro Asn Leu Asn Glu Glu Gln Arg Asn Ala
                20                  25                  30

Lys Ile Gln Ser Ile Lys Asp Asp
                35          38

(2) INFORMATION FOR SEQ ID NO:10:

(i) SEQUENCE CHARACTERISTICS:
        (A) LENGTH: 38 amino acids
        (B) TYPE: Amino Acid
        (D) TOPOLOGY: Linear (xi) SEQUENCE DESCRIPTION: SEQ ID NO:10:

Ala Val Asp Asn Lys Phe Asn Lys Glu Gln Gln Arg Arg Phe Tyr
 1               5                  10                  15

Glu Ala Leu His Asp Pro Asn Leu Asn Glu Glu Gln Arg Asn Ala
                20                  25                  30

Lys Ile Gln Ser Ile Lys Asp Asp
                35          38

(2) INFORMATION FOR SEQ ID NO:11:

(i) SEQUENCE CHARACTERISTICS:
        (A) LENGTH: 38 amino acids
        (B) TYPE: Amino Acid
        (D) TOPOLOGY: Linear (xi) SEQUENCE DESCRIPTION: SEQ ID NO:11:

Ala Val Asp Asn Lys Phe Asn Lys Glu Gln Gln Arg Ala Phe Tyr
 1               5                  10                  15

Glu Ala Leu His Asp Pro Asn Leu Asn Glu Glu Gln Arg Asn Ala
                20                  25                  30

Lys Ile Gln Ser Ile Lys Asp Asp
                35          38

(2) INFORMATION FOR SEQ ID NO:12:

(i) SEQUENCE CHARACTERISTICS:
        (A) LENGTH: 38 amino acids
        (B) TYPE: Amino Acid
        (D) TOPOLOGY: Linear (xi) SEQUENCE DESCRIPTION: SEQ ID NO:12:

Ala Val Asp Asn Lys Phe Asn Lys Glu Gln Gln Asn Arg Phe Tyr
 1               5                  10                  15

Glu Ala Leu His Asp Pro Asn Leu Asn Glu Glu Gln Arg Asn Ala
                20                  25                  30

Lys Ile Lys Ser Ile Arg Asp Asp (2) INFORMATION FOR SEQ ID NO:13:

(i) SEQUENCE CHARACTERISTICS:
        (A) LENGTH: 38 amino acids
        (B) TYPE: Amino Acid
        (D) TOPOLOGY: Linear (xi) SEQUENCE DESCRIPTION: SEQ ID NO:13:

```
Ala Val Arg Asn Gly Phe Asn Met Gln Gln Gln Arg Arg Phe Tyr
 1               5                  10                  15

Glu Ala Leu His Asp Pro Asn Leu Asn Glu Glu Gln Arg Asn Ala
                20                  25                  30

Lys Ile Lys Ser Ile Arg Asp Asp
                35          38
```

(2) INFORMATION FOR SEQ ID NO:14:

(i) SEQUENCE CHARACTERISTICS:
        (A) LENGTH: 38 amino acids
        (B) TYPE: Amino Acid
        (D) TOPOLOGY: Linear (xi) SEQUENCE DESCRIPTION: SEQ ID NO:14:

```
Ala Val Ala Gln Ser Phe Asn Met Gln Gln Gln Arg Arg Phe Tyr
 1               5                  10                  15

Glu Ala Leu His Asp Pro Asn Leu Asn Glu Glu Gln Arg Asn Ala
                20                  25                  30

Lys Ile Lys Ser Ile Arg Asp Asp
                35          38
```

(2) INFORMATION FOR SEQ ID NO:15:

(i) SEQUENCE CHARACTERISTICS:
        (A) LENGTH: 33 amino acids
        (B) TYPE: Amino Acid
        (D) TOPOLOGY: Linear (xi) SEQUENCE DESCRIPTION: SEQ ID NO:15:

```
Phe Asn Met Gln Gln Gln Arg Arg Phe Tyr Glu Ala Leu His Asp
 1               5                  10                  15

Pro Asn Leu Asn Glu Glu Gln Arg Asn Ala Lys Ile Lys Ser Ile
                20                  25                  30

Arg Asp Asp
        33
```

(2) INFORMATION FOR SEQ ID NO:16:

(i) SEQUENCE CHARACTERISTICS:
        (A) LENGTH: 38 amino acids
        (B) TYPE: Amino Acid
        (D) TOPOLOGY: Linear (xi) SEQUENCE DESCRIPTION: SEQ ID NO:16:

```
Ala Val Asp Asn Lys Phe Asn Lys Glu Gln Gln Ala Arg Phe Tyr
 1               5                  10                  15

Glu Ala Leu His Asp Pro Asn Leu Asn Glu Glu Gln Arg Asn Ala
                20                  25                  30

Lys Ile Gln Ser Ile Lys Asp Asp
                35          38
```

(2) INFORMATION FOR SEQ ID NO:17:

(i) SEQUENCE CHARACTERISTICS:
        (A) LENGTH: 38 amino acids
        (B) TYPE: Amino Acid
        (D) TOPOLOGY: Linear (xi) SEQUENCE DESCRIPTION: SEQ ID NO:17:

Ala Val Arg Asn Gly Phe Asn Lys Glu Gln Gln Ala Arg Phe Tyr
 1               5                  10                  15

Glu Ala Leu His Asp Pro Asn Leu Asn Glu Glu Gln Arg Asn Ala
                20                  25                  30

Lys Ile Gln Ser Ile Lys Asp Asp
                35          38

(2) INFORMATION FOR SEQ ID NO:18:

(i) SEQUENCE CHARACTERISTICS:
        (A) LENGTH: 38 amino acids
        (B) TYPE: Amino Acid
        (D) TOPOLOGY: Linear (xi) SEQUENCE DESCRIPTION: SEQ ID NO:18:

Ala Val Ala Gln Ser Phe Asn Lys Glu Gln Gln Ala Arg Phe Tyr
 1               5                  10                  15

Glu Ala Leu His Asp Pro Asn Leu Asn Glu Glu Gln Arg Asn Ala
                20                  25                  30

Lys Ile Gln Ser Ile Lys Asp Asp
                35          38

(2) INFORMATION FOR SEQ ID NO:19:

(i) SEQUENCE CHARACTERISTICS:
        (A) LENGTH: 38 amino acids
        (B) TYPE: Amino Acid
        (D) TOPOLOGY: Linear (xi) SEQUENCE DESCRIPTION: SEQ ID NO:19:

Ala Val Asp Asn Lys Phe Asn Met Gln Gln Ala Arg Phe Tyr
 1               5                  10                  15

Glu Ala Leu His Asp Pro Asn Leu Asn Glu Glu Gln Arg Asn Ala
                20                  25                  30

Lys Ile Gln Ser Ile Lys Asp Asp
                35          38

(2) INFORMATION FOR SEQ ID NO:20:

(i) SEQUENCE CHARACTERISTICS:
        (A) LENGTH: 38 amino acids
        (B) TYPE: Amino Acid
        (D) TOPOLOGY: Linear (xi) SEQUENCE DESCRIPTION: SEQ ID NO:20:

Ala Val Asp Asn Lys Gly Trp Met Arg Gln Gln Ala Arg Phe Tyr
 1               5                  10                  15

Glu Ala Leu His Asp Pro Asn Leu Asn Glu Glu Gln Arg Asn Ala
                20                  25                  30

Lys Ile Gln Ser Ile Lys Asp Asp
                35          38

(2) INFORMATION FOR SEQ ID NO:21:

(i) SEQUENCE CHARACTERISTICS:

(A) LENGTH: 38 amino acids
        (B) TYPE: Amino Acid
        (D) TOPOLOGY: Linear (xi) SEQUENCE DESCRIPTION: SEQ ID NO:21:

Ala Val Asp Asn Lys Phe Asn Lys Glu Gln Gln Ala Ala Phe Tyr
1               5                   10                  15

Glu Ala Leu His Asp Pro Asn Leu Asn Glu Gly Gln Arg Asn Ala
            20                  25                  30

Lys Ile Gln Ser Ile Lys Asp Asp
            35          38

(2) INFORMATION FOR SEQ ID NO:22:

(i) SEQUENCE CHARACTERISTICS:
        (A) LENGTH: 38 amino acids
        (B) TYPE: Amino Acid
        (D) TOPOLOGY: Linear (xi) SEQUENCE DESCRIPTION: SEQ ID NO:22:

Ala Val Asp Asn Lys Phe Asn Lys Glu Gln Gln Ala Arg Phe Tyr
1               5                   10                  15

Glu Ala Leu His Asp Pro Asn Leu Asn Glu Glu Gln Arg Asn Ala
            20                  25                  30

Lys Ile Lys Ser Ile Arg Asp Asp
            35          38

(2) INFORMATION FOR SEQ ID NO:23:

(i) SEQUENCE CHARACTERISTICS:
        (A) LENGTH: 38 amino acids
        (B) TYPE: Amino Acid
        (D) TOPOLOGY: Linear (xi) SEQUENCE DESCRIPTION: SEQ ID NO:23:

Ala Val Arg Asn Gly Phe Asn Met Gln Gln Gln Ala Arg Phe Tyr
1               5                   10                  15

Glu Ala Leu His Asp Pro Asn Leu Asn Glu Gly Gln Arg Asn Ala
            20                  25                  30

Lys Ile Lys Ser Ile Arg Asp Asp
            35          38

(2) INFORMATION FOR SEQ ID NO:24:

(i) SEQUENCE CHARACTERISTICS:
        (A) LENGTH: 38 amino acids
        (B) TYPE: Amino Acid
        (D) TOPOLOGY: Linear (xi) SEQUENCE DESCRIPTION: SEQ ID NO:24:

Ala Val Ala Gln Ser Phe Asn Met Gln Gln Gln Ala Arg Phe Tyr
1               5                   10                  15

Glu Ala Leu His Asp Pro Asn Leu Asn Glu Glu Gln Arg Asn Ala
            20                  25                  30

Lys Ile Lys Ser Ile Arg Asp Asp
            35          38

(2) INFORMATION FOR SEQ ID NO:25:

(i) SEQUENCE CHARACTERISTICS:
        (A) LENGTH: 33 amino acids
        (B) TYPE: Amino Acid
        (D) TOPOLOGY: Linear (xi) SEQUENCE DESCRIPTION: SEQ ID NO:25:

Phe Asn Met Gln Gln Gln Ala Arg Phe Tyr Glu Ala Leu His Asp
 1               5                  10                  15

Pro Asn Leu Asn Glu Glu Gln Arg Asn Ala Lys Ile Lys Ser Ile
                20                  25                  30

Arg Asp Asp
        33

(2) INFORMATION FOR SEQ ID NO:26:

(i) SEQUENCE CHARACTERISTICS:
        (A) LENGTH: 39 amino acids
        (B) TYPE: Amino Acid
        (D) TOPOLOGY: Linear (xi) SEQUENCE DESCRIPTION: SEQ ID NO:26:

Ala Val Asp Asn Lys Phe Asn Lys Glu Cys Gln Asn Arg Phe Tyr
 1               5                  10                  15

Glu Ala Leu His Asp Pro Asn Leu Asn Glu Glu Gln Arg Asn Ala
                20                  25                  30

Lys Ile Gln Ser Ile Lys Asp Asp Cys
                35                  39

(2) INFORMATION FOR SEQ ID NO:27:

(i) SEQUENCE CHARACTERISTICS:
        (A) LENGTH: 39 amino acids
        (B) TYPE: Amino Acid
        (D) TOPOLOGY: Linear (xi) SEQUENCE DESCRIPTION: SEQ ID NO:27:

Ala Val Arg Asn Gly Phe Asn Lys Glu Cys Gln Asn Arg Phe Tyr
 1               5                  10                  15

Glu Ala Leu His Asp Pro Asn Leu Asn Glu Glu Gln Arg Asn Ala
                20                  25                  30

Lys Ile Gln Ser Ile Lys Asp Asp Cys
                35                  39

(2) INFORMATION FOR SEQ ID NO:28:

(i) SEQUENCE CHARACTERISTICS:
        (A) LENGTH: 39 amino acids
        (B) TYPE: Amino Acid
        (D) TOPOLOGY: Linear (xi) SEQUENCE DESCRIPTION: SEQ ID NO:28:

Ala Val Ala Gln Ser Phe Asn Lys Glu Cys Gln Asn Arg Phe Tyr
 1               5                  10                  15

Glu Ala Leu His Asp Pro Asn Leu Asn Glu Glu Gln Arg Asn Ala
                20                  25                  30

Lys Ile Gln Ser Ile Lys Asp Asp Cys
                35                  39

(2) INFORMATION FOR SEQ ID NO:29:

(i) SEQUENCE CHARACTERISTICS:
        (A) LENGTH: 39 amino acids
        (B) TYPE: Amino Acid
        (D) TOPOLOGY: Linear (xi) SEQUENCE DESCRIPTION: SEQ ID NO:29:

```
Ala Val Asp Asn Lys Phe Asn Met Gln Cys Gln Asn Arg Phe Tyr
 1               5                  10                  15

Glu Ala Leu His Asp Pro Asn Leu Asn Glu Glu Gln Arg Asn Ala
            20                  25                      30

Lys Ile Gln Ser Ile Lys Asp Asp Cys
            35              39
```

(2) INFORMATION FOR SEQ ID NO:30:

(i) SEQUENCE CHARACTERISTICS:
        (A) LENGTH: 39 amino acids
        (B) TYPE: Amino Acid
        (D) TOPOLOGY: Linear (xi) SEQUENCE DESCRIPTION: SEQ ID NO:30:

```
Ala Val Asp Asn Lys Gly Trp Met Arg Cys Gln Asn Arg Phe Tyr
 1               5                  10                  15

Glu Ala Leu His Asp Pro Asn Leu Asn Glu Glu Gln Arg Asn Ala
            20                  25                      30

Lys Ile Gln Ser Ile Lys Asp Asp Cys
            35              39
```

(2) INFORMATION FOR SEQ ID NO:31:

(i) SEQUENCE CHARACTERISTICS:
        (A) LENGTH: 39 amino acids
        (B) TYPE: Amino Acid
        (D) TOPOLOGY: Linear (xi) SEQUENCE DESCRIPTION: SEQ ID NO:31:

```
Ala Val Asp Asn Lys Phe Asn Lys Glu Cys Gln Arg Arg Phe Tyr
 1               5                  10                  15

Glu Ala Leu His Asp Pro Asn Leu Asn Glu Glu Gln Arg Asn Ala
            20                  25                      30

Lys Ile Gln Ser Ile Lys Asp Asp Cys
            35              39
```

(2) INFORMATION FOR SEQ ID NO:32:

(i) SEQUENCE CHARACTERISTICS:
        (A) LENGTH: 39 amino acids
        (B) TYPE: Amino Acid
        (D) TOPOLOGY: Linear (xi) SEQUENCE DESCRIPTION: SEQ ID NO:32:

```
Ala Val Asp Asn Lys Phe Asn Lys Glu Cys Gln Arg Ala Phe Tyr
 1               5                  10                  15

Glu Ala Leu His Asp Pro Asn Leu Asn Glu Glu Gln Arg Asn Ala
            20                  25                      30

Lys Ile Gln Ser Ile Lys Asp Asp Cys
            35              39
```

(2) INFORMATION FOR SEQ ID NO:33:

(i) SEQUENCE CHARACTERISTICS:
        (A) LENGTH: 39 amino acids
        (B) TYPE: Amino Acid
        (D) TOPOLOGY: Linear (xi) SEQUENCE DESCRIPTION: SEQ ID NO:33:

```
Ala Val Asp Asn Lys Phe Asn Lys Glu Cys Gln Asn Arg Phe Tyr
 1               5                  10                  15
```

```
Glu Ala Leu His Asp Pro Asn Leu Asn Glu Glu Gln Arg Asn Ala
                20                  25                  30

Lys Ile Lys Ser Ile Arg Asp Asp Cys
                35              39

(2) INFORMATION FOR SEQ ID NO:34:

(i) SEQUENCE CHARACTERISTICS:
        (A) LENGTH: 39 amino acids
        (B) TYPE: Amino Acid
        (D) TOPOLOGY: Linear (xi) SEQUENCE DESCRIPTION: SEQ ID NO:34:

Ala Val Arg Asn Gly Phe Asn Met Gln Cys Gln Arg Arg Phe Tyr
 1               5                  10                  15

Glu Ala Leu His Asp Pro Asn Leu Asn Glu Glu Gln Arg Asn Ala
                20                  25                  30

Lys Ile Lys Ser Ile Arg Asp Asp Cys
                35              39

(2) INFORMATION FOR SEQ ID NO:35:

(i) SEQUENCE CHARACTERISTICS:
        (A) LENGTH: 39 amino acids
        (B) TYPE: Amino Acid
        (D) TOPOLOGY: Linear (xi) SEQUENCE DESCRIPTION: SEQ ID NO:35:

Ala Val Ala Gln Ser Phe Asn Met Gln Cys Gln Arg Arg Phe Tyr
 1               5                  10                  15

Glu Ala Leu His Asp Pro Asn Leu Asn Glu Glu Gln Arg Asn Ala
                20                  25                  30

Lys Ile Lys Ser Ile Arg Asp Asp Cys
                35              39

(2) INFORMATION FOR SEQ ID NO:36:

(i) SEQUENCE CHARACTERISTICS:
        (A) LENGTH: 34 amino acids
        (B) TYPE: Amino Acid
        (D) TOPOLOGY: Linear (xi) SEQUENCE DESCRIPTION: SEQ ID NO:36:

Phe Asn Met Gln Cys Gln Arg Arg Phe Tyr Glu Ala Leu His Asp
 1               5                  10                  15

Pro Asn Leu Asn Glu Glu Gln Arg Asn Ala Lys Ile Lys Ser Ile
                20                  25                  30

Arg Asp Asp Cys
            34

(2) INFORMATION FOR SEQ ID NO:37:

(i) SEQUENCE CHARACTERISTICS:
        (A) LENGTH: 39 amino acids
        (B) TYPE: Amino Acid
        (D) TOPOLOGY: Linear (xi) SEQUENCE DESCRIPTION: SEQ ID NO:37:

Ala Val Asp Asn Lys Phe Asn Lys Glu Cys Gln Ala Arg Phe Tyr
 1               5                  10                  15

Glu Ala Leu His Asp Pro Asn Leu Asn Glu Glu Gln Arg Asn Ala
                20                  25                  30
```

Lys Ile Gln Ser Ile Lys Asp Asp Cys
                35                  39

(2) INFORMATION FOR SEQ ID NO:38:

(i) SEQUENCE CHARACTERISTICS:
        (A) LENGTH: 39 amino acids
        (B) TYPE: Amino Acid
        (D) TOPOLOGY: Linear (xi) SEQUENCE DESCRIPTION: SEQ ID NO:38:

Ala Val Arg Asn Gly Phe Asn Lys Glu Cys Gln Ala Arg Phe Tyr
1               5                   10                  15

Glu Ala Leu His Asp Pro Asn Leu Asn Glu Glu Gln Arg Asn Ala
                20                  25                  30

Lys Ile Gln Ser Ile Lys Asp Asp Cys
                35                  39

(2) INFORMATION FOR SEQ ID NO:39:

(i) SEQUENCE CHARACTERISTICS:
        (A) LENGTH: 39 amino acids
        (B) TYPE: Amino Acid
        (D) TOPOLOGY: Linear (xi) SEQUENCE DESCRIPTION: SEQ ID NO:39:

Ala Val Ala Gln Ser Phe Asn Lys Glu Cys Gln Ala Arg Phe Tyr
1               5                   10                  15

Glu Ala Leu His Asp Pro Asn Leu Asn Glu Glu Gln Arg Asn Ala
                20                  25                  30

Lys Ile Gln Ser Ile Lys Asp Asp Cys
                35                  39

(2) INFORMATION FOR SEQ ID NO:40:

(i) SEQUENCE CHARACTERISTICS:
        (A) LENGTH: 39 amino acids
        (B) TYPE: Amino Acid
        (D) TOPOLOGY: Linear (xi) SEQUENCE DESCRIPTION: SEQ ID NO:40:

Ala Val Asp Asn Lys Phe Asn Met Gln Cys Gln Ala Arg Phe Tyr
1               5                   10                  15

Glu Ala Leu His Asp Pro Asn Leu Asn Glu Glu Gln Arg Asn Ala
                20                  25                  30

Lys Ile Gln Ser Ile Lys Asp Asp Cys
                35                  39

(2) INFORMATION FOR SEQ ID NO:41:

(i) SEQUENCE CHARACTERISTICS:
        (A) LENGTH: 39 amino acids
        (B) TYPE: Amino Acid
        (D) TOPOLOGY: Linear (xi) SEQUENCE DESCRIPTION: SEQ ID NO:41:

Ala Val Asp Asn Lys Gly Trp Met Arg Cys Gln Ala Arg Phe Tyr
1               5                   10                  15

Glu Ala Leu His Asp Pro Asn Leu Asn Glu Glu Gln Arg Asn Ala
                20                  25                  30

Lys Ile Gln Ser Ile Lys Asp Asp Cys
                35                  39

(2) INFORMATION FOR SEQ ID NO:42:

(i) SEQUENCE CHARACTERISTICS:
        (A) LENGTH: 39 amino acids
        (B) TYPE: Amino Acid
        (D) TOPOLOGY: Linear (xi) SEQUENCE DESCRIPTION: SEQ ID NO:42:

```
Ala Val Asp Asn Lys Phe Asn Lys Glu Cys Gln Ala Ala Phe Tyr
 1               5                  10                  15

Glu Ala Leu His Asp Pro Asn Leu Asn Glu Glu Gln Arg Asn Ala
                20                  25                  30

Lys Ile Gln Ser Ile Lys Asp Asp Cys
                35                  39
```

(2) INFORMATION FOR SEQ ID NO:43:

(i) SEQUENCE CHARACTERISTICS:
        (A) LENGTH: 39 amino acids
        (B) TYPE: Amino Acid
        (D) TOPOLOGY: Linear (xi) SEQUENCE DESCRIPTION: SEQ ID NO:43:

```
Ala Val Asp Asn Lys Phe Asn Lys Glu Cys Gln Ala Arg Phe Tyr
 1               5                  10                  15

Glu Ala Leu His Asp Pro Asn Leu Asn Glu Glu Gln Arg Asn Ala
                20                  25                  30

Lys Ile Lys Ser Ile Arg Asp Asp Cys
                35                  39
```

(2) INFORMATION FOR SEQ ID NO:44:

(i) SEQUENCE CHARACTERISTICS:
        (A) LENGTH: 39 amino acids
        (B) TYPE: Amino Acid
        (D) TOPOLOGY: Linear (xi) SEQUENCE DESCRIPTION: SEQ ID NO:44:

```
Ala Val Arg Asn Gly Phe Asn Met Gln Cys Gln Ala Arg Phe Tyr
 1               5                  10                  15

Glu Ala Leu His Asp Pro Asn Leu Asn Glu Glu Gln Arg Asn Ala
                20                  25                  30

Lys Ile Lys Ser Ile Arg Asp Asp Cys
                35                  39
```

(2) INFORMATION FOR SEQ ID NO:45:

(i) SEQUENCE CHARACTERISTICS:
        (A) LENGTH: 39 amino acids
        (B) TYPE: Amino Acid
        (D) TOPOLOGY: Linear (xi) SEQUENCE DESCRIPTION: SEQ ID NO:45:

```
Ala Val Ala Gln Ser Phe Asn Met Gln Cys Gln Ala Arg Phe Tyr
 1               5                  10                  15

Glu Ala Leu His Asp Pro Asn Leu Asn Glu Glu Gln Arg Asn Ala
                20                  25                  30

Lys Ile Lys Ser Ile Arg Asp Asp Cys
                35                  39
```

(2) INFORMATION FOR SEQ ID NO:46:

(i) SEQUENCE CHARACTERISTICS:
    (A) LENGTH: 34 amino acids
    (B) TYPE: Amino Acid
    (D) TOPOLOGY: Linear (xi) SEQUENCE DESCRIPTION: SEQ ID NO:46:

Phe Asn Met Gln Cys Gln Ala Arg Phe Tyr Glu Ala Leu His Asp
 1               5                  10                  15

Pro Asn Leu Asn Glu Glu Gln Arg Asn Ala Lys Ile Lys Ser Ile
                20                  25                  30

Arg Asp Asp Cys
            34

(2) INFORMATION FOR SEQ ID NO:47:

(i) SEQUENCE CHARACTERISTICS:
        (A) LENGTH: 38 amino acids
        (B) TYPE: Amino Acid
        (D) TOPOLOGY: Linear (xi) SEQUENCE DESCRIPTION: SEQ ID NO:47:

Ala Val Asp Asn Lys Phe Asn Lys Glu Gln Gln Asn Ala Phe Tyr
 1               5                  10                  15

Glu Ile Leu His Leu Pro Asn Leu Asn Glu Glu Gln Arg Asn Ala
                20                  25                  30

Phe Ile Gln Ser Leu Lys Asp Asp
                35          38

PEPTIDE VARIANTS OF PROTEIN A

This application is a continuation application of U.S. Ser. No. 08/657,983 filed Jun. 4, 1996, now U.S. Pat. No. 6,013,763, the entire disclosure of which is incorporated herein by reference.

FIELD OF THE INVENTION

This invention relates to the field of staphylococcal protein A, and more particularly to the gamma-immunoglobulin binding domains of protein A.

BACKGROUND OF THE INVENTION

Protein A from *Staphylococcus aureus* binds with high affinity and high specificity to the Cγ2-Cγ3 interface region of IgG (Langone, *Adv. Immunol.*, 32: 157–252 (1982)). Protein A also exhibits an affinity for the Fab region of immunoglobulins that are encoded by the $V_H$ gene family, $V_H$III (Sasso et al., *J. Immunol,* 61: 3026–3031 (1991); Hillson et al., *A. J Exp. Med.,* 178: 331–336 (1993)). The sequence of the gene coding for protein A revealed two functionally distinct regions (Uhlen et al., *J. Biol. Chem.,* 259: 1695–1702 (1984); Lofdahl et al., *Proc. Natl. Acad Sci (USA),* 80: 697–701 (1983)). The amino-terminal region contains five highly homologous IgG-binding domains (termed E, D, A, B and C), and the carboxy terminal region anchors the protein to the cell wall and membrane. All five IgG-binding domains of protein A bind to IgG via the Fc region.

The structure of the B domain has been studied using $^1$H-NMR (Torigoe et al., *Biochem,* 29: 8787–8793 (1990); Gouda et al., *Biochem.,* 31: 9665–9672 (1992)) and found to consist of three α-helical regions ($α_1$, $α_2$, $α_3$ corresponding to helices I, II and III in the NMR structure) which also are retained when bound to the Fc region of IgG (Gouda, supra). The tri-helical nature of the bound state is in contrast to the X ray crystal structure reported by Deisenhofer, *Biochem.,* 20: 2361–2370 (1981) which showed that $α_1$ and $α_2$ helices of the B domain were present while the $α_3$ helix did not form. The X ray crystallographic analysis reported by Deisenhofer, supra, and the mutagenesis studies reported by Popplewell et al., *Protein Eng.,* 4: 963–970 (1991) and Cedergren et al., *Protein Eng.,* 6: 441–448 (1993) have also identified ten residues within $α_1$ and $α_2$ and nine residues within the Fc region of IgG which participate in the protein-protein interaction.

The interaction between protein A and IgG forms the basis of many immunoaffinity-based purification procedures for antibodies (Hjelm, *FEBS Lett.,* 28: 73–76 (1972)), antibody fragments and antigens (Sisson and Carter, *Immunol. Meth.,* 127: 215–22- (1990)). Bottomley et al., *J. Immunol. Meth.,* 182: 185–192 (1995) reported that truncating B domain variant peptides lacking the 13 C-terminal residues of the $α_3$ helix causes a decrease in IgG-binding activity. Bottomley et al. also characterized various mutations of residues within the $α_1$ and $α_2$ regions found to reduce or not affect IgG-binding activity.

SUMMARY OF THE INVENTION

In one aspect, the invention provides a compound represented by Formula (I):

$X_1$-$AA_6$-$AA_7$-$AA_8$-$AA_9$-Gln-Gln-$AA_{12}$-$AA_{13}$-Phe-Tyr-Glu-Ala-Leu-His-Asp-Pro-Asn-Leu-Asn-Glu-Glu-Gln-Arg-Asn-Ala-Lys-Ile-$AA_{33}$-Ser-Ile-$AA_{36}$-Asp-Asp-$X_2$ (SEQ ID NO:1)  (I)

where $X_1$ is selected from the group consisting of H, $C_1$–$C_6$alkanoyl, and Z-Ala-Val-$AA_3$-$AA_4$-$AA_5$ (SEQ ID NO:2);

where

Z is selected from the group consisting of H and $C_1$–$C_6$ alkanoyl;

$AA_3$ is selected from the group consisting of Asp, Arg, and Ala;

$AA_4$ is selected from the group consisting of Asn and Gln; and $AA_5$ is selected from the group consisting of Lys, Gly, and Ser;

$AA_6$ is selected from the group consisting of Phe and Gly;

$AA_7$ is selected from the group consisting of Asn and Trp;

$AA_8$ is selected from the group consisting of Lys and Met;

$AA_9$ is selected from the group consisting of Glu, Gln, and Arg;

$AA_{12}$ is selected from the group consisting of Asn, Ala, and Arg;

$AA_{13}$ is selected from the group consisting of Ala and Arg;

$AA_{33}$ is selected from the group consisting of Gln and Lys;

$AA_{36}$ is selected from the group consisting of Lys and Arg; and $X_2$ is selected from the group consisting of $OR_1$ and $NR_1R_2$ where $R_1$ and $R_2$ are independently selected from the group consisting of H, $C_1$–$C_6$alkyl, $C_6$–$C_{12}$aryl and $C_6$–$C_{12}$aryl-$C_1$–$C_6$alkyl.

In another aspect, the invention provides a compound represented by Formula (II):

(II)
(SEQ ID NO:3)

$X_1$-$AA_6$-$AA_7$-$AA_8$-$AA_9$-Cys-Gln-$AA_{12}$-$AA_{13}$-Phe-Tyr-Glu-
          |
     S------------S
          |
$X_2$-Cys-Asp-Asp-$AA_{36}$-Ile-Ser-$AA_{33}$-Ile-Lys-Ala-Asn-
                              -Ala-Leu-His-Asp-Pro-Asn
                              ⋮
                              -Arg-Gln-Glu-Glu-Asn-Leu where $X_1$ is selected from the group consisting of H, $C_1$–$C_6$alkanoyl, and Z-Ala-Val-$AA_3$-$AA_4$-$AA_5$ (SEQ ID NO:2);

where

Z is selected from the group consisting of H and $C_1$–$C_6$alkanoyl;

$AA_3$ is selected from the group consisting of Asp, Arg, and Ala;

$AA_4$ is selected from the group consisting of Asn and Gln; and $AA_5$ is selected from the group consisting of Lys, Gly, and Ser;

$AA_6$ is selected from the group consisting of Phe and Gly;

$AA_7$ is selected from the group consisting of Asn and Trp;

$AA_8$ is selected from the group consisting of Lys and Met;

$AA_9$ is selected from the group consisting of Glu, Gln, and Arg;

$AA_{12}$ is selected from the group consisting of Asn, Ala, and Arg;

$AA_{13}$ is selected from the group consisting of Ala and Arg;

AA$_{33}$ is selected from the group consisting of Gln and Lys;

AA$_{36}$ is selected from the group consisting of Lys and Arg; and

X$_2$ is selected from the group consisting of OR$_1$ and NR$_1$R$_2$ where R$_1$ and R$_2$ are independently selected from the group consisting of H, C$_1$–C$_6$alkyl, C$_6$–C$_{12}$aryl and C$_6$–C$_{12}$aryl-C$_1$–C$_6$alkyl.

BRIEF DESCRIPTION OF THE FIGURES

The file of this patent contains at least one drawing executed in color. Copies of this patent with color drawings will be provided by the Patent and Trademark Office upon request and payment of the necessary fee.

FIG. 1 is a ribbon diagram of the B-domain of Protein A (purple) in complex with the CH2, CH3 fragment of an IgG$_1$ (blue) taken from x-ray coordinates. Helix-3 appears disordered in the crystal structure although NMR experiments indicate that it is in fact helical. In this figure helix-3 has been modeled as a helix.

FIGS. 2A–D are ribbon diagrams showing helices-1 and helix-2 of the truncated Z-domain modeled from the x-ray structure. FIG. 2A depicts residues that were randomly mutated and selected from the Exoface Library. Residues that were conserved as the wild-type after selection are shown in blue and those that demonstrated strong consensus to non-wild-type amino acids are shown in yellow. The transparent helix represents the position occupied by helix-3 in the native Z domain; it was modeled as shown in FIG. 1. Replacement residues were aligned on the C$_a$, C$_b$ vector of the wild type residue. FIG. 2B depicts residues (colored as in FIG. 2A) that were randomly mutated and selected from the Intraface Library. FIG. 2C depicts residues (colored as in FIG. 2A) that were randomly mutated and selected from the five Interface Libraries. Interface library 3A covers residues which are not depicted in this structure. FIG. 2D depicts an overhead view of the Interface Libraries looking down the helical axis.

FIGS. 3A–B are graphs representing the CD spectra of the starting 38-residue peptide, and the intraface and interface optimized peptides (FIG. 3A) and the extent of helicity calculated for these peptides directly from the CD spectra (FIG. 3B). Data was collected and curves fit as described in the Materials and Methods section in Example 1 below. These values can be compared to the theoretical maximum value as determined by inspection of the structure of the first two-helices in the intact B-domain.

DETAILED DESCRIPTION OF THE PREFERRED EMBODIMENTS

A. Definitions

Terms used in the claims and specification are defined as set forth below unless otherwise specified.

The terms "Z domain", "Z domain of protein A", "wild type Z domain", etc., are used interchangeably herein and mean the three helix, 59 amino acid peptide reported by Nilsson et al., *Protein Engng.*, 1: 107–113 (1987) that spans a portion of the IgG-binding B domain of staphylococcal protein A, and has the amino acid sequence:
AVDNKFNKEQQNAFYEILHLPNLNEEQRNAFIQS LKDDPSQSANLLAEAKKLNDAQAPK (SEQ ID NO:4)

The term "C$_1$–C$_6$ alkyl" means a branched, unbranched or cyclic, saturated aliphatic hydrocarbon substituent, having the number of carbon atoms specified. Representative examples of these alkyl radicals include methyl, ethyl, n-propyl, isopropyl, n-butyl, sec-butyl, tert-butyl, n-pentyl, 2-methylbutyl, 2,2-dimethylpropyl, n-hexyl, 2-methylpentyl, 2,2-dimethylbutyl, cyclohexyl and the like. The terms "lower alkyl" and "C$_1$–C$_6$alkyl" are synonymous and used interchangeably. A preferred "C$_1$–C$_6$ alkyl" group is methyl.

The term "C$_1$–C$_6$ alkanoyl" encompasses groups such as formyl, acetyl, propionyl, butyryl, isobutyryl, valeryl, isovaleryl, pivaloyl, caproyl, and the like.

The term "C$_6$–C$_{12}$aryl" means a homocyclic hydrocarbon aromatic radical, whether or not fused, having the number of carbon atoms designated. Preferred aryl groups include phenyl, napthyl, biphenyl, phenanthrenyl, naphthacenyl, and the like (see e.g. *Lang's Handbook of Chemistry* (Dean, J. A., ed) 13th ed. Table 7–2 [1985]).

The term "C$_6$–C$_{12}$aryl-C$_1$–C$_6$alkyl" means one, two, or three aryl groups having the number of carbon atoms designated, appended to an alkyl radical having the number of carbon atoms designated including but not limited to benzyl, naphthylmethyl, phenethyl, benzyhydryl (diphenylmethyl), fluorenyl, trityl, and the like. A preferred arylalkyl group is the benzyl group.

Amino acids and amino acid residues described herein may be referred to according to the accepted one or three letter code provided in the table below. Unless otherwise specified, these amino acids or residues are of the naturally occurring L stereoisomer form.

| Common Name | One-Letter Symbol | Three-Letter Symbol |
|---|---|---|
| Alanine | A | Ala |
| Arginine | R | Arg |
| Asparagine | N | Asn |
| Aspartic acid | D | Asp |
| Cysteine | C | Cys |
| Glutamine | Q | Gln |
| Glutamic acid | E | Glu |
| Glycine | G | Gly |
| Histidine | H | His |
| Isoleucine | I | Ile |
| Leucine | L | Leu |
| Lysine | K | Lys |
| Methionine | M | Met |
| Phenylalanine | F | Phe |
| Proline | P | Pro |
| Serine | S | Ser |
| Threonine | T | Thr |
| Tryptophan | W | Trp |
| Tyrosine | Y | Tyr |

In general, unless otherwise specified, the abbreviations used for the designation of amino acids and the protective groups used therefor are based on the recommendations of the IUPAC-IUB Commission of Biochemical Nomenclature (*Biochemistry*, 11: 1726–1732 (1972)).

As used herein, the terms "desired protein", "desired polypeptide", "selected polypeptide" or "selected protein" are used interchangeably and refer generally to any peptide or protein having more than about 5 amino acids. The polypeptides may be homologous to, or preferably, may be exogenous, meaning that they are heterologous, i.e., foreign, to the recombinant host cell in which the polypeptide is expressed, such as a human protein or a yeast protein produced in bacterial host cells. Preferably, mammalian polypeptides (polypeptides that were originally derived from a mammalian organism) are used.

Examples of mammalian polypeptides include, but are not limited to, molecules such as, e.g., renin, a growth hormone, including human growth hormone; bovine growth hormone; growth hormone releasing factor; parathyroid hormone; thyroid stimulating hormone; lipoproteins; alpha-1-antitrypsin; insulin A-chain; insulin B-chain; proinsulin; follicle stimulating hormone; calcitonin; luteinizing hormone; glucagon; clotting factors such as factor VIIIC, factor IX, tissue factor, and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; RANTES (regulated on activation normally T-cell expressed and secreted); human macrophage inflammatory protein (MIP-1-alpha); a serum albumin such as human serum albumin; mullerian-inhibiting substance; relaxin A-chain; relaxin B-chain; prorelaxin; mouse gonadotropin-associated peptide; a microbial protein, such as beta-lactamase; DNase; inhibin; activin; vascular endothelial growth factor (VEGF); receptors for hormones or growth factors; integrin; protein A or D; rheumatoid factors; a neurotrophic factor such as bone-derived neurotrophic factor (BDNF), neurotrophin-3, -4, -5, or -6 (NT-3, NT-4, NT-5, or NT-6), or a nerve growth factor such as NGF-β; platelet-derived growth factor (PDGF); fibroblast growth factor such as aFGF and bFGF; epidermal growth factor (EGF); transforming growth factor (TGF) such as TGF-alpha and TGF-beta, including TGF-β1, TGF-β2, TGF-β3, TGF-β4, or TGF-β5; insulin-like growth factor-I and -II (IGF-I and IGF-II); des(1–3)-IGF-I (brain IGF-I), insulin-like growth factor binding proteins; CD proteins such as CD-3, CD-4, CD-8, and CD-19; erythropoietin; osteoinductive factors; immunotoxins; a bone morphogenetic protein (BMP); an interferon such as interferon-alpha, -beta, and -gamma; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor; viral antigen such as, for example, a portion of the AIDS envelope; transport proteins; homing receptors; addressins; regulatory proteins; antibodies; and fragments of any of the above-listed polypeptides.

B. General Methods

In general, the invention provides variants of the Z domain of staphylococcal protein A for use in affinity purification of proteins, such as gamma-immunoglobulins (IgGs) and IgG-carrying fusion proteins (immunoadhesins), for use in cell separation techniques for IgG-bearing cells, and for use in the treatment of staphylococcal infections. The Z domain variants of the invention provide the practitioner with molecules that are approximately 50% smaller than the wild type Z domain while retaining IgG-binding activities that are equivalent or comparable to that of the intact, wild type Z domain of protein A. In the case of protein purification, the Z domain variants can be fused to recombinant proteins as affinity purification handles capable of achieving single-step, quantitative purification of fusion proteins by IgG-ligand chromatography. The reduced size of the present Z domain variants confers the advantages of lower cost (e.g. conservation of biosynthetic or synthetic chemical production resources), greater versatility and reduced influence on the higher order structure of the parent protein and its activity in fusion protein form. Likewise, the smaller size of the present Z domain variants facilitates their use as ligands in affinity chromatography of gamma-immunoglobulins (IgGs), IgG fusion proteins and IgG-bearing cells with advantages such as greater stability (enabling prolonged use as ligands in affinity chromatography), smaller size (providing higher density ligand on solid supports for higher binding capacity/yield of affinity chromatography), and greater cost efficiency associated therewith, and reduces the liklihood of copurification of contaminants which interact with areas of the Z domain that do not directly contact the protein A-binding determinants of IgG. Additionally, the peptides of the invention are less expensive to produce as pharmaceutical agents and are less likely to elicit an undesired (e.g. inactivating) immune response than are full length, wild type Z domain peptides.

I. Preferred Embodiments

In one aspect, the invention provides for Z domain variant peptides which lack the α$_3$ helix present in the full length, wild type Z domain, causing a loss in the conformational stability and IgG-binding activity of the variant peptides, and which are further engineered to largely restore the lost stability and IgG-binding activity by improving the quality of intramolecular contacts in the remaining peptide scaffold through select amino acid substitutions. Accordingly, the invention provides linear Z domain variant peptides represented by Formula (I):

$X_1$-$AA_6$-$AA_7$-$AA_8$-$AA_9$-Gln-Gln-$AA_{12}$-$AA_{13}$-Phe-Tyr-Glu-Ala-Leu-His-Asp-Pro-Asn-Leu-Asn-Glu-Glu-Gln-Arg-Asn-Ala-Lys-Ile-$AA_{33}$-Ser-Ile-$AA_{36}$-Asp-Asp-$X_2$ (SEQ ID NO:1)  (I)

where $X_1$ is selected from the group consisting of H, $C_1$–$C_6$alkanoyl, and Z-Ala-Val-$AA_3$-$AA_4$-$AA_5$ (SEQ ID NO:2); 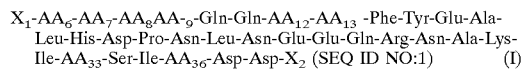

where

Z is selected from the group consisting of H and $C_1$–$C_6$ alkanoyl;

$AA_3$ is selected from the group consisting of Asp, Arg, and Ala;

$AA_4$ is selected from the group consisting of Asn and Gln; and $AA_5$ is selected from the group consisting of Lys, Gly, and Ser;

$AA_6$ is selected from the group consisting of Phe and Gly;

$AA_7$ is selected from the group consisting of Asn and Trp;

$AA_8$ is selected from the group consisting of Lys and Met;

$AA_9$ is selected from the group consisting of Glu, Gln, and Arg;

$AA_{12}$ is selected from the group consisting of Asn, Ala, and Arg;

$AA_{13}$ is selected from the group consisting of Ala and Arg;

$AA_{33}$ is selected from the group consisting of Gln and Lys;

$AA_{36}$ is selected from the group consisting of Lys and Arg; and $X_2$ is selected from the group consisting of $OR_1$ and $NR_1R_2$ where $R_1$ and $R_2$ are independently selected from the group consisting of H, $C_1$–$C_6$alkyl, $C_6$–$C_{12}$aryl and $C_6$–$C_{12}$aryl-$C_1$–$C_6$alkyl.

In one embodiment, the invention provides peptides of Formula (I) wherein $X_1$ is Z-Ala-Val-$AA_3$-$AA_4$-$AA_5$ (SEQ ID NO:2), $AA_3$ is Arg, and $AA_5$ is Gly.

In another embodiment, the invention provides peptides of Formula (I) wherein $X_1$ is Z-Ala-Val-$AA_3$-$AA_4$-$AA_5$ (SEQ ID NO:2), $AA_3$ is Arg, $AA_5$ is Gly, $AA_4$ is Asn, $AA_6$ is Phe, $AA_7$ is Asn, $AA_8$ is Lys, $AA_9$ is Glu, $AA_{12}$ is Asn, $AA_{13}$ is Arg, $AA_{33}$ is Gln, and $AA_{36}$ is Lys.

In yet another embodiment, the invention provides peptides of Formula (I) wherein $X_1$ is Z-Ala-Val-$AA_3$-$AA_4$-$AA_5$ (SEQ ID NO:2), $AA_3$ is Arg, $AA_5$ is Gly, and $AA_{12}$ is Ala.

Further provided herein are peptides of Formula (I) wherein $X_1$ is Z-Ala-Val-$AA_3$-$AA_4$-$AA_5$ (SEQ ID NO:2), $AA_3$ is Arg, $AA_5$ is Gly, $AA_4$ is Asn, $AA_6$ is Phe, $AA_7$ is Asn, $AA_8$ is Lys, $AA_9$ is Glu, $AA_{12}$ is Ala, $AA_{13}$ is Arg, $AA_{33}$ is Gln, and $AA_{36}$ is Lys.

In still another embodiment, the invention provides peptides of Formula (I) wherein $AA_8$ is Met and $AA_9$ is Gln.

Also provided herein are peptides of Formula (I) wherein $AA_8$ is Met, $AA_9$ is Gln, $X_1$ is Z-Ala-Val-$AA_3$-$AA_4$-$AA_5$ (SEQ ID NO:2), $AA_3$ is Asp, $AA_4$ is Asn, $AA_5$ is Lys, $AA_6$ is Phe, $AA_7$ is Asn, $AA_{12}$ is Asn, $AA_{13}$ is Arg, $AA_{33}$ is Gln, and $AA_{36}$ is Lys.

Additionally provided herein are peptides of Formula (I) wherein $AA_8$ is Met, $AA_9$ is Gln, and $AA_{12}$ is Ala.

In a further aspect, the invention provides peptides of Formula (I) wherein $AA_8$ is Met, $AA_9$ is Gln, $X_1$ is Z-Ala-Val-$AA_3$-$AA_4$-$AA_5$ (SEQ ID NO:2), $AA_3$ is Asp, $AA_4$ is Asn, $AA_5$ is Lys, $AA_6$ is Phe, $AA_7$ is Asn, $AA_{12}$ is Ala, $AA_{13}$ is Arg, $AA_{33}$ is Gln, and $AA_{36}$ is Lys.

In an additional embodiment, the invention provides peptides of Formula (I) wherein $AA_{12}$ is Arg and $AA_{13}$ is Ala.

In a further embodiment, the invention provides peptides of Formula (I) wherein $AA_{12}$ is Arg, $AA_{13}$ is Ala, $X_1$ is Z-Ala-Val-$AA_3$-$AA_4$-$AA_5$ (SEQ ID NO:2), $AA_3$ is Asp, $AA_4$ is Asn, $AA_5$ is Lys, $AA_6$ is Phe, $AA_7$ is Asn, $AA_8$ is Lys, $AA_9$ is Glu, $AA_{33}$ is Gln, and $AA_{36}$ is Lys.

Also encompassed within the scope of the invention are peptides of Formula (I) wherein $AA_{12}$ is Ala and $AA_{13}$ is Ala.

Further encompassed within the scope of the invention are peptides of Formula (I) wherein $AA_{12}$ is Ala, $AA_{13}$ is Ala, $X_1$ is Z-Ala-Val-$AA_3$-$AA_4$-$AA_5$ (SEQ ID NO:2), $AA_3$ is Asp, $AA_4$ is Asn, $AA_5$ is Lys, $AA_6$ is Phe, $AA_7$ is Asn, $AA_8$ is Lys, $AA_9$ is Glu, $AA_{33}$ is Gln; and $AA_{36}$ is Lys.

In another aspect, the invention provides a compound selected from the group consisting of Z-Ala-Val-Asp-Asn-Lys-Phe-Asn-Lys-Glu-Gln-Gln-Asn-Arg-Phe-Tyr-Glu-Ala-Leu-His-Asp-Pro-Asn-Leu-Asn-Glu-Glu-Gln-Arg-Asn-Ala-Lys-Ile-Gln-Ser-Ile-Lys-Asp-Asp-$X_2$ (SEQ ID NO:5);

Z-Ala-Val-Arg-Asn-Gly-Phe-Asn-Lys-Glu-Gln-Gln-Asn-Arg-Phe-Tyr-Glu-Ala-Leu-His-Asp-Pro-Asn-Leu-Asn-Glu-Glu-Gln-Arg-Asn-Ala-Lys-Ile-Gln-Ser-Ile-Lys-Asp-Asp-$X_2$ (SEQ ID NO:6);

Z-Ala-Val-Ala-Gln-Ser-Phe-Asn-Lys-Glu-Gln-Gln-Asn-Arg-Phe-Tyr-Glu-Ala-Leu-His-Asp-Pro-Asn-Leu-Asn-Glu-Glu-Gln-Arg-Asn-Ala-Lys-Ile-Gln-Ser-Ile-Lys-Asp-Asp-$X_2$ (SEQ ID NO:7);

Z-Ala-Val-Asp-Asn-Lys-Phe-Asn-Met-Gln-Gln-Gln-Asn-Arg-Phe-Tyr-Glu-Ala-Leu-His-Asp-Pro-Asn-Leu-Asn-Glu-Glu-Gln-Arg-Asn-Ala-Lys-Ile-Gln-Ser-Ile-Lys-Asp-Asp-$X_2$ (SEQ ID NO:8);

Z-Ala-Val-Asp-Asn-Lys-Gly-Trp-Met-Arg-Gln-Gln-Asn-Arg-Phe-Tyr-Glu-Ala-Leu-His-Asp-Pro-Asn-Leu-Asn-Glu-Glu-Gln-Arg-Asn-Ala-Lys-Ile-Gln-Ser-Ile-Lys-Asp-Asp-$X_2$ (SEQ ID NO:9);

Z-Ala-Val-Asp-Asn-Lys-Phe-Asn-Lys-Glu-Gln-Gln-Arg-Arg-Phe-Tyr-Glu-Ala-Leu-His-Asp-Pro-Asn-Leu-Asn-Glu-Glu-Gln-Arg-Asn-Ala-Lys-Ile-Gln-Ser-Ile-Lys-Asp-Asp-$X_2$ (SEQ ID NO:10);

Z-Ala-Val-Asp-Asn-Lys-Phe-Asn-Lys-Glu-Gln-Gln-Arg-Ala-Phe-Tyr-Glu-Ala-Leu-His-Asp-Pro-Asn-Leu-Asn-Glu-Glu-Gln-Arg-Asn-Ala-Lys-Ile-Gln-Ser-Ile-Lys-Asp-Asp-$X_2$ (SEQ ID NO:11);

Z-Ala-Val-Asp-Asn-Lys-Phe-Asn-Lys-Glu-Gln-Gln-Asn-Arg-Phe-Tyr-Glu-Ala-Leu-His-Asp-Pro-Asn-Leu-Asn-Glu-Glu-Gln-Arg-Asn-Ala-Lys-Ile-Lys-Ser-Ile-Arg-Asp-Asp-$X_2$ (SEQ ID NO:12);

Z-Ala-Val-Arg-Asn-Gly-Phe-Asn-Met-Gln-Gln-Gln-Arg-Arg-Phe-Tyr-Glu-Ala-Leu-His-Asp-Pro-Asn-Leu-Asn-Glu-Glu-Gln-Arg-Asn-Ala-Lys-Ile-Lys-Ser-Ile-Arg-Asp-Asp-$X_2$ (SEQ ID NO:13);

Z-Ala-Val-Ala-Gln-Ser-Phe-Asn-Met-Gln-Gln-Gln-Arg-Arg-Phe-Tyr-Glu-Ala-Leu-His-Asp-Pro-Asn-Leu-Asn-Glu-Glu-Gln-Arg-Asn-Ala-Lys-Ile-Lys-Ser-Ile-Arg-Asp-Asp-$X_2$ (SEQ ID NO:14); and $X_1$-Phe-Asn-Met-Gln-Gln-Gln-Arg-Arg-Phe-Tyr-Glu-Ala-Leu-His-Asp-Pro-Asn-Leu-Asn-Glu-Glu-Gln-Arg-Asn-Ala-Lys-Ile-Lys-Ser-Ile-Arg-Asp-Asp-$X_2$ (SEQ ID NO: 15);

where

Z is selected from the group consisting of H and $C_1$–$C_6$alkanoyl;

$X_1$ is selected from the group consisting of H and $C_1$–$C_6$ alkanoyl; and $X_2$ is selected from the group consisting of $OR_1$ and $NR_1R_2$ where $R_1$ and $R_2$ are independently selected from the group consisting of H, $C_1$–$C_6$ alkyl, $C_6$–$C_{12}$aryl and $C_6$–$C_{12}$aryl-$C_1$–$C_6$alkyl.

In an additional aspect, the invention provides a compound selected from the group consisting of Z-Ala-Val-Asp-Asn-Lys-Phe-Asn-Lys-Glu-Gln-Gln-Ala-Arg-Phe-Tyr-Glu-Ala-Leu-His-Asp-Pro-Asn-Leu-Asn-Glu-Glu-Gln-Arg-Asn-Ala-Lys-Ile-Gln-Ser-Ile-Lys-Asp-Asp-$X_2$ (SEQ ID NO:16);

Z-Ala-Val-Arg-Asn-Gly-Phe-Asn-Lys-Glu-Gln-Gln-Ala-Arg-Phe-Tyr-Glu-Ala-Leu-His-Asp-Pro-Asn-Leu-Asn-Glu-Glu-Gln-Arg-Asn-Ala-Lys-Ile-Gln-Ser-Ile-Lys-Asp-Asp-$X_2$ (SEQ ID NO:17);

Z-Ala-Val-Ala-Gln-Ser-Phe-Asn-Lys-Glu-Gln-Gln-Ala-Arg-Phe-Tyr-Glu-Ala-Leu-His-Asp-Pro-Asn-Leu-Asn-Glu-Glu-Gln-Arg-Asn-Ala-Lys-Ile-Gln-Ser-Ile-Lys-Asp-Asp-$X_2$ (SEQ ID NO:18);

Z-Ala-Val-Asp-Asn-Lys-Phe-Asn-Met-Gln-Gln-Gln-Ala-Arg-Phe-Tyr-Glu-Ala-Leu-His-Asp-Pro-Asn-Leu-Asn-Glu-Glu-Gln-Arg-Asn-Ala-Lys-Ile-Gln-Ser-Ile-Lys-Asp-Asp-$X_2$ (SEQ ID NO:19);

Z-Ala-Val-Asp-Asn-Lys-Gly-Trp-Met-Arg-Gln-Gln-Ala-Arg-Phe-Tyr-Glu-Ala-Leu-His- Asp-Pro-Asn-Leu-Asn-Glu-Glu-Gln-Arg-Asn-Ala-Lys-Ile-Gln-Ser-Ile-Lys-Asp-Asp-$X_2$ (SEQ ID NO:20);

Z-Ala-Val-Asp-Asn-Lys-Phe-Asn-Lys-Glu-Gln-Gln-Ala-Ala-Phe-Tyr-Glu-Ala-Leu-His-Asp-Pro-Asn-Leu-Asn-Glu-Glu-Gln-Arg-Asn-Ala-Lys-Ile-Gln-Ser-Ile-Lys-Asp-Asp-$X_2$ (SEQ ID NO:21);

Z-Ala-Val-Asp-Asn-Lys-Phe-Asn-Lys-Glu-Gln-Gln-Ala-Arg-Phe-Tyr-Glu-Ala-Leu-His-Asp-Pro-Asn-Leu-Asn-Glu-Glu-Gln-Arg-Asn-Ala-Lys-Ile-Lys-Ser-Ile-Arg-Asp-Asp-$X_2$ (SEQ ID NO:22);

Z-Ala-Val-Arg-Asn-Gly-Phe-Asn-Met-Gln-Gln-Gln-Ala-Arg-Phe-Tyr-Glu-Ala-Leu-His-Asp-Pro-Asn-Leu-Asn-Glu-Glu-Gln-Arg-Asn-Ala-Lys-Ile-Lys-Ser-Ile-Arg-Asp-Asp-$X_2$ (SEQ ID NO:23);

Z-Ala-Val-Ala-Gln-Ser-Phe-Asn-Met-Gln-Gln-Gln-Ala-Arg-Phe-Tyr-Glu-Ala-Leu-His-Asp-Pro-Asn-Leu-Asn-Glu-Glu-Gln-Arg-Asn-Ala-Lys-Ile-Lys-Ser-Ile-Arg-Asp-Asp-$X_2$ (SEQ ID NO:24); and $X_1$-Phe-Asn-Met-Gln-Gln-Gln-Ala-Arg-Phe-Tyr-Glu-Ala-Leu-His-Asp-Pro-Asn-Leu-Asn-Glu-Glu-Gln-Arg-Asn-Ala-Lys-Ile-Lys-Ser-Ile-Arg-Asp-Asp-$X_2$ (SEQ ID NO:25);

where

Z is selected from the group consisting of H and $C_1$–$C_6$ alkanoyl;

$X_1$ is selected from the group consisting of H and $C_1$–$C_6$alkanoyl; and $X_2$ is selected from the group consisting of $OR_1$ and $NR_1R_2$ where $R_1$ and $R_2$ are independently selected from the group consisting of H, $C_1$–$C_6$ alkyl, $C_6$–$C_{12}$aryl and $C_6$–$C_{12}$aryl-$C_1$–$C_6$alkyl.

In a preferred embodiment, the invention provides peptides of Formula (I) wherein $X_1$ is Z-Ala-Val-$AA_3$-$AA_4$-$AA_5$ (SEQ ID NO:2), $AA_3$ is Ala, $AA_4$ is Gln, and $AA_5$ is Ser.

In another preferred embodiment, the invention provides peptides of Formula (I) wherein $X_1$ is Z-Ala-Val-$AA_3$-$AA_4$-$AA_5$ (SEQ ID NO:2), $AA_3$ is Ala, $AA_4$ is Gln, $AA_5$ is Ser, $AA_6$ is Phe, $AA_7$ is Asn, $AA_8$ is Lys, $AA_9$ is Glu, $AA_{12}$ is Asn, $AA_{13}$ is Arg, $AA_{33}$ is Gln, and $AA_{36}$ is Lys.

In yet another aspect, the invention provides peptides of Formula (I) wherein $X_1$ is Z-Ala-Val-$AA_3$-$AA_4$-$AA_5$ (SEQ ID NO:2), $AA_3$ is Ala, $AA_4$ is Gln, $AA_5$ is Ser, and $AA_{12}$ is Ala.

In still another aspect, the invention provides peptides of Formula (I) wherein $X_1$ is Z-Ala-Val-$AA_3$-$AA_4$-$AA_5$ (SEQ ID NO:2), $AA_3$ is Ala, $AA_4$ is Gln, $AA_5$ is Ser, $AA_6$ is Phe, $AA_7$ is Asn, $AA_8$ is Lys, $AA_9$ is Glu, $AA_{12}$ is Ala, $AA_{13}$ is Arg, $AA_{33}$ is Gln, and $AA_{36}$ is Lys.

In yet another preferred embodiment, the invention provides peptides of Formula (I) wherein $X_1$ is $AA_6$ is Gly, $AA_7$ is Trp, $AA_8$ is Met, and $AA_9$ is Arg.

In still another preferred embodiment, the invention provides peptides of Formula (I) wherein $X_1$ is Z-Ala-Val-$AA_3$-$AA_4$-$AA_5$ (SEQ ID NO:2), $AA_6$ is Gly, $AA_7$ is Trp, $AA_8$ is Met, $AA_9$ is Arg, $AA_3$ is Asp, $AA_4$ is Asn, $AA_5$ is Lys, $AA_{12}$ is Asn, $AA_{13}$ is Arg, $AA_{33}$ is Gln; and $AA_{36}$ is Lys.

Also encompassed herein are peptides of Formula (I) wherein $AA_6$ is Gly, $AA_7$ is Trp, $AA_8$ is Met, $AA_9$ is Arg, and $AA_{12}$ is Ala.

Further encompassed herein are peptides of Formula (I) wherein $X_1$ is Z-Ala-Val-$AA_3$-$AA_4$-$AA_5$ (SEQ ID NO:2), $AA_6$ is Gly, $AA_7$ is Trp, $AA_8$ is Met, $AA_9$ is Arg, $AA_3$ is Asp, $AA_4$ is Asn, $AA_5$ is Lys, $AA_{12}$ is Ala, $AA_{13}$ is Arg, $AA_{33}$ is Gln; and $AA_{36}$ is Lys.

In a further preferred embodiment, the invention provides peptides of Formula (I) wherein $AA_{12}$ is Arg.

Also preferred are peptides of Formula (I) wherein $X_1$ is Z-Ala-Val-$AA_3$-$AA_4$-$AA_5$ (SEQ ID NO:2), $AA_{12}$ is Arg, $AA_3$ is Asp, $AA_4$ is Asn, $AA_5$ is Lys, $AA_6$ is Phe, $AA_7$ is Asn, $AA_8$ is Lys, $AA_9$ is Glu, $AA_{13}$ is Arg, $AA_{33}$ is Gln, and $AA_{36}$ is Lys.

Further encompassed within the scope of the invention are peptides of Formula (I) wherein $AA_{12}$ is Ala.

Additionally encompassed within the scope of the invention are peptides of Formula (I) wherein $X_1$ is Z-Ala-Val-$AA_3$-$AA_4$-$AA_5$ (SEQ ID NO:2), $AA_{12}$ is Ala, $AA_3$ is Asp, $AA_4$ is Asn, $AA_5$ is Lys, $AA_6$ is Phe, $AA_7$ is Asn, $AA_8$ is Lys, $AA_9$ is Glu, $AA_{13}$ is Arg, $AA_{33}$ is Gln, and $AA_{36}$ is Lys.

In an additional preferred embodiment, the invention provides peptides of Formula (I) wherein $AA_{33}$ is Lys and $AA_{36}$ is Arg.

In still another preferred embodiment, the invention provides peptides of Formula (I) wherein $X_1$ is Z-Ala-Val-$AA_3$-$AA_4$-$AA_5$ (SEQ ID NO:2), $AA_{33}$ is Lys, $AA_{36}$ is Arg, $AA_3$ is Asp, $AA_4$ is Asn, $AA_5$ is Lys, $AA_6$ is Phe, $AA_7$ is Asn, $AA_8$ is Lys, $AA_9$ is Glu, $AA_{12}$ is Asn, and $AA_{13}$ is Arg.

Further encompassed herein are peptides of Formula (I) wherein $AA_{33}$ is Lys, $AA_{36}$ is Arg, and $AA_{12}$ is Ala.

Additionally encompassed herein are peptides of Formula (I) wherein $X_1$ is Z-Ala-Val-$AA_3$-$AA_4$-$AA_5$ (SEQ ID NO:2), $AA_{33}$ is Lys, $AA_{36}$ is Arg, $AA_3$ is Asp, $AA_4$ is Asn, $AA_5$ is Lys, $AA_6$ is Phe, $AA_7$ is Asn, $AA_8$ is Lys, $AA_9$ is Glu, $AA_{12}$ is Ala, and $AA_{13}$ is Arg.

In yet another preferred embodiment, the invention provides peptides of Formula (I) wherein $X_1$ is Z-Ala-Val-$AA_3$-$AA_4$-$AA_5$ (SEQ ID NO:2), $AA_3$ is Arg, $AA_5$ is Gly, $AA_8$ is Met, $AA_9$ is Gln, $AA_{12}$ is Arg, $AA_{33}$ is Lys, and $AA_{36}$ is Arg.

In a more preferred embodiment, the invention provides peptides of Formula (I) wherein $X_1$ is Z-Ala-Val-$AA_3$-$AA_4$-$AA_5$ (SEQ ID NO:2), $AA_3$ is Arg, $AA_5$ is Gly, AA, is Met, $AA_9$ is Gln, $AA_{12}$ is Arg, $AA_{33}$ is Lys, $AA_{36}$ is Arg, $AA_4$ is Asn, $AA_6$ is Phe, $AA_7$ is Asn, and $AA_3$ is Arg.

Also provided herein are peptides of Formula (I) wherein $X_1$ is Z-Ala-Val-$AA_3$-$AA_4$-$AA_5$ (SEQ ID NO:2), $AA_3$ is Arg, $AA_5$ is Gly, $AA_8$ is Met, $AA_9$ is Gln, $AA_{12}$ is Ala, $AA_{33}$ is Lys, and $AA_{36}$ is Arg.

Further provided herein are peptides of Formula (I) wherein $X_1$ is Z-Ala-Val-$AA_3$-$AA_4$-$AA_5$ (SEQ ID NO:2), $AA_3$ is Arg, $AA_5$ is Gly, $AA_8$ is Met, $AA_9$ is Gln, $AA_{12}$ is Ala, $AA_{33}$ is Lys, $AA_{36}$ is Arg, $AA_4$ is Asn, $AA_6$ is Phe, $AA_7$ is Asn, and $AA_{13}$ is Arg.

In an additional preferred embodiment, the invention provides peptides of Formula (I) wherein $X_1$ is Z-Ala-Val-$AA_3$-$AA_4$-$AA_5$ (SEQ ID NO:2), $AA_3$ is Ala, $AA_4$ is Gln, $AA_5$ is Ser, $AA_8$ is Met, $AA_9$ is Gln, $AA_{12}$ is Arg, $AA_{33}$ is Lys, and $AA_{36}$ is Arg.

In a more preferred embodiment, the invention provides peptides of Formula (I) wherein $X_1$ is Z-Ala-Val-$AA_3$-$AA_4$-$AA_5$ (SEQ ID NO:2), $AA_3$ is Ala, $AA_4$ is Gln, $AA_5$ is Ser, $AA_8$ is Met, $AA_9$ is Gln, $AA_{12}$ is Arg, $AA_{33}$ is Lys, $AA_{36}$ is Arg, $AA_6$ is Phe, $AA_7$ is Asn, and $AA_{13}$ is Arg.

Additionally provided herein are peptides of Formula (I) wherein $X_1$ is Z-Ala-Val-$AA_3$-$AA_4$-$AA_5$ (SEQ ID NO:2), $AA_3$ is Ala, $AA_4$ is Gln, $AA_5$ is Ser, $AA_8$ is Met, $AA_9$ is Gln, $AA_{12}$ is Ala, $AA_{33}$ is Lys, and $AA_{36}$ is Arg.

In another embodiment, the invention provides peptides of Formula (I) wherein X, is Z-Ala-Val-$AA_3$-$AA_4$-$AA_5$ (SEQ ID NO:2), $AA_3$ is Ala, $AA_4$ is Gln, $AA_5$ is Ser, $AA_8$ is Met, $AA_9$ is Gln, $AA_{12}$ is Ala, $AA_{33}$ is Lys, $AA_{36}$ is Arg, $AA_6$ is Phe, $AA_7$ is Asn, and $AA_{13}$ is Arg.

In a particularly preferred embodiment, the invention provides peptides of Formula (I) wherein $X_1$ is H or $C_1$–$C_6$alkanoyl, $AA_8$ is Met, $AA_9$ is Gln, $AA_{12}$ is Arg, $AA_{33}$ is Lys, and $AA_{36}$ is Arg.

In an even more preferred embodiment, the invention provides peptides of Formula (I) wherein $X_1$ is H or $C_1$–$C_6$alkanoyl, $AA_8$ is Met, $AA_9$ is Gln, $AA_{12}$ is Arg, $AA_{33}$ is Lys, $AA_{36}$ is Arg, $AA_6$ is Phe, $AA_7$ is Asn, and $AA_3$ is Arg.

In yet another embodiment, the invention provides peptides of Formula (I) wherein $X_1$ is H or $C_1$–$C_6$alkanoyl, $AA_8$ is Met, $AA_9$ is Gln, $AA_{12}$ is Ala, $AA_{33}$ is Lys, and $AA_{36}$ is Arg.

In still another embodiment, the invention provides peptides of Formula (I) wherein $X_1$ is H or $C_1$–$C_6$alkanoyl, $AA_8$ is Met, $AA_9$ is Gln, $AA_{12}$ is Ala, $AA_{33}$ is Lys, $AA_{36}$ is Arg, $AA_6$ is Phe, $AA_7$ is Asn, and $AA_{13}$ is Arg.

In another aspect, the invention provides peptides represented by Formula (Ia):

$X_1$-$AA_6$-$AA_7$-$AA_8$-$AA_9$-Gln-Gln-$AA_{12}$-$AA_{13}$-Phe-Tyr-Glu-Ala-Leu-His-Asp-Pro-Asn-Leu-Asn-Glu-Glu-Gln-Arg-Asn-Ala-Lys-Ile-$AA_{33}$-Ser-Ile-$AA_{36}$-Asp-Asp (SEQ ID NO:1), (Ia)

where $X_1$ is absent or is Ala-Val-$AA_3$-$AA_4$-$AA_5$ (SEQ ID NO:2);

where $AA_3$ is selected from the group consisting of Asp, Arg, and Ala;

$AA_4$ is selected from the group consisting of Asn and Gln; and

AA$_5$ is selected from the group consisting of Lys, Gly, and Ser;

AA$_6$ is selected from the group consisting of Phe and Gly;

AA$_7$ is selected from the group consisting of Asn and Trp;

AA$_8$ is selected from the group consisting of Lys and Met;

AA$_9$ is selected from the group consisting of Glu, Gln, and Arg;

AA$_{12}$ is selected from the group consisting of Asn, Ala, and Arg;

AA$_{13}$ is selected from the group consisting of Ala and Arg;

AA$_{33}$ is selected from the group consisting of Gln and Lys; and

AA$_{36}$ is selected from the group consisting of Lys and Arg.

In one embodiment, the invention provides peptides of Formula (Ia) wherein X$_1$ is Ala-Val-AA$_3$-AA$_4$-AA$_5$ (SEQ ID NO:2), AA$_3$ is Arg, and AA$_5$ is Gly.

In another embodiment, the invention provides peptides of Formula (Ia) wherein X$_1$ is Ala-Val-AA$_3$-AA$_4$-AA$_5$ (SEQ ID NO:2), AA$_3$ is Arg, AA$_5$ is Gly, AA$_4$ is Asn, AA$_6$ is Phe, AA$_7$ is Asn, AA$_8$ is Lys, AA$_9$ is Glu, AA$_{12}$ is Asn, AA$_{13}$ is Arg, AA$_{33}$ is Gln, and AA$_{36}$ is Lys.

In yet another embodiment, the invention provides peptides of Formula (Ia) wherein X$_1$ is Ala-Val-AA$_3$-AA$_4$-AA$_5$ (SEQ ID NO:2), AA$_3$ is Arg, AA$_5$ is Gly, and AA$_{12}$ is Ala.

Further provided herein are peptides of Formula (Ia) wherein X$_1$ is Ala-Val-AA$_3$-AA$_4$-AA$_5$ (SEQ ID NO:2), AA$_3$ is Arg, AA$_5$ is Gly, AA$_4$ is Asn, AA$_6$ is Phe, AA$_7$ is Asn, AA$_8$ is Lys, AA$_9$ is Glu, AA$_{12}$ is Ala, AA$_{13}$ is Arg, AA$_{33}$ is Gln, and AA$_{36}$ is Lys.

In still another embodiment, the invention provides peptides of Formula (Ia) wherein AA$_8$ is Met and AA$_9$ is Gln.

Also provided herein are peptides of Formula (Ia) wherein AA$_8$ is Met, AA$_9$ is Gln, X$_1$ is Ala-Val-AA$_3$-AA$_4$-AA$_5$ (SEQ ID NO:2), AA$_3$ is Asp, AA$_4$ is Asn, AA$_5$ is Lys, AA$_6$ is Phe, AA$_7$ is Asn, AA$_{12}$ is Asn, AA$_{13}$ is Arg, AA$_{33}$ is Gln, and AA$_{36}$ is Lys.

Additionally provided herein are peptides of Formula (Ia) wherein AA$_8$ is Met, AA$_9$ is Gln, and AA$_{12}$ is Ala.

In a further aspect, the invention provides peptides of Formula (Ia) wherein AA$_8$ is Met, AA$_9$ is Gln, X$_1$ is Ala-Val-AA$_3$-AA$_4$-AA$_5$ (SEQ ID NO:2), AA$_3$ is Asp, AA$_4$ is Asn, AA$_5$ is Lys, AA$_6$ is Phe, AA$_7$ is Asn, AA$_{12}$ is Ala, AA$_{13}$ is Arg, AA$_{33}$ is Gln, and AA$_{36}$ is Lys.

In an additional embodiment, the invention provides peptides of Formula (Ia) wherein AA$_{12}$ is Arg and AA$_{13}$ is Ala.

In a further embodiment, the invention provides peptides of Formula (Ia) wherein AA$_{12}$ is Arg, AA$_{13}$ is Ala, X$_1$ is Ala-Val-AA$_3$-AA$_4$-AA$_5$ (SEQ ID NO:2), AA$_3$ is Asp, AA$_4$ is Asn, AA$_5$ is Lys, AA$_6$ is Phe, AA$_7$ is Asn, AA$_8$ is Lys, AA$_9$ is Glu, AA$_{33}$ is Gln, and AA$_{36}$ is Lys.

Also encompassed within the scope of the invention are peptides of Formula (Ia) wherein AA$_{12}$ is Ala and AA$_{13}$ is Ala.

Further encompassed within the scope of the invention are peptides of Formula (Ia) wherein AA$_{12}$ is Ala, AA$_{13}$ is Ala, X$_1$ is Ala-Val-AA$_3$-AA$_4$-AA$_5$ (SEQ ID NO:2), AA$_3$ is Asp, AA$_4$ is Asn, AA$_5$ is Lys, AA$_6$ is Phe, AA$_7$ is Asn, AA$_8$ is Lys, AA$_9$ is Glu, AA$_{33}$ is Gln; and AA$_{36}$ is Lys.

In another aspect, the invention provides a compound selected from the group consisting of Ala-Val-Asp-Asn-Lys-Phe-Asn-Lys-Glu-Gln-Gln-Asn-Arg-Phe-Tyr-Glu-Ala-Leu-His-Asp-Pro-Asn-Leu-Asn-Glu-Glu-Gln-Arg-Asn-Ala-Lys-Ile-Gln-Ser-Ile-Lys-Asp-Asp (SEQ ID NO:5);

Ala-Val-Arg-Asn-Gly-Phe-Asn-Lys-Glu-Gln-Gln-Asn-Arg-Phe-Tyr-Glu-Ala-Leu-His-Asp-Pro-Asn-Leu-Asn-Glu-Glu-Gln-Arg-Asn-Ala-Lys-Ile-Gln-Ser-Ile-Lys-Asp-Asp (SEQ ID NO:6);

Ala-Val-Ala-Gln-Ser-Phe-Asn-Lys-Glu-Gln-Gln-Asn-Arg-Phe-Tyr-Glu-Ala-Leu-His-Asp-Pro-Asn-Leu-Asn-Glu-Glu-Gln-Arg-Asn-Ala-Lys-Ile-Gln-Ser-Ile-Lys-Asp-Asp (SEQ ID NO:7);

Ala-Val-Asp-Asn-Lys-Phe-Asn-Met-Gln-Gln-Gln-Asn-Arg-Phe-Tyr-Glu-Ala-Leu-His-Asp-Pro-Asn-Leu-Asn-Glu-Glu-Gln-Arg-Asn-Ala-Lys-Ile-Gln-Ser-Ile-Lys-Asp-Asp (SEQ ID NO:8);

Ala-Val-Asp-Asn-Lys-Gly-Trp-Met-Arg-Gln-Gln-Asn-Arg-Phe-Tyr-Glu-Ala-Leu-His-Asp-Pro-Asn-Leu-Asn-Glu-Glu-Gln-Arg-Asn-Ala-Lys-Ile-Gln-Ser-Ile-Lys-Asp-Asp (SEQ ID NO:9);

Ala-Val-Asp-Asn-Lys-Phe-Asn-Lys-Glu-Gln-Gln-Arg-Arg-Phe-Tyr-Glu-Ala-Leu-His-Asp-Pro-Asn-Leu-Asn-Glu-Glu-Gln-Arg-Asn-Ala-Lys-Ile-Gln-Ser-Ile-Lys-Asp-Asp (SEQ ID NO:10);

Ala-Val-Asp-Asn-Lys-Phe-Asn-Lys-Glu-Gln-Gln-Arg-Ala-Phe-Tyr-Glu-Ala-Leu-His-Asp-Pro-Asn-Leu-Asn-Glu-Glu-Gln-Arg-Asn-Ala-Lys-Ile-Gln-Ser-Ile-Lys-Asp-Asp (SEQ ID NO:11);

Ala-Val-Asp-Asn-Lys-Phe-Asn-Lys-Glu-Gln-Gln-Asn-Arg-Phe-Tyr-Glu-Ala-Leu-His-Asp-Pro-Asn-Leu-Asn-Glu-Glu-Gln-Arg-Asn-Ala-Lys-Ile-Lys-Ser-Ile-Arg-Asp-Asp (SEQ ID NO:12);

Ala-Val-Arg-Asn-Gly-Phe-Asn-Met-Gln-Gln-Gln-Arg-Arg-Phe-Tyr-Glu-Ala-Leu-His-Asp-Pro-Asn-Leu-Asn-Glu-Glu-Gln-Arg-Asn-Ala-Lys-Ile-Lys-Ser-Ile-Arg-Asp-Asp (SEQ ID NO:13);

Ala-Val-Ala-Gln-Ser-Phe-Asn-Met-Gln-Gln-Gln-Arg-Arg-Phe-Tyr-Glu-Ala-Leu-His-Asp-Pro-Asn-Leu-Asn-Glu-Glu-Gln-Arg-Asn-Ala-Lys-Ile-Lys-Ser-Ile-Arg-Asp-Asp (SEQ ID NO:14); and Phe-Asn-Met-Gln-Gln-Gln-Arg-Arg-Phe-Tyr-Glu-Ala-Leu-His-Asp-Pro-Asn-Leu-Asn-Glu-Glu-Gln-Arg-Asn-Ala-Lys-Ile-Lys-Ser-Ile-Arg-Asp-Asp (SEQ ID NO: 15).

In an additional aspect, the invention provides a compound selected from the group consisting of Ala-Val-Asp-Asn-Lys-Phe-Asn-Lys-Glu-Gln-Gln-Ala-Arg-Phe-Tyr-Glu-Ala-Leu-His-Asp-Pro-Asn-Leu-Asn-Glu-Glu-Gln-Arg-Asn-Ala-Lys-Ile-Gln-Ser-Ile-Lys-Asp-Asp (SEQ ID NO:16);

Ala-Val-Arg-Asn-Gly-Phe-Asn-Lys-Glu-Gln-Gln-Ala-Arg-Phe-Tyr-Glu-Ala-Leu-His-Asp-Pro-Asn-Leu-Asn-Glu-Glu-Gln-Arg-Asn-Ala-Lys-Ile-Gln-Ser-Ile-Lys-Asp-Asp (SEQ ID NO:17);

Ala-Val-Ala-Gln-Ser-Phe-Asn-Lys-Glu-Gln-Gln-Ala-Arg-Phe-Tyr-Glu-Ala-Leu-His-Asp-Pro-Asn-Leu-Asn-Glu-Glu-Gln-Arg-Asn-Ala-Lys-Ile-Gln-Ser-Ile-Lys-Asp-Asp (SEQ ID NO:18);

Ala-Val-Asp-Asn-Lys-Phe-Asn-Met-Gln-Gln-Gln-Ala-Arg-Phe-Tyr-Glu-Ala-Leu-His-Asp-Pro-Asn-Leu-Asn-Glu-Glu-Gln-Arg-Asn-Ala-Lys-Ile-Gln-Ser-Ile-Lys-Asp-Asp (SEQ ID NO: 19);

Ala-Val-Asp-Asn-Lys-Gly-Trp-Met-Arg-Gln-Gln-Ala-Arg-Phe-Tyr-Glu-Ala-Leu-His-Asp-Pro-Asn-Leu-Asn-Glu-Glu-Gln-Arg-Asn-Ala-Lys-Ile-Gln-Ser-Ile-Lys-Asp-Asp (SEQ ID NO:20);

Ala-Val-Asp-Asn-Lys-Phe-Asn-Lys-Glu-Gln-Gln-Ala-Ala-Phe-Tyr-Glu-Ala-Leu-His-Asp-Pro-Asn-Leu-Asn-Glu-Glu-Gln-Arg-Asn-Ala-Lys-Ile-Gln-Ser-Ile-Lys-Asp-Asp (SEQ ID NO:21);

Ala-Val-Asp-Asn-Lys-Phe-Asn-Lys-Glu-Gln-Gln-Ala-Arg-Phe-Tyr-Glu-Ala-Leu-His-Asp-Pro-Asn-Leu-Asn-Glu-

Glu-Gln-Arg-Asn-Ala-Lys-Ile-Lys-Ser-Ile-Arg-Asp-Asp (SEQ ID NO:22);

Ala-Val-Arg-Asn-Gly-Phe-Asn-Met-Gln-Gln-Gln-Ala-Arg-Phe-Tyr-Glu-Ala-Leu-His-Asp-Pro-Asn-Leu-Asn-Glu-Glu-Gln-Arg-Asn-Ala-Lys-Ile-Lys-Ser-Ile-Arg-Asp-Asp (SEQ ID NO:23);

Ala-Val-Ala-Gln-Ser-Phe-Asn-Met-Gln-Gln-Gln-Ala-Arg-Phe-Tyr-Glu-Ala-Leu-His-Asp-Pro-Asn-Leu-Asn-Glu-Glu-Gln-Arg-Asn-Ala-Lys-Ile-Lys-Ser-Ile-Arg-Asp-Asp (SEQ ID NO:24); and Phe-Asn-Met-Gln-Gln-Gln-Ala-Arg-Phe-Tyr-Glu-Ala-Leu-His-Asp-Pro-Asn-Leu-Asn-Glu-Glu-Gln-Arg-Asn-Ala-Lys-Ile-Lys-Ser-Ile-Arg-Asp-Asp (SEQ ID NO:25).

In a preferred embodiment, the invention provides peptides of Formula (Ia) wherein $X_1$ is Ala-Val-$AA_3$-$AA_4$-$AA_5$ (SEQ ID NO:2), $AA_3$ is Ala, $AA_4$ is Gln, and $AA_5$ is Ser.

In another preferred embodiment, the invention provides peptides of Formula (Ia) wherein $X_1$ is Ala-Val-$AA_3$-$AA_4$-$AA_5$ (SEQ ID NO:2), $AA_3$ is Ala, $AA_4$ is Gln, $AA_5$ is Ser, $AA_6$ is Phe, $AA_7$ is Asn, $AA_8$ is Lys, $AA_9$ is Glu, $AA_{12}$ is Asn, $AA_{13}$ is Arg, $AA_{33}$ is Gln, and $AA_{36}$ is Lys.

In yet another aspect, the invention provides peptides of Formula (Ia) wherein $X_1$ is Ala-Val-$AA_3$-$AA_4$-$AA_5$ (SEQ ID NO:2), $AA_3$ is Ala, $AA_4$ is Gln, $AA_5$ is Ser, and $AA_{12}$ is Ala.

In still another aspect, the invention provides peptides of Formula (Ia) wherein $X_1$ is Ala-Val-$AA_3$-$AA_4$-$AA_5$ (SEQ ID NO:2), $AA_3$ is Ala, $AA_4$ is Gln, $AA_5$ is Ser, $AA_6$ is Phe, $AA_7$ is Asn, $AA_8$ is Lys, $AA_9$ is Glu, $AA_{12}$ is Ala, $AA_{13}$ is Arg, $AA_{33}$ is Gln, and $AA_{36}$ is Lys.

In yet another preferred embodiment, the invention provides peptides of Formula (Ia) wherein $AA_6$ is Gly, $AA_7$ is Trp, $AA_8$ is Met, and $AA_9$ is Arg.

In still another preferred embodiment, the invention provides peptides of Formula (Ia) wherein $X_1$ is Ala-Val-$AA_3$-$AA_4$-$AA_5$ (SEQ ID NO:2), $AA_6$ is Gly, $AA_7$ is Trp, $AA_8$ is Met, $AA_9$ is Arg, $AA_3$ is Asp, $AA_4$ is Asn, $AA_5$ is Lys, $AA_2$ is Asn, $AA_{13}$ is Arg, $AA_{33}$ is Gln; and $AA_{36}$ is Lys.

Also encompassed herein are peptides of Formula (Ia) wherein $AA_6$ is Gly, $AA_7$ is Trp, $AA_8$ is Met, $AA_9$ is Arg, and $AA_{12}$ is Ala.

Further encompassed herein are peptides of Formula (Ia) wherein $X_1$ is Ala-Val-$AA_3$-$AA_4$-$AA_5$ (SEQ ID NO:2), $AA_6$ is Gly, $AA_7$ is Trp, $AA_8$ is Met, $AA_9$ is Arg, $AA_3$ is Asp, $AA_4$ is Asn, $AA_5$ is Lys, $AA_{12}$ is Ala, $AA_{13}$ is Arg, $AA_{33}$ is Gln; and $AA_{36}$ is Lys.

In a further preferred embodiment, the invention provides peptides of Formula (Ia) wherein $AA_{12}$ is Arg.

Also preferred are peptides of Formula (Ia) wherein $X_1$ is Ala-Val-$AA_3$-$AA_4$-$AA_5$ (SEQ ID NO:2), $AA_8$ is Lys, $AA_9$ is Glu, $AA_{12}$ is Arg, $AA_3$ is Asp, $AA_4$ is Asn, $AA_5$ is Lys, $AA_6$ is Phe, $AA_7$ is Asn, $AA_{13}$ is Arg, $AA_{33}$ is Gln, and $AA_{36}$ is Lys.

Further encompassed within the scope of the invention are peptides of Formula (Ia) wherein $AA_{12}$ is Ala.

Additionally encompassed within the scope of the invention are peptides of Formula (Ia) wherein $X_1$ is Ala-Val-$AA_3$-$AA_4$-$AA_5$ (SEQ ID NO:2), $AA_8$ is Lys, $AA_9$ is Glu, $AA_{12}$ is Ala, $AA_3$ is Asp, $AA_4$ is Asn, $AA_5$ is Lys, $AA_6$ is Phe, $AA_7$ is Asn, $AA_{13}$ is Arg, $AA_{33}$ is Gln, and $AA_{36}$ is Lys.

In an additional preferred embodiment, the invention provides peptides of Formula (Ia) wherein $AA_{33}$ is Lys and $AA_{36}$ is Arg.

In still another preferred embodiment, the invention provides peptides of Formula (Ia) wherein $X_1$ is Ala-Val-$AA_3$-$AA_4$-$AA_5$ (SEQ ID NO:2), $AA_{33}$ is Lys, $AA_{36}$ is Arg, $AA_3$ is Asp, $AA_4$ is Asn, $AA_5$ is Lys, $AA_6$ is Phe, $AA_7$ is Asn, $AA_8$ is Lys, $AA_9$ is Glu, $AA_{12}$ is Asn, and $AA_{13}$ is Arg.

Further encompassed herein are peptides of Formula (Ia) wherein $AA_{33}$ is Lys, $AA_{36}$ is Arg, and $AA_{12}$ is Ala.

Additionally encompassed herein are peptides of Formula (Ia) wherein $X_1$ is Ala-Val-$AA_3$-$AA_4$-$AA_5$ (SEQ ID NO:2), $AA_{33}$ is Lys, $AA_{36}$ is Arg, $AA_3$ is Asp, $AA_4$ is Asn, $AA_5$ is Lys, $AA_6$ is Phe, $AA_7$ is Asn, $AA_8$ is Lys, $AA_9$ is Glu, $AA_{12}$ is Ala, and $AA_{13}$ is Arg.

In yet another preferred embodiment, the invention provides peptides of Formula (Ia) wherein $X_1$ is Ala-Val-$AA_3$-$AA_4$-$AA_5$ (SEQ ID NO:2), $AA_3$ is Arg, $AA_5$ is Gly, $AA_8$ is Met, $AA_9$ is Gln, $AA_{12}$ is Arg, $AA_{33}$ is Lys, and $AA_{36}$ is Arg.

In a more preferred embodiment, the invention provides peptides of Formula (Ia) wherein $X_1$ is Ala-Val-$AA_3$-$AA_4$-$AA_5$ (SEQ ID NO:2), $AA_3$ is Arg, $AA_5$ is Gly, $AA_8$ is Met, $AA_9$ is Gln, $AA_{12}$ is Arg, $AA_{33}$ is Lys, $AA_{36}$ is Arg, $AA_4$ is Asn, $AA_6$ is Phe, $AA_7$ is Asn, and $AA_{13}$ is Arg.

Also provided herein are peptides of Formula (Ia) wherein $X_1$ is Ala-Val-$AA_3$-$AA_4$-$AA_5$ (SEQ ID NO:2), $AA_3$ is Arg, $AA_5$ is Gly, $AA_8$ is Met, $AA_9$ is Gln, $AA_{12}$ is Ala, $AA_{33}$ is Lys, and $AA_{36}$ is Arg.

Further provided herein are peptides of Formula (Ia) wherein $X_1$ is Ala-Val-$AA_3$-$AA_4$-$AA_5$ (SEQ ID NO:2), $AA_3$ is Arg, $AA_5$ is Gly, $AA_8$ is Met, $AA_9$ is Gln, $AA_{12}$ is Ala, $AA_{33}$ is Lys, $AA_{36}$ is Arg, $AA_4$ is Asn, $AA_6$ is Phe, $AA_7$ is Asn, and $AA_{13}$ is Arg.

In an additional preferred embodiment, the invention provides peptides of Formula (Ia) wherein $X_1$ is Ala-Val-$AA_3$-$AA_4$-$AA_5$ (SEQ ID NO:2), $AA_3$ is Ala, $AA_4$ is Gln, $AA_5$ is Ser, $AA_8$ is Met, $AA_9$ is Gln, $AA_{12}$ is Arg, $AA_{33}$ is Lys, and $AA_{36}$ is Arg.

In a more preferred embodiment, the invention provides peptides of Formula (Ia) wherein $X_1$ is Ala-Val-$AA_3$-$AA_4$-$AA_5$ (SEQ ID NO:2), $AA_3$ is Ala, $AA_4$ is Gln, $AA_5$ is Ser, $AA_8$ is Met, $AA_9$ is Gln, $AA_{12}$ is Arg, $AA_{33}$ is Lys, $AA_{36}$ is Arg, $AA_6$ is Phe, $AA_7$ is Asn, and $AA_{13}$ is Arg.

Additionally provided herein are peptides of Formula (Ia) wherein $X_1$ is Ala-Val-$AA_3$-$AA_4$-$AA_5$ (SEQ ID NO:2), $AA_3$ is Ala, $AA_4$ is Gln, $AA_5$ is Ser, $AA_8$ is Met, $AA_9$ is Gln, $AA_{12}$ is Ala, $AA_{33}$ is Lys, and $AA_{36}$ is Arg.

In another embodiment, the invention provides peptides of Formula (Ia) wherein $X_1$ is Ala-Val-$AA_3$-$AA_4$-$AA_5$ (SEQ ID NO:2), $AA_3$ is Ala, $AA_4$ is Gln, $AA_5$ is Ser, $AA_8$ is Met, $AA_9$ is Gln, $AA_{12}$ is Ala, $AA_{33}$ is Lys, $AA_{36}$ is Arg, $AA_6$ is Phe, $AA_7$ is Asn, and $AA_{13}$ is Arg.

In a particularly preferred embodiment, the invention provides peptides of Formula (Ia) wherein $X_1$ is absent, $AA_8$ is Met, $AA_9$ is Gln, $AA_{12}$ is Arg, $AA_{33}$ is Lys, and $AA_{36}$ is Arg.

In an even more preferred embodiment, the invention provides peptides of Formula (Ia) wherein $X_1$ is absent, $AA_8$ is Met, $AA_9$ is Gln, $AA_{12}$ is Arg, $AA_{33}$ is Lys, $AA_{36}$ is Arg, $AA_6$ is Phe, $AA_7$ is Asn, and $AA_{13}$ is Arg.

In yet another embodiment, the invention provides peptides of Formula (Ia) wherein $X_1$ is absent, $AA_8$ is Met, $AA_9$ is Gln, $AA_{12}$ is Ala, $AA_{33}$ is Lys, and $AA_{36}$ is Arg.

In still another embodiment, the invention provides peptides of Formula (Ia) wherein $X_1$ is absent, $AA_8$ is Met, $AA_9$ is Gln, $AA_{12}$ is Ala, $AA_{33}$ is Lys, $AA_{36}$ is Arg, $AA_6$ is Phe, $AA_7$ is Asn, and $AA_{13}$ is Arg.

In another aspect, the invention provides Z domain variant peptides that are conformationally restrained by an intramolecular disulfide bond in order to improve the structural stability of the variant peptides. It was discovered that the substitution of a cysteine residue at amino acid position 10 and the addition of a cysteine at the C-terminus of the Z domain variants described herein followed by cyclization of such peptides results in the formation of variants which mimic the native helicity of the full-length, wild type Z domain. The cyclization of the Z domain variant peptides was also found to increase the IgG-binding activity of the variant peptides. Accordingly, the invention provides cyclized Z domain variant peptides represented by Formula (II):

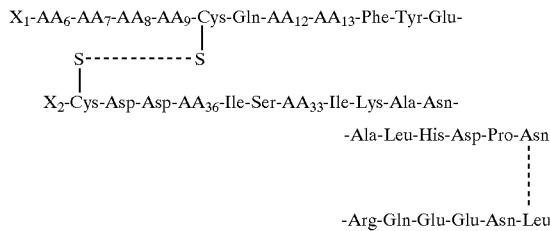

(II)
(SEQ ID NO:3)

where
$X_1$ is selected from the group consisting of H, $C_1$–$C_6$ alkanoyl, and Z-Ala-Val-$AA_3$-$AA_4$-$AA_5$ (SEQ ID NO:2);
  where
  Z is selected from the group consisting of H and $C_1$–$C_6$ alkanoyl;
  $AA_3$ is selected from the group consisting of Asp, Arg, and Ala;
  $AA_4$ is selected from the group consisting of Asn and Gln; and
  $AA_5$ is selected from the group consisting of Lys, Gly, and Ser;
$AA_6$ is selected from the group consisting of Phe and Gly;
$AA_7$ is selected from the group consisting of Asn and Trp;
$AA_8$ is selected from the group consisting of Lys and Met;
$AA_9$ is selected from the group consisting of Glu, Gln, and Arg;
$AA_{12}$ is selected from the group consisting of Asn, Ala, and Arg;
$AA_{13}$ is selected from the group consisting of Ala and Arg;
$AA_{33}$ is selected from the group consisting of Gln and Lys;
$AA_{36}$ is selected from the group consisting of Lys and Arg; and
$X_2$ is selected from the group consisting of $OR_1$ and $NR_1R_2$ where $R_1$ and $R_2$ are independently selected from the group consisting of H, $C_1$–$C_6$alkyl, $C_6$–$C_{12}$aryl and $C_6$–$C_{12}$aryl-$C_1$–$C_6$alkyl.

In one embodiment, the invention provides peptides of Formula (II) wherein $X_1$ is Z-Ala-Val-$AA_3$-$AA_4$-$AA_5$ (SEQ ID NO:2), $AA_3$ is Arg, and $AA_5$ is Gly.

In another embodiment, the invention provides peptides of Formula (II) wherein $X_1$ is Z-Ala-Val-$AA_3$-$AA_4$-$AA_5$ (SEQ ID NO:2), $AA_3$ is Arg, $AA_5$ is Gly, $AA_4$ is Asn, $AA_6$ is Phe, $AA_7$ is Asn, $AA_8$ is Lys, $AA_9$ is Glu, $AA_{12}$ is Asn, $AA_{13}$ is Arg, $AA_{33}$ is Gln, and $AA_{36}$ is Lys.

In yet another embodiment, the invention provides peptides of Formula (II) wherein $X_1$ is Z-Ala-Val-$AA_3$-$AA_4$-$AA_5$ (SEQ ID NO:2), $AA_3$ is Arg, $AA_5$ is Gly, and $AA_{12}$ is Ala.

Further provided herein are peptides of Formula (II) wherein $X_1$ is Z-Ala-Val-$AA_3$-$AA_4$-$AA_5$ (SEQ ID NO:2), $AA_3$ is Arg, $AA_5$ is Gly, $AA_4$ is Asn, $AA_6$ is Phe, $AA_7$ is Asn, $AA_8$ is Lys, $AA_9$ is Glu, $AA_{12}$ is Ala, $AA_{13}$ is Arg, $AA_{33}$ is Gln, and $AA_{36}$ is Lys.

In still another embodiment, the invention provides peptides of Formula (II) wherein $AA_8$ is Met and $AA_9$ is Gln.

Also provided herein are peptides of Formula (II) wherein $AA_8$ is Met, $AA_9$ is Gln, $X_1$ is Z-Ala-Val-$AA_3$-$AA_4$-$AA_5$ (SEQ ID NO:2), $AA_3$ is Asp, $AA_4$ is Asn, $AA_5$ is Lys, $AA_6$ is Phe, $AA_7$ is Asn, $AA_{12}$ is Asn, $AA_{13}$ is Arg, $AA_{33}$ is Gln, and $AA_{36}$ is Lys.

Additionally provided herein are peptides of Formula (II) wherein $AA_8$ is Met, $AA_9$ is Gln, and $AA_{12}$ is Ala.

In a further aspect, the invention provides peptides of Formula (II) wherein $AA_8$ is Met, $AA_9$ is Gln, $X_1$ is Z-Ala-Val-$AA_3$-$AA_4$-$AA_5$ (SEQ ID NO:2), $AA_3$ is Asp, $AA_4$ is Asn, $AA_5$ is Lys, $AA_6$ is Phe, $AA_7$ is Asn, $AA_{12}$ is Ala, $AA_{13}$ is Arg, $AA_{33}$ is Gln, and $AA_{36}$ is Lys.

In an additional embodiment, the invention provides peptides of Formula (II) wherein $AA_{12}$ is Arg and $AA_{13}$ is Ala.

In a further embodiment, the invention provides peptides of Formula (II) wherein $AA_{12}$ is Arg, $AA_{13}$ is Ala, $X_1$ is Z-Ala-Val-$AA_3$-$AA_4$-$AA_5$ (SEQ ID NO:2), $AA_3$ is Asp, $AA_4$ is Asn, $AA_5$ is Lys, $AA_6$ is Phe, $AA_7$ is Asn, $AA_8$ is Lys, $AA_9$ is Glu, $AA_{33}$ is Gln, and $AA_{36}$ is Lys.

Also encompassed within the scope of the invention are peptides of Formula (II) wherein $AA_{12}$ is Ala and $AA_{13}$ is Ala.

Further encompassed within the scope of the invention are peptides of Formula (II) wherein $AA_{12}$ is Ala, $AA_{13}$ is Ala, $X_1$ is Z-Ala-Val-$AA_3$-$AA_4$-$AA_5$ (SEQ ID NO:2), $AA_3$ is Asp, $AA_4$ is Asn, $AA_5$ is Lys, $AA_6$ is Phe, $AA_7$ is Asn, $AA_8$ is Lys, $AA_9$ is Glu, $AA_{33}$ is Gln; and $AA_{36}$ is Lys.

In yet another aspect, the invention provides a cyclized Z domain variant peptide selected from the group consisting of

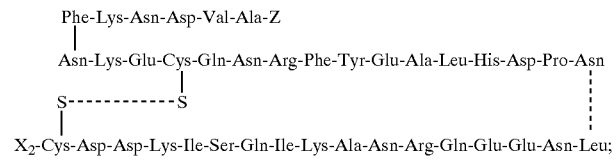

(SEQ ID NO:26)

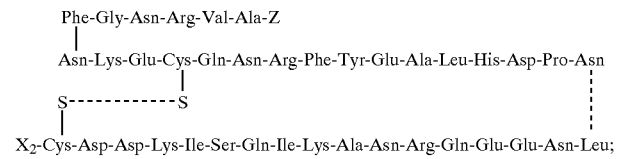

(SEQ ID NO:27)

-continued (SEQ ID NO:28)
```
         Phe-Ser-Gln-Ala-Val-Ala-Z
         |
         Asn-Lys-Glu-Cys-Gln-Asn-Arg-Phe-Tyr-Glu-Ala-Leu-His-Asp-Pro-Asn
                      |                                              |
         S-----------S                                               |
         |                                                           |
X₂-Cys-Asp-Asp-Lys-Ile-Ser-Gln-Ile-Lys-Ala-Asn-Arg-Gln-Glu-Glu-Asn-Leu;
```

(SEQ ID NO:29)
```
         Phe-Lys-Asn-Asp-Val-Ala-Z
         |
         Asn-Met-Gln-Cys-Gln-Asn-Arg-Phe-Tyr-Glu-Ala-Leu-His-Asp-Pro-Asn
                      |                                              |
         S-----------S                                               |
         |                                                           |
X₂-Cys-Asp-Asp-Lys-Ile-Ser-Gln-Ile-Lys-Ala-Asn-Arg-Gln-Glu-Glu-Asn-Leu;
```

(SEQ ID NO:30)
```
         Gly-Lys-Asn-Asp-Val-Ala-Z
         |
         Trp-Met-Arg-Cys-Gln-Asn-Arg-Phe-Tyr-Glu-Ala-Leu-His-Asp-Pro-Asn
                      |                                              |
         S-----------S                                               |
         |                                                           |
X₂-Cys-Asp-Asp-Lys-Ile-Ser-Gln-Ile-Lys-Ala-Asn-Arg-Gln-Glu-Glu-Asn-Leu;
```

(SEQ ID NO:31)
```
         Phe-Lys-Asn-Asp-Val-Ala-Z
         |
         Asn-Lys-Glu-Cys-Gln-Arg-Arg-Phe-Tyr-Glu-Ala-Leu-His-Asp-Pro-Asn
                      |                                              |
         S-----------S                                               |
         |                                                           |
X₂-Cys-Asp-Asp-Lys-Ile-Ser-Gln-Ile-Lys-Ala-Asn-Arg-Gln-Glu-Glu-Asn-Leu;
```

(SEQ ID NO:32)
```
         Phe-Lys-Asn-Asp-Val-Ala-Z
         |
         Asn-Lys-Glu-Cys-Gln-Arg-Ala-Phe-Tyr-Glu-Ala-Leu-His-Asp-Pro-Asn
                      |                                              |
         S-----------S                                               |
         |                                                           |
X₂-Cys-Asp-Asp-Lys-Ile-Ser-Gln-Ile-Lys-Ala-Asn-Arg-Gln-Glu-Glu-Asn-Leu;
```

(SEQ ID NO:33)
```
         Phe-Lys-Asn-Asp-Val-Ala-Z
         |
         Asn-Lys-Glu-Cys-Gln-Asn-Arg-Phe-Tyr-Glu-Ala-Leu-His-Asp-Pro-Asn
                      |                                              |
         S-----------S                                               |
         |                                                           |
X₂-Cys-Asp-Asp-Arg-Ile-Ser-Lys-Ile-Lys-Ala-Asn-Arg-Gln-Glu-Glu-Asn-Leu;
```

(SEQ ID NO:34)
```
         Phe-Gly-Asn-Arg-Val-Ala-Z
         |
         Asn-Met-Gln-Cys-Gln-Arg-Arg-Phe-Tyr-Glu-Ala-Leu-His-Asp-Pro-Asn
                      |                                              |
         S-----------S                                               |
         |                                                           |
X₂-Cys-Asp-Asp-Arg-Ile-Ser-Lys-Ile-Lys-Ala-Asn-Arg-Gln-Glu-Glu-Asn-Leu;
```

(SEQ ID NO:35)
```
         Phe-Ser-Gln-Ala-Val-Ala-Z
         |
         Asn-Met-Gln-Cys-Gln-Arg-Arg-Phe-Tyr-Glu-Ala-Leu-His-Asp-Pro-Asn
                      |                                              |
         S-----------S                                               |
         |                                                           |
X₂-Cys-Asp-Asp-Arg-Ile-Ser-Lys-Ile-Lys-Ala-Asn-Arg-Gln-Glu-Glu-Asn-Leu;
```
and (SEQ ID NO:36)
```
X₁-Phe-Asn-Met-Gln-Cys-Gln-Arg-Arg-Phe-Tyr-Glu-Ala-Leu-His-Asp-Pro-Asn
                  |                                              |
         S-----------S                                            |
         |                                                        |
X₂-Cys-Asp-Asp-Arg-Ile-Ser-Lys-Ile-Lys-Ala-Asn-Arg-Gln-Glu-Glu-Asn-Leu;
``` where $X_1$ is selected from the group consisting of H and $C_1$–$C_6$alkanoyl;

Z is selected from the group consisting of H and $C_1$–$C_6$alkanoyl; and $X_2$ is selected from the group consisting of $OR_1$ and $NR_1R_2$ where $R_1$ and $R_2$ are independently selected from the group consisting of H, $C_1$–$C_6$alkyl, $C_6$–$C_{12}$aryl and $C_6$–$C_{12}$aryl-$C_1$–$C_6$alkyl.

In still another aspect, the invention provides a cyclized Z domain variant peptide selected from the group consisting of

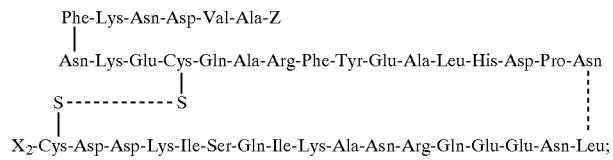
(SEQ ID NO:37)

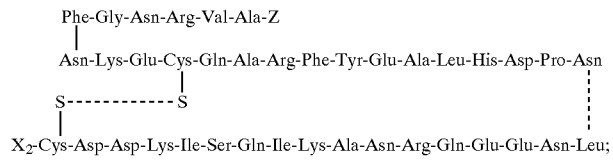
(SEQ ID NO:38)

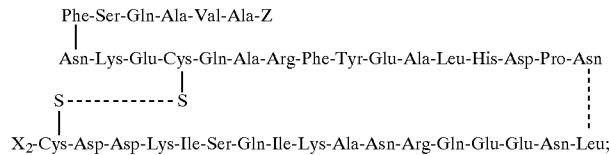
(SEQ ID NO:39)

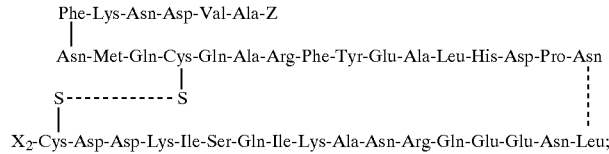
(SEQ ID NO:40)

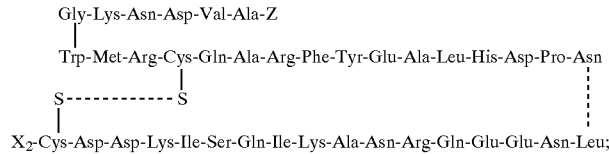
(SEQ ID NO:41)

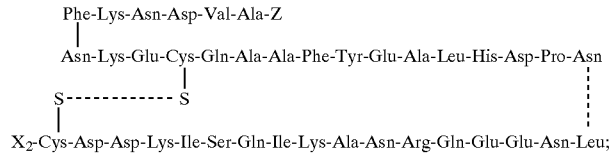
(SEQ ID NO:42)

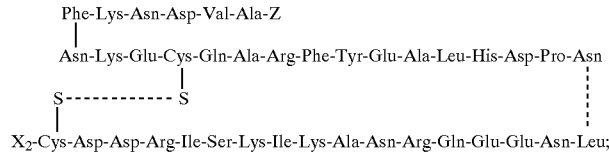
(SEQ ID NO:43)

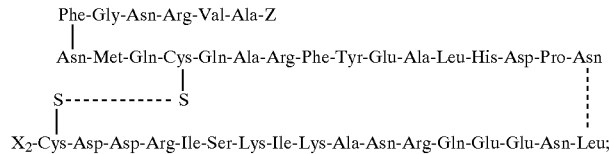
(SEQ ID NO:44)

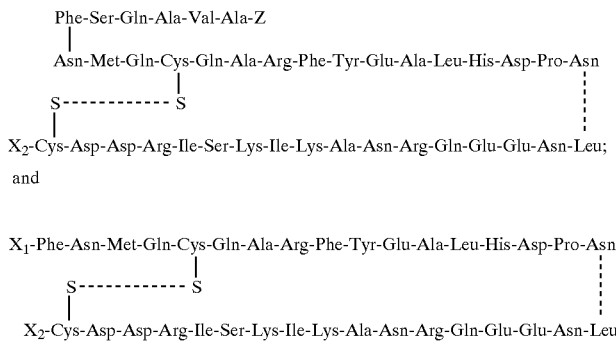

where
X$_1$ is selected from the group consisting of H and C$_1$–C$_6$alkanoyl;
Z is selected from the group consisting of H and C$_1$–C$_6$ alkanoyl; and
X$_2$ is selected from the group consisting of OR$_1$ and NR$_1$R$_2$ where R$_1$ and R$_2$ are independently selected from the group consisting of H, C$_1$–C$_6$ alkyl, C$_6$–C$_{12}$aryl and C$_6$–C$_{12}$aryl-C$_1$–C$_6$alkyl.

In a preferred embodiment, the invention provides peptides of Formula (II) wherein X$_1$ is Z-Ala-Val-AA$_3$-AA$_4$-AA$_5$ (SEQ ID NO:2), AA$_3$ is Ala, AA$_4$ is Gln, and AA$_5$ is Ser.

In another preferred embodiment, the invention provides peptides of Formula (II) wherein X$_1$ is Z-Ala-Val-AA$_3$-AA$_4$-AA$_5$ (SEQ ID NO:2), AA$_3$ is Ala, AA$_4$ is Gln, AA$_5$ is Ser, AA$_6$ is Phe, AA$_7$ is Asn, AA$_8$ is Lys, AA$_9$ is Glu, AA$_{12}$ is Asn, AA$_{13}$ is Arg, AA$_{33}$ is Gln, and AA$_{36}$ is Lys.

In yet another aspect, the invention provides peptides of Formula (II) wherein X$_1$ is Z-Ala-Val-AA$_3$-AA$_4$-AA$_5$ (SEQ ID NO:2), AA$_3$ is Ala, AA$_4$ is Gln, AA$_5$ is Ser, and AA$_{12}$ is Ala.

In still another aspect, the invention provides peptides of Formula (II) wherein X$_1$ is Z-Ala-Val-AA$_3$-AA$_4$-AA$_5$ (SEQ ID NO:2), AA$_3$ is Ala, AA$_4$ is Gln, AA$_5$ is Ser, AA$_6$ is Phe, AA$_7$ is Asn, AA$_8$ is Lys, AA$_9$ is Glu, AA$_{12}$ is Ala, AA$_{13}$ is Arg, AA$_{33}$ is Gln, and AA$_{36}$ is Lys.

In yet another preferred embodiment, the invention provides peptides of Formula (II) wherein AA$_6$ is Gly, AA$_7$ is Trp, AA$_8$ is Met, and AA$_9$ is Arg.

In still another preferred embodiment, the invention provides peptides of Formula (II) wherein X$_1$ is Z-Ala-Val-AA$_3$-AA$_4$-AA$_5$ (SEQ ID NO:2), AA$_6$ is Gly, AA$_7$ is Trp, AA$_8$ is Met, AA$_9$ is Arg, AA$_3$ is Asp, AA$_4$ is Asn, AA$_5$ is Lys, AA$_{12}$ is Asn, AA$_{13}$ is Arg, AA$_{33}$ is Gln; and AA$_{36}$ is Lys.

Also encompassed herein are peptides of Formula (II) wherein AA$_6$ is Gly, AA$_7$ is Trp, AA$_8$ is Met, AA$_9$ is Arg, and AA$_{12}$ is Ala.

Further encompassed herein are peptides of Formula (II) wherein X$_1$ is Z-Ala-Val-AA$_3$-AA$_4$-AA$_5$ (SEQ ID NO:2), AA$_6$ is Gly, AA$_7$ is Trp, AA$_8$ is Met, AA$_9$ is Arg, AA$_3$ is Asp, AA$_4$ is Asn, AA$_5$ is Lys, AA$_{12}$ is Ala, AA$_{13}$ is Arg, AA$_{33}$ is Gln; and AA$_{36}$ is Lys.

In a further preferred embodiment, the invention provides peptides of Formula (II) wherein AA$_{12}$ is Arg.

Also preferred are peptides of Formula (II) wherein X$_1$ is Z-Ala-Val-AA$_3$-AA$_4$-AA$_5$ (SEQ ID NO:2), AA$_{12}$ is Arg, AA$_3$ is Asp, AA$_4$ is Asn, AA$_5$ is Lys, AA$_6$ is Phe, AA$_7$ is Asn, AA$_8$ is Lys, AA$_9$ is Glu, AA$_{13}$ is Arg, AA$_{33}$ is Gln, and AA$_{36}$ is Lys.

Further encompassed within the scope of the invention are peptides of Formula (II) wherein AA$_{12}$ is Ala.

Additionally encompassed within the scope of the invention are peptides of Formula (II) wherein X$_1$ is Z-Ala-Val-AA$_3$-AA$_4$-AA$_5$ (SEQ ID NO:2), AA$_{12}$ is Ala, AA$_3$ is Asp, AA$_4$ is Asn, AA$_5$ is Lys, AA$_6$ is Phe, AA$_7$ is Asn, AA$_8$ is Lys, AA$_9$ is Glu, AA$_{13}$ is Arg, AA$_{33}$ is Gln, and AA$_{36}$ is Lys.

In an additional preferred embodiment, the invention provides peptides of Formula (II) wherein AA$_{33}$ is Lys and AA$_{36}$ is Arg.

In still another preferred embodiment, the invention provides peptides of Formula (II) wherein X$_1$ is Z-Ala-Val-AA$_3$-AA$_4$-AA$_5$ (SEQ ID NO:2), AA$_{33}$ is Lys, AA$_{36}$ is Arg, AA$_3$ is Asp, AA$_4$ is Asn, AA$_5$ is Lys, AA$_6$ is Phe, AA$_7$ is Asn, AA$_8$ is Lys, AA$_9$ is Glu, AA$_{12}$ is Asn, and AA$_{13}$ is Arg.

Further encompassed herein are peptides of Formula (II) wherein AA$_{33}$ is Lys, AA$_{36}$ is Arg, and AA$_{12}$ is Ala.

Additionally encompassed herein are peptides of Formula (II) wherein X$_1$ is Z-Ala-Val-AA$_3$-AA$_4$-AA$_5$ (SEQ ID NO:2), AA$_{33}$ is Lys, AA$_{36}$ is Arg, AA$_3$ is Asp, AA$_4$ is Asn, AA$_5$ is Lys, AA$_6$ is Phe, AA$_7$ is Asn, AA$_8$ is Lys, AA$_9$ is Glu, AA$_{12}$ is Ala, and AA$_{13}$ is Arg.

In yet another preferred embodiment, the invention provides peptides of Formula (II) wherein X$_1$ is Z-Ala-Val-AA$_3$-AA$_4$-AA$_5$ (SEQ ID NO:2), AA$_3$ is Arg, AA$_5$ is Gly, AA$_8$ is Met, AA$_9$ is Gln, AA$_{12}$ is Arg, AA$_{33}$ is Lys, and AA$_{36}$ is Arg.

In a more preferred embodiment, the invention provides peptides of Formula (II) wherein X$_1$ is Z-Ala-Val-AA$_3$-AA$_4$-AA$_5$ (SEQ ID NO:2), AA$_3$ is Arg, AA$_5$ is Gly, AA$_8$ is Met, AA$_9$ is Gln, AA$_{12}$ is Arg, AA$_{33}$ is Lys, AA$_{36}$ is Arg, AA$_4$ is Asn, AA$_6$ is Phe, AA$_7$ is Asn, and AA$_{13}$ is Arg.

Also provided herein are peptides of Formula (II) wherein X$_1$ is Z-Ala-Val-AA$_3$-AA$_4$-AA$_5$ (SEQ ID NO:2), AA$_3$ is Arg, AA$_5$ is Gly, AA$_8$ is Met, AA$_9$ is Gln, AA$_{12}$ is Ala, AA$_{33}$ is Lys, and AA$_{36}$ is Arg.

Further provided herein are peptides of Formula (II) wherein X$_1$ is Z-Ala-Val-AA$_3$-AA$_4$-AA$_5$ (SEQ ID NO:2), AA$_3$ is Arg, AA$_5$ is Gly, AA$_8$ is Met, AA$_9$ is Gln, AA$_{12}$ is Ala, AA$_{33}$ is Lys, AA$_{36}$ is Arg, AA$_4$ is Asn, AA$_6$ is Phe, AA$_7$ is Asn, and AA$_{13}$ is Arg.

In an additional preferred embodiment, the invention provides peptides of Formula (II) wherein X$_1$ is Z-Ala-Val-AA$_3$-AA$_4$-AA$_5$ (SEQ ID NO:2), AA$_3$ is Ala, AA$_4$ is Gln, AA$_5$ is Ser, AA$_8$ is Met, AA$_9$ is Gln, AA$_{12}$ is Arg, AA$_{33}$ is Lys, and AA$_{36}$ is Arg.

In a more preferred embodiment, the invention provides peptides of Formula (II) wherein X$_1$ is Z-Ala-Val-AA$_3$-AA$_4$-AA$_5$ (SEQ ID NO:2), AA$_3$ is Ala, AA$_4$ is Gln, AA$_5$ is Ser, AA$_8$ is Met, AA$_9$ is Gln, AA$_{12}$ is Arg, AA$_{33}$ is Lys, AA$_{36}$ is Arg, AA$_6$ is Phe, AA$_7$ is Asn, and AA$_{13}$ is Arg.

Additionally provided herein are peptides of Formula (II) wherein $X_1$ is Z-Ala-Val-$AA_3$-$AA_4$-$AA_5$ (SEQ ID NO:2), $AA_3$ is Ala, $AA_4$ is Gln, $AA_5$ is Ser, $AA_8$ is Met, $AA_9$ is Gln, $AA_{12}$ is Ala, $AA_{33}$ is Lys, and $AA_{36}$ is Arg.

In another embodiment, the invention provides peptides of Formula (II) wherein $X_1$ is Z-Ala-Val-$AA_3$-$AA_4$-$AA_5$ (SEQ ID NO:2), $AA_3$ is Ala, $AA_4$ is Gln, $AA_5$ is Ser, $AA_8$ is Met, $AA_9$ is Gln, $AA_{12}$ is Ala, $AA_{33}$ is Lys, $AA_{36}$ is Arg, $AA_6$ is Phe, $AA_7$ is Asn, and $AA_{13}$ is Arg.

In a particularly preferred embodiment, the invention provides peptides of Formula (II) wherein $X_1$ is H or $C_1$–$C_6$ alkanoyl, $AA_8$ is Met, $AA_9$ is Gln, $AA_{12}$ is Arg, $AA_{33}$ is Lys, and $AA_{36}$ is Arg.

In an even more preferred embodiment, the invention provides peptides of Formula (II) wherein $X_1$ is H or $C_1$–$C_6$ alkanoyl, $AA_8$ is Met, $AA_9$ is Gln, $AA_{12}$ is Arg, $AA_{33}$ is Lys, $AA_{36}$ is Arg, $AA_6$ is Phe, $AA_7$ is Asn, and $AA_{13}$ is Arg.

In yet another embodiment, the invention provides peptides of Formula (II) wherein $X_1$ is H or $C_1$–$C_6$ alkanoyl, $AA_8$ is Met, $AA_9$ is Gln, $AA_{12}$ is Ala, $AA_{33}$ is Lys, and $AA_{36}$ is Arg.

In still another embodiment, the invention provides peptides of Formula (II) wherein $X_1$ is H or $C_1$–$C_6$ alkanoyl, $AA_8$ is Met, $AA_9$ is Gln, $AA_{12}$ is Ala, $AA_{33}$ is Lys, $AA_{36}$ is Arg, $AA_6$ is Phe, $AA_7$ is Asn, and $AA_{13}$ is Arg.

In another embodiment, the invention provides Z domain variant peptides represented by Formula (IIa):

In one embodiment, the invention provides peptides of Formula (IIa) wherein $X_1$ is Ala-Val-$AA_3$-$AA_4$-$AA_5$ (SEQ ID NO:2), $AA_3$ is Arg, and $AA_5$ is Gly.

In another embodiment, the invention provides peptides of Formula (IIa) wherein $X_1$ is Ala-Val-$AA_3$-$AA_4$-$AA_5$ (SEQ ID NO:2), $AA_3$ is Arg, $AA_5$ is Gly, $AA_4$ is Asn, $AA_6$ is Phe, $AA_7$ is Asn, $AA_8$ is Lys, $AA_9$ is Glu, $AA_{12}$ is Asn, $AA_{13}$ is Arg, $AA_{33}$ is Gln, and $AA_{36}$ is Lys.

In yet another embodiment, the invention provides peptides of Formula (IIa) wherein $X_1$ is Ala-Val-$AA_3$-$AA_4$-$AA_5$ (SEQ ID NO:2), $AA_3$ is Arg, $AA_5$ is Gly, and $AA_{12}$ is Ala.

Further provided herein are peptides of Formula (IIa) wherein $X_1$ is Ala-Val-$AA_3$-$AA_4$-$AA_5$ (SEQ ID NO:2), $AA_3$ is Arg, $AA_5$ is Gly, $AA_4$ is Asn, $AA_6$ is Phe, $AA_7$ is Asn, $AA_8$ is Lys, $AA_9$ is Glu, $AA_{12}$ is Ala, $AA_{13}$ is Arg, $AA_{33}$ is Gln, and $AA_{36}$ is Lys.

In still another embodiment, the invention provides peptides of Formula (IIa) wherein $AA_8$ is Met and $AA_9$ is Gln.

Also provided herein are peptides of Formula (IIa) wherein $AA_8$ is Met, $AA_9$ is Gln, $X_1$ is Ala-Val-$AA_3$-$AA_4$-$AA_5$ (SEQ ID NO:2), $AA_3$ is Asp, $AA_4$ is Asn, $AA_5$ is Lys, $AA_6$ is Phe, $AA_7$ is Asn, $AA_{12}$ is Asn, $AA_{13}$ is Arg, $AA_{33}$ is Gln, and $AA_{36}$ is Lys.

Additionally provided herein are peptides of Formula (IIa) wherein $AA_8$ is Met, $AA_9$ is Gln, and $AA_{12}$ is Ala.

In a further aspect, the invention provides peptides of Formula (IIa) wherein $AA_8$ is Met, $AA_9$ is Gln, $X_1$ is

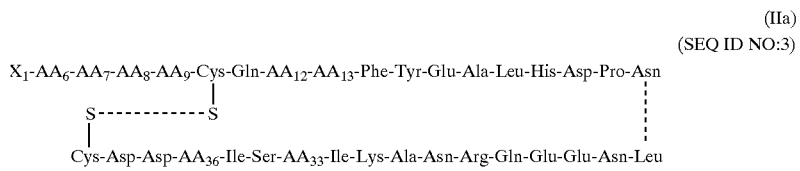

(IIa)
(SEQ ID NO:3)

where $X_1$ is absent or is Ala-Val-$AA_3$-$AA_4$-$AA_5$ (SEQ ID NO:2);

where $AA_3$ is selected from the group consisting of Asp, Arg, and Ala;

$AA_4$ is selected from the group consisting of Asn and Gln; and $AA_5$ is selected from the group consisting of Lys, Gly, and Ser;

$AA_6$ is selected from the group consisting of Phe and Gly;

$AA_7$ is selected from the group consisting of Asn and Trp;

$AA_8$ is selected from the group consisting of Lys and Met;

$AA_9$ is selected from the group consisting of Glu, Gln, and Arg;

$AA_{12}$ is selected from the group consisting of Asn, Ala, and Arg;

$AA_{13}$ is selected from the group consisting of Ala and Arg;

$AA_{33}$ is selected from the group consisting of Gln and Lys; and $AA_{36}$ is selected from the group consisting of Lys and Arg.

Ala-Val-$AA_3$-$AA_4$-$AA_5$ (SEQ ID NO:2), $AA_3$ is Asp, $AA_4$ is Asn, $AA_5$ is Lys, $AA_6$ is Phe, $AA_7$ is Asn, $AA_{12}$ is Ala, $AA_{13}$ is Arg, $AA_{33}$ is Gln, and $AA_{36}$ is Lys.

In an additional embodiment, the invention provides peptides of Formula (IIa) wherein $AA_{12}$ is Arg and $AA_{13}$ is Ala.

In a further embodiment, the invention provides peptides of Formula (IIa) wherein $AA_{12}$ is Arg, $AA_{13}$ is Ala, $X_1$ is Ala-Val-$AA_3$-$AA_4$-$AA_5$ (SEQ ID NO:2), $AA_3$ is Asp, $AA_4$ is Asn, $AA_5$ is Lys, $AA_6$ is Phe, $AA_7$ is Asn, $AA_8$ is Lys, $AA_9$ is Glu, $AA_{33}$ is Gln, and $AA_{36}$ is Lys.

Also encompassed within the scope of the invention are peptides of Formula (IIa) wherein $AA_{12}$ is Ala and $AA_{13}$ is Ala.

Further encompassed within the scope of the invention are peptides of Formula (IIa) wherein $AA_{12}$ is Ala, $AA_{13}$ is Ala, $X_1$ is Ala-Val-$AA_3$-$AA_4$-$AA_5$ (SEQ ID NO:2), $AA_3$ is Asp, $AA_4$ is Asn, $AA_5$ is Lys, $AA_6$ is Phe, $AA_7$ is Asn, $AA_8$ is Lys, $AA_9$ is Glu, $AA_{33}$ is Gln; and $AA_{36}$ is Lys.

In yet another aspect, the invention provides a cyclized Z domain variant peptide selected from the group consisting of (SEQ ID NO:26)
```
    Phe-Lys-Asn-Asp-Val-Ala
    |
    Asn-Lys-Glu-Cys-Gln-Asn-Arg-Phe-Tyr-Glu-Ala-Leu-His-Asp-Pro-Asn
              |
  S-----------S                                                  :
  |                                                              :
  Cys-Asp-Asp-Lys-Ile-Ser-Gln-Ile-Lys-Ala-Asn-Arg-Gln-Glu-Glu-Asn-Leu;
```

(SEQ ID NO:27)
```
    Phe-Gly-Asn-Arg-Val-Ala
    |
    Asn-Lys-Glu-Cys-Gln-Asn-Arg-Phe-Tyr-Glu-Ala-Leu-His-Asp-Pro-Asn
              |
  S-----------S                                                  :
  |                                                              :
  Cys-Asp-Asp-Lys-Ile-Ser-Gln-Ile-Lys-Ala-Asn-Arg-Gln-Glu-Glu-Asn-Leu;
```

(SEQ ID NO:28)
```
    Phe-Ser-Gln-Ala-Val-Ala
    |
    Asn-Lys-Glu-Cys-Gln-Asn-Arg-Phe-Tyr-Glu-Ala-Leu-His-Asp-Pro-Asn
              |
  S-----------S                                                  :
  |                                                              :
  Cys-Asp-Asp-Lys-Ile-Ser-Gln-Ile-Lys-Ala-Asn-Arg-Gln-Glu-Glu-Asn-Leu;
```

(SEQ ID NO:29)
```
    Phe-Lys-Asn-Asp-Val-Ala
    |
    Asn-Met-Gln-Cys-Gln-Asn-Arg-Phe-Tyr-Glu-Ala-Leu-His-Asp-Pro-Asn
              |
  S-----------S                                                  :
  |                                                              :
  Cys-Asp-Asp-Lys-Ile-Ser-Gln-Ile-Lys-Ala-Asn-Arg-Gln-Glu-Glu-Asn-Leu;
```

(SEQ ID NO:30)
```
    Gly-Lys-Asn-Asp-Val-Ala
    |
    Trp-Met-Arg-Cys-Gln-Asn-Arg-Phe-Tyr-Glu-Ala-Leu-His-Asp-Pro-Asn
              |
  S-----------S                                                  :
  |                                                              :
  Cys-Asp-Asp-Lys-Ile-Ser-Gln-Ile-Lys-Ala-Asn-Arg-Gln-Glu-Glu-Asn-Leu;
```

(SEQ ID NO:31)
```
    Phe-Lys-Asn-Asp-Val-Ala
    |
    Asn-Lys-Glu-Cys-Gln-Arg-Arg-Phe-Tyr-Glu-Ala-Leu-His-Asp-Pro-Asn
              |
  S-----------S                                                  :
  |                                                              :
  Cys-Asp-Asp-Lys-Ile-Ser-Gln-Ile-Lys-Ala-Asn-Arg-Gln-Glu-Glu-Asn-Leu;
```

(SEQ ID NO:32)
```
    Phe-Lys-Asn-Asp-Val-Ala
    |
    Asn-Lys-Glu-Cys-Gln-Arg-Ala-Phe-Tyr-Glu-Ala-Leu-His-Asp-Pro-Asn
              |
  S-----------S                                                  :
  |                                                              :
  Cys-Asp-Asp-Lys-Ile-Ser-Gln-Ile-Lys-Ala-Asn-Arg-Gln-Glu-Glu-Asn-Leu;
```

(SEQ ID NO:33)
```
    Phe-Lys-Asn-Asp-Val-Ala
    |
    Asn-Lys-Glu-Cys-Gln-Asn-Arg-Phe-Tyr-Glu-Ala-Leu-His-Asp-Pro-Asn
              |
  S-----------S                                                  :
  |                                                              :
  Cys-Asp-Asp-Arg-Ile-Ser-Lys-Ile-Lys-Ala-Asn-Arg-Gln-Glu-Glu-Asn-Leu;
```

(SEQ ID NO:34)
```
    Phe-Gly-Asn-Arg-Val-Ala
    |
    Asn-Met-Gln-Cys-Gln-Arg-Arg-Phe-Tyr-Glu-Ala-Leu-His-Asp-Pro-Asn
              |
  S-----------S                                                  :
  |                                                              :
  Cys-Asp-Asp-Arg-Ile-Ser-Lys-Ile-Lys-Ala-Asn-Arg-Gln-Glu-Glu-Asn-Leu;
```

-continued (SEQ ID NO:35)
```
  Phe-Ser-Gln-Ala-Val-Ala
  |
  Asn-Met-Gln-Cys-Gln-Arg-Arg-Phe-Tyr-Glu-Ala-Leu-His-Asp-Pro-Asn
           |                                                    :
  S------------S                                                :
  |                                                             :
  Cys-Asp-Asp-Arg-Ile-Ser-Lys-Ile-Lys-Ala-Asn-Arg-Gln-Glu-Glu-Asn-Leu;
```
and (SEQ ID NO:36)
```
  Phe-Asn-Met-Gln-Cys-Gln-Arg-Arg-Phe-Tyr-Glu-Ala-Leu-His-Asp-Pro-Asn
               |                                                    :
  S------------S                                                    :
  |                                                                 :
  Cys-Asp-Asp-Arg-Ile-Ser-Lys-Ile-Lys-Ala-Asn-Arg-Gln-Glu-Glu-Asn-Leu.
```

In still another aspect, the invention provides a cyclized Z domain variant peptide selected from the group consisting of (SEQ ID NO:37)
```
  Phe-Lys-Asn-Asp-Val-Ala
  |
  Asn-Lys-Glu-Cys-Gln-Ala-Arg-Phe-Tyr-Glu-Ala-Leu-His-Asp-Pro-Asn
               |                                                :
  S------------S                                                :
  |                                                             :
  Cys-Asp-Asp-Lys-Ile-Ser-Gln-Ile-Lys-Ala-Asn-Arg-Gln-Glu-Glu-Asn-Leu;
```

(SEQ ID NO:38)
```
  Phe-Gly-Asn-Arg-Val-Ala
  |
  Asn-Lys-Glu-Cys-Gln-Ala-Arg-Phe-Tyr-Glu-Ala-Leu-His-Asp-Pro-Asn
               |                                                :
  S------------S                                                :
  |                                                             :
  Cys-Asp-Asp-Lys-Ile-Ser-Gln-Ile-Lys-Ala-Asn-Arg-Gln-Glu-Glu-Asn-Leu;
```

(SEQ ID NO:39)
```
  Phe-Ser-Gln-Ala-Val-Ala
  |
  Asn-Lys-Glu-Cys-Gln-Ala-Arg-Phe-Tyr-Glu-Ala-Leu-His-Asp-Pro-Asn
               |                                                :
  S------------S                                                :
  |                                                             :
  Cys-Asp-Asp-Lys-Ile-Ser-Gln-Ile-Lys-Ala-Asn-Arg-Gln-Glu-Glu-Asn-Leu;
```

(SEQ ID NO:40)
```
  Phe-Lys-Asn-Asp-Val-Ala
  |
  Asn-Met-Gln-Cys-Gln-Ala-Arg-Phe-Tyr-Glu-Ala-Leu-His-Asp-Pro-Asn
               |                                                :
  S------------S                                                :
  |                                                             :
  Cys-Asp-Asp-Lys-Ile-Ser-Gln-Ile-Lys-Ala-Asn-Arg-Gln-Glu-Glu-Asn-Leu;
```

(SEQ ID NO:41)
```
  Gly-Lys-Asn-Asp-Val-Ala
  |
  Trp-Met-Arg-Cys-Gln-Ala-Arg-Phe-Tyr-Glu-Ala-Leu-His-Asp-Pro-Asn
               |                                                :
  S------------S                                                :
  |                                                             :
  Cys-Asp-Asp-Lys-Ile-Ser-Gln-Ile-Lys-Ala-Asn-Arg-Gln-Glu-Glu-Asn-Leu;
```

(SEQ ID NO:42)
```
  Phe-Lys-Asn-Asp-Val-Ala
  |
  Asn-Lys-Glu-Cys-Gln-Ala-Ala-Phe-Tyr-Glu-Ala-Leu-His-Asp-Pro-Asn
               |                                                :
  S------------S                                                :
  |                                                             :
  Cys-Asp-Asp-Lys-Ile-Ser-Gln-Ile-Lys-Ala-Asn-Arg-Gln-Glu-Glu-Asn-Leu;
```

(SEQ ID NO:43)

```
      Phe-Lys-Asn-Asp-Val-Ala
             |
      Asn-Lys-Glu-Cys-Gln-Ala-Arg-Phe-Tyr-Glu-Ala-Leu-His-Asp-Pro-Asn
                     |                                              ⋮
      S------------ S                                               ⋮
      |                                                             ⋮
      Cys-Asp-Asp-Arg-Ile-Ser-Lys-Ile-Lys-Ala-Asn-Arg-Gln-Glu-Glu-Asn-Leu;
```

(SEQ ID NO:44)

```
      Phe-Gly-Asn-Arg-Val-Ala
             |
      Asn-Met-Gln-Cys-Gln-Ala-Arg-Phe-Tyr-Glu-Ala-Leu-His-Asp-Pro-Asn
                     |                                              ⋮
      S------------ S                                               ⋮
      |                                                             ⋮
      Cys-Asp-Asp-Arg-Ile-Ser-Lys-Ile-Lys-Ala-Asn-Arg-Gln-Glu-Glu-Asn-Leu;
```

(SEQ ID NO:45)

```
      Phe-Ser-Gln-Ala-Val-Ala
             |
      Asn-Met-Gln-Cys-Gln-Ala-Arg-Phe-Tyr-Glu-Ala-Leu-His-Asp-Pro-Asn
                     |                                              ⋮
      S------------ S                                               ⋮
      |                                                             ⋮
      Cys-Asp-Asp-Arg-Ile-Ser-Lys-Ile-Lys-Ala-Asn-Arg-Gln-Glu-Glu-Asn-Leu;
``` and (SEQ ID NO:46)

```
      Phe-Asn-Met-Gln-Cys-Gln-Ala-Arg-Phe-Tyr-Glu-Ala-Leu-His-Asp-Pro-Asn
                     |                                              ⋮
      S------------ S                                               ⋮
      |                                                             ⋮
      Cys-Asp-Asp-Arg-Ile-Ser-Lys-Ile-Lys-Ala-Asn-Arg-Gln-Glu-Glu-Asn-Leu.
```

In a preferred embodiment, the invention provides peptides of Formula (IIa) wherein $X_1$ is Ala-Val-$AA_3$-$AA_4$-$AA_5$ (SEQ ID NO:2), $AA_3$ is Ala, $AA_4$ is Gln, and $AA_5$ is Ser.

In another preferred embodiment, the invention provides peptides of Formula (IIa) wherein $X_1$ is Ala-Val-$AA_3$-$AA_4$-$AA_5$ (SEQ ID NO:2), $AA_3$ is Ala, $AA_4$ is Gln, $AA_5$ is Ser, $AA_6$ is Phe, $AA_7$ is Asn, $AA_8$ is Lys, $AA_9$ is Glu, $AA_{12}$ is Asn, $AA_{13}$ is Arg, $AA_{33}$ is Gln, and $AA_{36}$ is Lys.

In yet another aspect, the invention provides peptides of Formula (IIa) wherein $X_1$ is Ala-Val-$AA_3$-$AA_4$-$AA_5$ (SEQ ID NO:2), $AA_3$ is Ala, $AA_4$ is Gln, $AA_5$ is Ser, and $AA_{12}$ is Ala.

In still another aspect, the invention provides peptides of Formula (IIa) wherein $X_1$ is Ala-Val-$AA_3$-$AA_4$-$AA_5$ (SEQ ID NO:2), $AA_3$ is Ala, $AA_4$ is Gln, $AA_5$ is Ser, $AA_6$ is Phe, $AA_7$ is Asn, $AA_8$ is Lys, $AA_9$ is Glu, $AA_{12}$ is Ala, $AA_{13}$ is Arg, $AA_{33}$ is Gln, and $AA_{36}$ is Lys.

In yet another preferred embodiment, the invention provides peptides of Formula (IIa) wherein $AA_6$ is Gly, $AA_7$ is Trp, $AA_8$ is Met, and $AA_9$ is Arg.

In still another preferred embodiment, the invention provides peptides of Formula (IIa) wherein $X_1$ is Ala-Val-$AA_3$-$AA_4$-$AA_5$ (SEQ ID NO:2), $AA_6$ is Gly, $AA_7$ is Trp, $AA_8$ is Met, $AA_9$ is Arg, $AA_3$ is Asp, $AA_4$ is Asn, $AA_5$ is Lys, $AA_{12}$ is Asn, $AA_{13}$ is Arg, $AA_{33}$ is Gln; and $AA_{36}$ is Lys.

Also encompassed herein are peptides of Formula (IIa) wherein $AA_6$ is Gly, $AA_7$ is Trp, $AA_8$ is Met, $AA_9$ is Arg, and $AA_{12}$ is Ala.

Further encompassed herein are peptides of Formula (IIa) wherein $X_1$ is Ala-Val-$AA_3$-$AA_4$-$AA_5$ (SEQ ID NO:2), $AA_6$ is Gly, $AA_7$ is Trp, $AA_8$ is Met, $AA_9$ is Arg, $AA_3$ is Asp, $AA_4$ is Asn, $AA_5$ is Lys, $AA_{12}$ is Ala, $AA_{13}$ is Arg, $AA_{33}$ is Gln; and $AA_{36}$ is Lys.

In a further preferred embodiment, the invention provides peptides of Formula (IIa) wherein $AA_{12}$ is Arg.

Also preferred are peptides of Formula (IIa) wherein $X_1$ is Ala-Val-$AA_3$-$AA_4$-$AA_5$ (SEQ ID NO:2), $AA_{12}$ is Arg, $AA_3$ is Asp, $AA_4$ is Asn, $AA_5$ is Lys, $AA_6$ is Phe, $AA_7$ is Asn, $AA_8$ is Lys, $AA_9$ is Glu, $AA_{13}$ is Arg, $AA_{33}$ is Gln, and $AA_{36}$ is Lys.

Further encompassed within the scope of the invention are peptides of Formula (IIa) wherein $AA_{12}$ is Ala.

Additionally encompassed within the scope of the invention are peptides of Formula (IIa) wherein $X_1$ is Ala-Val-$AA_3$-$AA_4$-$AA_5$ (SEQ ID NO:2), $AA_{12}$ is Ala, $AA_3$ is Asp, $AA_4$ is Asn, $AA_5$ is Lys, $AA_6$ is Phe, $AA_7$ is Asn, $AA_8$ is Lys, $AA_9$ is Glu, $AA_{13}$ is Arg, $AA_{33}$ is Gln, and $AA_{36}$ is Lys.

In an additional preferred embodiment, the invention provides peptides of Formula (IIa) wherein $AA_{33}$ is Lys and $AA_{36}$ is Arg.

In still another preferred embodiment, the invention provides peptides of Formula (IIa) wherein $X_1$ is Ala-Val-$AA_3$-$AA_4$-$AA_5$ (SEQ ID NO:2), $AA_{33}$ is Lys, $AA_{36}$ is Arg, $AA_3$ is Asp, $AA_4$ is Asn, $AA_5$ is Lys, $AA_6$ is Phe, $AA_7$ is Asn, $AA_8$ is Lys, $AA_9$ is Glu, $AA_{12}$ is Asn, and $AA_{13}$ is Arg.

Further encompassed herein are peptides of Formula (IIa) wherein $AA_{33}$ is Lys, $AA_{36}$ is Arg, and $AA_{12}$ is Ala.

Additionally encompassed herein are peptides of Formula (IIa) wherein $X_1$ is Ala-Val-$AA_3$-$AA_4$-$AA_5$ (SEQ ID NO:2), $AA_{33}$ is Lys, $AA_{36}$ is Arg, $AA_3$ is Asp, $AA_4$ is Asn, $AA_5$ is Lys, $AA_6$ is Phe, $AA_7$ is Asn, $AA_8$ is Lys, $AA_9$ is Glu, $AA_{12}$ is Ala, and $AA_{13}$ is Arg.

In yet another preferred embodiment, the invention provides peptides of Formula (IIa) wherein $X_1$ is Ala-Val-$AA_3$-$AA_4$-$AA_5$ (SEQ ID NO:2), $AA_3$ is Arg, $AA_5$ is Gly, $AA_8$ is Met, $AA_9$ is Gln, $AA_{12}$ is Arg, $AA_{33}$ is Lys, and $AA_{36}$ is Arg.

In a more preferred embodiment, the invention provides peptides of Formula (IIa) wherein $X_1$ is Ala-Val-$AA_3$-$AA_4$-$AA_5$ (SEQ ID NO:2), $AA_3$ is Arg, $AA_5$ is Gly, $AA_8$ is Met, $AA_9$ is Gln, $AA_{12}$ is Arg, $AA_{33}$ is Lys, $AA_{36}$ is Arg, $AA_4$ is Asn, $AA_6$ is Phe, $AA_7$ is Asn, and $AA_{13}$ is Arg.

Also provided herein are peptides of Formula (IIa) wherein $X_1$ is Ala-Val-$AA_3$-$AA_4$-$AA_5$ (SEQ ID NO:2), $AA_3$ is Arg, $AA_5$ is Gly, $AA_8$ is Met, $AA_9$ is Gln, $AA_{12}$ is Ala, $AA_{33}$ is Lys, and $AA_{36}$ is Arg.

Further provided herein are peptides of Formula (IIa) wherein $X_1$ is Ala-Val-$AA_3$-$AA_4$-$AA_5$ (SEQ ID NO:2), $AA_3$ is Arg, $AA_5$ is Gly, $AA_8$ is Met, $AA_9$ is Gln, $AA_{12}$ is Ala, $AA_{33}$ is Lys, $AA_{36}$ is Arg, $AA_4$ is Asn, $AA_6$ is Phe, $AA_7$ is Asn, and $AA_3$ is Arg.

In an additional preferred embodiment, the invention provides peptides of Formula (IIa) wherein $X_1$ is Ala-Val-$AA_3$-$AA_4$-$AA_5$ (SEQ ID NO:2), $AA_3$ is Ala, $AA_4$ is Gln, $AA_5$ is Ser, $AA_8$ is Met, $AA_9$ is Gln, $AA_{12}$ is Arg, $AA_{33}$ is Lys, and $AA_{36}$ is Arg.

In a more preferred embodiment, the invention provides peptides of Formula (IIa) wherein $X_1$ is Ala-Val-$AA_3$-$AA_4$-$AA_5$ (SEQ ID NO:2), $AA_3$ is Ala, $AA_4$ is Gln, $AA_5$ is Ser, $AA_8$ is Met, $AA_9$ is Gln, $AA_{12}$ is Arg, $AA_{33}$ is Lys, $AA_{36}$ is Arg, $AA_6$ is Phe, $AA_7$ is Asn, and $AA_{13}$ is Arg.

Additionally provided herein are peptides of Formula (IIa) wherein $X_1$ is Ala-Val-$AA_3$-$AA_4$-$AA_5$ (SEQ ID NO:2), $AA_3$ is Ala, $AA_4$ is Gln, $AA_5$ is Ser, $AA_8$ is Met, $AA_9$ is Gln, $AA_{12}$ is Ala, $AA_{33}$ is Lys, and $AA_{36}$ is Arg.

In another embodiment, the invention provides peptides of Formula (IIa) wherein $X_1$ is Ala-Val-$AA_3$-$AA_4$-$AA_5$ (SEQ ID NO:2), $AA_3$ is Ala, $AA_4$ is Gln, $AA_5$ is Ser, $AA_8$ is Met, $AA_9$ is Gln, $AA_{12}$ is Ala, $AA_{33}$ is Lys, $AA_{36}$ is Arg, $AA_6$ is Phe, $AA_7$ is Asn, and $AA_{13}$ is Arg.

In a particularly preferred embodiment, the invention provides peptides of Formula (IIa) wherein $X_1$ is absent, $AA_8$ is Met, $AA_9$ is Gln, $AA_{12}$ is Arg, $AA_{33}$ is Lys, and $AA_{36}$ is Arg.

In an even more preferred embodiment, the invention provides peptides of Formula (IIa) wherein $X_1$ is absent, $AA_8$ is Met, $AA_9$ is Gln, $AA_{12}$ is Arg, $AA_{33}$ is Lys, $AA_{36}$ is Arg, $AA_6$ is Phe, $AA_7$ is Asn, and $AA_{13}$ is Arg.

In yet another embodiment, the invention provides peptides of Formula (IIa) wherein $X_1$ is absent, $AA_8$ is Met, $AA_9$ is Gln, $AA_{12}$ is Ala, $AA_{33}$ is Lys, and $AA_{36}$ is Arg.

In still another embodiment, the invention provides peptides of Formula (IIa) wherein $X_1$ is absent, $AA_8$ is Met, $AA_9$ is Gln, $AA_{12}$ is Ala, $AA_{33}$ is Lys, $AA_{36}$ is Arg, $AA_6$ is Phe, $AA_7$ is Asn, and $AA_{13}$ is Arg.

In a preferred embodiment, the Z domain variant peptides of the invention are non-covalently adsorbed or covalently bound to a macromolecule, such as a solid support. It will be appreciated that the invention encompasses both macromolecules complexed with the cyclized Z domain variant peptides provided herein and macromolecules complexed with the linear Z domain variant peptides provided herein. In general, the solid support is an inert matrix, such as a polymeric gel, comprising a three dimensional structure, lattice or network of a material. Almost any macromolecule, synthetic or natural, can form a gel in a suitable liquid when suitably cross-linked with a bifunctional reagent. Preferably, the macromolecule selected is convenient for use in affinity chromatography. Most chromatographic matrices used for affinity chromatography are xerogels. Such gels shrink on drying to a compact solid comprising only the gel matrix. When the dried xerogel is resuspended in the liquid, the gel matrix imbibes liquid, swells and returns to the gel state. Xerogels suitable for use herein include polymeric gels, such as cellulose, cross-linked dextrans (e.g. Sepharose), agarose, cross-linked agarose, polyacrylamide gels, and polyacrylamide-agarose gels.

Alternatively, aerogels can be used for affinity chromatography. These gels do not shrink on drying but merely allow penetration of the surrounding air. When the dry gel is exposed to liquid, the latter displaces the air in the gel. Aerogels suitable for use herein include porous glass and ceramic gels.

Also encompassed herein are the Z domain variant peptides of the invention coupled to derivatized gels wherein the derivative moieties facilitate the coupling of the peptide ligands to the gel matrix and avoid steric hindrance of the peptide ligand-IgG interaction in affinity chromatography. Alternatively, spacer arms can be interposed between the gel matrix and the peptide ligand for similar benefits.

In another embodiment, the invention provides fusion proteins in which a selected or desired polypeptide is fused at its N-terminus or its C-terminus, or at both terminii, to one or more of the present Z domain variant peptides. The invention contemplates the use of both cyclized Z domain variant peptides and linear Z domain variant peptides in fusion proteins. In a preferred embodiment, the fusion protein is specifically cleavable such that at least a substantial portion of the Z domain variant peptide sequence can be proteolytically cleaved away from the fusion protein to yield the desired polypeptide. The fusion proteins of the invention can be designed with cleavage sites recognized by chemical or enzymatic proteases. In one embodiment, the fusion protein is designed with a unique cleavage site (or sites) for removal of the Z domain variant peptide sequence, i.e. the fusion protein is designed such that a given protease (or proteases) cleaves away the Z domain variant peptide sequence but does not cleave at any site within the sequence of the desired protein, avoiding fragmentation of the desired protein. In another embodiment, the cleavage site (or sites) at the fusion joint (or joints) is designed such that cleavage of the fusion protein with a given enzyme liberates the authentic, intact sequence of the desired protein from the remainder of the fusion protein sequence.

II. Synthesis of Z Domain Variant Peptides

1. Chemical Synthesis a. General Procedures

One method of producing the Z domain variants of the invention involves chemical synthesis of the peptides. This can be accomplished by using methodologies well known in the art (see Kelley, R. F. & Winkler, M. E. in *Genetic Engineering Principles and Methods*, Setlow, J. K, ed., Plenum Press, N.Y., vol. 12, pp 1–19 (1990), Stewart, J. M. Young, J. D., *Solid Phase Peptide Synthesis*, Pierce Chemical Co., Rockford, Ill. (1984); see also U.S. Pat. Nos. 4,105,603; 3,972,859; 3,842,067; and 3,862,925).

Peptides of the invention can be conveniently prepared using solid phase peptide synthesis (Merrifield, *J. Am. Chem. Soc.*, 85: 2149 (1964); Houghten, *Proc. Natl. Acad. Sci. USA*, 82: 5132 (1985). Solid phase synthesis begins at the carboxy terminus of the putative peptide by coupling a protected amino acid to an inert solid support. The inert solid support can be any macromolecule capable of serving as an anchor for the C-terminus of the initial amino acid. Typically, the macromolecular support is a cross-linked polymeric resin (e.g. a polyamide or polystyrene resin) as shown in FIGS. 1–1 and 1–2, on pages 2 and 4 of Stewart and Young, supra. In one embodiment, the C-terminal amino acid is coupled to a polystyrene resin to form a benzyl ester. A macromolecular support is selected such that the peptide anchor link is stable under the conditions used to deprotect the α-amino group of the blocked amino acids in peptide synthesis. If an base-labile α-protecting group is used, then it is desirable to use an acid-labile link between the peptide and the solid support. For example, an acid-labile ether resin is effective for base-labile Fmoc-amino acid peptide synthesis as described on page 16 of Stewart and Young, supra.

Alternatively, a peptide anchor link and α-protecting group that are differentially labile to acidolysis can be used. For example, an aminomethyl resin such as the phenylacetamidomethyl (Pam) resin works well in conjunction with Boc-amino acid peptide synthesis as described on pages 11–12 of Stewart and Young, supra.

After the initial amino acid is coupled to an inert solid support, the α-amino protecting group of the initial amino acid is removed with, for example, trifluoroacetic acid (TFA) in methylene chloride and neutralizing in, for example, triethylamine (TEA). Following deprotection of the initial amino acid's α-amino group, the next α-amino and sidechain protected amino acid in the synthesis is added. The remaining α-amino and, if necessary, side chain protected amino acids are then coupled sequentially in the desired order by condensation to obtain an intermediate compound connected to the solid support. Alternatively, some amino acids may be coupled to one another to form a fragment of the desired peptide followed by addition of the peptide fragment to the growing solid phase peptide chain.

The condensation reaction between two amino acids, or an amino acid and a peptide, or a peptide and a peptide can be carried out according to the usual condensation methods such as the axide method, mixed acid anhydride method, DCC (N,N'-dicyclohexylcarbodiimide) or DIC (N,N'-diisopropylcarbodiimide) methods, active ester method, p-nitrophenyl ester method, BOP (benzotriazole-1-yl-oxy-tris [dimethylamino] phosphonium hexafluorophosphate) method, N-hydroxysuccinic acid imido ester method, etc, and Woodward reagent K method.

It is common in the chemical syntheses of peptides to protect any reactive side-chain groups of the amino acids with suitable protecting groups. Ultimately, these protecting groups are removed after the desired polypeptide chain has been sequentially assembled. Also common is the protection of the α-amino group on an amino acid or peptide fragment while the C-terminal carboxy group of the amino acid or peptide fragment reacts with the free N-terminal amino group of the growing solid phase polypeptide chain, followed by the selective removal of the α-amino group to permit the addition of the next amino acid or peptide fragment to the solid phase polypeptide chain. Accordingly, it is common in polypeptide synthesis that an intermediate compound is produced which contains each of the amino acid residues located in the desired sequence in the peptide chain wherein individual residues still carry side-chain protecting groups. These protecting groups can be removed substantially at the same time to produce the desired polypeptide product following removal from the solid phase.

α- and ε-amino side chains can be protected with benzyloxycarbonyl (abbreviated Z), isonicotinyloxycarbonyl (iNOC), o-chlorobenzyloxycarbonyl [Z(2Cl)], p-nitrobenzyloxycarbonyl [Z(NO$_2$)], p-methoxybenzyloxycarbonyl [Z(OMe)], t-butoxycarbonyl (Boc), t-amyloxycarbonyl (Aoc), isobornyloxycarbonyl, adamantyloxycarbonyl, 2-(4-biphenyl)-2-propyloxycarbonyl (Bpoc), 9-fluorenylmethoxycarbonyl (Fmoc), methylsulfonyethoxycarbonyl (Msc), trifluoroacetyl, phthalyl, formyl, 2-nitrophenylsulphenyl (NPS), diphenylphosphinothioyl (Ppt), and dimethylphosphinothioyl (Mpt) groups, and the like.

Protective groups for the carboxy functional group are exemplified by benzyl ester (OBzl), cyclohexyl ester (Chx), 4-nitrobenzyl ester (ONb), t-butyl ester (Obut), 4-pyridylmethyl ester (OPic), and the like. It is often desirable that specific amino acids such as arginine, cysteine, and serine possessing a functional group other than amino and carboxyl groups are protected by a suitable protective group. For example, the guanidino group of arginine may be protected with nitro, p-toluenesulfonyl, benzyloxycarbonyl, adamantyloxycarbonyl, p-methoxybenzesulfonyl, 4-methoxy-2,6-dimethylbenzenesulfonyl (Nds), 1,3,5-trimethylphenysulfonyl (Mts), and the like. The thiol group of cysteine can be protected with p-methoxybenzyl, trityl, and the like.

Many of the blocked amino acids described above can be obtained from commercial sources such as Novabiochem (San Diego, Calif.), Bachem, CA (Torrence, Calif.) or Peninsula Labs (Belmont, Calif.).

Stewart and Young, supra, provides detailed information regarding procedures for preparing peptides. Protection of α-amino groups is described on pages 14–18, and side chain blockage is described on pages 18–28. A table of protecting groups for amine, hydroxyl and sulfhydryl functions is provided on pages 149–151.

After the desired amino acid sequence has been completed, the peptide can be cleaved away from the solid support, recovered and purified. The peptide is removed from the solid support by a reagent capable of disrupting the peptide-solid phase link, and optionally deprotects blocked side chain functional groups on the peptide. In one embodiment, the peptide is cleaved away from the solid phase by acidolysis with liquid hydrofluoric acid (HF), which also removes any remaining side chain protective groups. Preferably, in order to avoid alkylation of residues in the peptide (for example, alkylation of methionine, cysteine, and tyrosine residues), the acidolysis reaction mixture contains thio-cresol and cresol scavengers. Following HF cleavage, the resin is washed with ether, and the free peptide is extracted from the solid phase with sequential washes of acetic acid solutions. The combined washes are lyophilized, and the peptide is purified.

In one embodiment, the peptides of the invention are synthesized according to the method of Fields et al., *Int. J. Peptide Protein Res.*, 35: 161–214 (1990), as described in Example 2 below.

b. Disulfide Linked Z Domain Variant Peptides

As described in Section B(I) above, some embodiments of the invention provide Z domain variant peptides that are cyclized by formation of a disulfide bond between cysteine residues substituted at amino acid positions 10 and 39 of the Z domain template amino acid sequence. Such peptides can be made by chemical synthesis as described above and then cyclized by any convenient method used in the formation of disulfide linkages. For example, peptides can be recovered from solid phase synthesis with sulfhydryls in reduced form, dissolved in a dilute solution wherein the intramolecular cysteine concentration exceeds the intermolecular cysteine concentration in order to optimize intramolecular disulfide bond formation, such as a peptide concentration of 25 mM to 1 μM, and preferably 500 μM to 1 μM, and more preferably 25 μM to 1 μM, and then oxidized by exposing the free sulfhydryl groups to a mild oxidizing agent that is sufficient to generate intramolecular disulfide bonds, e.g. molecular oxygen with or without catalysts such as metal cations, potassium ferricyanide, sodium tetrathionate, etc. In one embodiment, the peptides are cyclized as described in Example 2 below. Alternatively, the peptides can be cyclized as described in Pelton et al., *J. Med Chem.*, 29: 2370–2375 (1986).

2. Recombinant Synthesis

In a further embodiment, the present invention encompasses a composition of matter comprising isolated nucleic acid, preferably DNA, encoding a polypeptide selected from the group consisting of the Z domain variant peptides described in Table 2 below. DNAs encoding the Z domain variant peptides of the invention can be prepared by a variety of methods known in the art. These methods include, but are not limited to, chemical synthesis by any of the methods described in Engels et al., *Agnew. Chem. Int. Ed. Engl.,* 28: 716–734 (1989), the entire disclosure of which is incorporated herein by reference, such as the triester, phosphite, phosphoramidite and H-phosphonate methods. In one embodiment, codons preferred by the expression host cell are used in the design of the Z domain variant-encoding DNA. Alternatively, DNA encoding the wild type Z domain can be isolated from a genomic or cDNA library, and the wild type DNA sequence can be altered to encode one of the Z domain variants by using recombinant DNA techniques, such as site specific mutagenesis (Kunkel et al., *Methods Enzymol.* 204:125–139 (1991); Carter, P., et al., *Nucl. Acids. Res.* 13:4331 (1986); Zoller, M. J. et al., *Nucl. Acids Res.* 10:6487 (1982)), cassette mutagenesis (Wells, J. A., et al., *Gene* 34:315 (1985)), restriction selection mutagenesis (Wells, J. A., et al., *Philos. Trans, R. Soc. London SerA* 317, 415 (1986)), and the like.

The invention further comprises an expression control sequence operably linked to the DNA molecule encoding a Z domain variant peptide of Table 2, and an expression vector, such as a plasmid, comprising the DNA molecule, wherein the control sequence is recognized by a host cell transformed with the vector. In general, plasmid vectors contain replication and control sequences which are derived from species compatible with the host cell. The vector ordinarily carries a replication site, as well as sequences which encode proteins that are capable of providing phenotypic selection in transformed cells.

For expression in prokaryotic hosts, suitable vectors include pBR322 (ATCC No. 37,017), phGH107 (ATCC No. 40,011), pBO475, pS0132, pRIT5, any vector in the pRIT20 or pRIT30 series (Nilsson and Abrahmsen, *Meth. Enzymol.,* 185: 144–161 (1990)), pRIT2T, pKK233-2, pDR540 and pPL-lambda. Prokaryotic host cells containing the expression vectors of the present invention include *E. coli* K12 strain 294 (ATCC NO. 31446), *E. coli* strain JM101 (Messing et al., *Nucl. Acid. Res.,* 9: 309 (1981)), *E. coli* strain B, *E. coli* strain$_{102}$ 1776 (ATCC No. 31537), *E. coli* c600 (Appleyard, *Genetics,* 39: 440 (1954)), *E. coli* W3110 (F-, gamma-, prototrophic, ATCC No. 27325), *E. coli* strain 27C7 (W3110, tonA, phoA E15, (argF-lac)169, ptr3, degP41, ompT, kan') (U.S. Pat. No. 5,288,931, ATCC No. 55,244), *Bacillus subtilis, Salmonella typhimurium, Serratia marcesans,* and Pseudomonas species.

In addition to prokaryotes, eukaryotic organisms, such as yeasts, or cells derived from multicellular organisms can be used as host cells. For expression in yeast host cells, such as common baker's yeast or *Saccharomyces cerevisiae,* suitable vectors include episomally replicating vectors based on the 2-micron plasmid, integration vectors, and yeast artificial chromosome (YAC) vectors. For expression in insect host cells, such as Sf9 cells, suitable vectors include baculoviral vectors. For expression in plant host cells, particularly dicotyledonous plant hosts, such as tobacco, suitable expression vectors include vectors derived from the Ti plasmid of *Agrobacterium tumefaciens.*

However, interest has been greatest in vertebrate host cells. Examples of useful mammalian host cells include monkey kidney CV1 line transformed by SV40 (COS-7, ATCC CRL 1651); human embryonic kidney line (293 or 293 cells subcloned for growth in suspension culture, Graham et al., *J. Gen Virol.,* 36: 59 (1977)); baby hamster kidney cells (BHK, ATCC CCL 10); Chinese hamster ovary cells/-DHFR (CHO, Urlaub and Chasin, *Proc. Natl. Acad. Sci. USA,* 77: 4216 (1980)); mouse sertoli cells (TM4, Mather, *Biol. Reprod.,* 23: 243–251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.,* 383: 44–68 (1982)); MRC 5 cells; FS4 cells; and a human hepatoma cell line (Hep G2). For expression in mammalian host cells, useful vectors include vectors derived from SV40, vectors derived from cytomegalovirus such as the pRK vectors, including pRK5 and pRK7 (Suva et al., *Science,* 237: 893–896 (1987), EP 307,247 (Aug. 15, 1989), EP 278,776 (Aug. 17, 1988)) vectors derived from vaccinia viruses or other pox viruses, and retroviral vectors such as vectors derived from Moloney's murine leukemia virus (MoMLV).

Optionally, the DNA encoding the Z domain variant of interest is operably linked to a secretory leader sequence resulting in secretion of the expression product by the host cell into the culture medium. Examples of secretory leader sequences include stII, ecotin, lamB, herpes GD, 1pp, alkaline phsophatase, invertase, and alpha factor. Also suitable for use herein is the 36 amino acid leader sequence of protein A (Abrahmsen et al., *EMBO J.,* 4: 3901 (1985)).

Host cells are transfected and preferably transformed with the above-described expression or cloning vectors of this invention and cultured in conventional nutrient media modified as appropriate for inducing promoters, selecting transformants, or amplifying the genes encoding the desired sequences.

Transfection refers to the taking up of an expression vector by a host cell whether or not any coding sequences are in fact expressed. Numerous methods of transfection are known to the ordinarily skilled artisan, for example, CaPO$_4$ precipitation and electroporation. Successful transfection is generally recognized when any indication of the operation of this vector occurs within the host cell.

Transformation means introducing DNA into an organism so that the DNA is replicable, either as an extrachromosomal element or by chromosomal integrant. Depending on the host cell used, transformation is done using standard techniques appropriate to such cells. The calcium treatment employing calcium chloride, as described in section 1.82 of Sambrook et al., *Molecular Cloning* (2nd ed.), Cold Spring Harbor Laboratory, NY (1989), is generally used for prokaryotes or other cells that contain substantial cell-wall barriers. Infection with *Agrobacterium tumefaciens* is used for transformation of certain plant cells, as described by Shaw et al., *Gene,* 23: 315 (1983) and WO 89/05859 published Jun. 29, 1989. For mammalian cells without such cell walls, the calcium phosphate precipitation method described in sections 16.30–16.37 of Sambrook et al., supra, is preferred. General aspects of mammalian cell host system transformations have been described by Axel in U.S. Pat. No. 4,399,216 issued Aug. 16, 1983. Transformations into yeast are typically carried out according to the method of Van Solingen et al., *J. Bact.,* 130: 946 (1977) and Hsiao et al., *Proc. Natl. Acad. Sci. (USA),* 76: 3829 (1979). However, other methods for introducing DNA into cells such as by nuclear injection, electroporation, or by protoplast fusion may also be used.

Prokaryotic host cells used to produce the present Z domain variant peptides can be cultured as described generally in Sambrook et al., supra.

The mammalian host cells used to produce the Z domain variant peptides of the invention can be cultured in a variety of media. Commercially available media such as Ham's F10 (Sigma), Minimal Essential Medium ((MEM), Sigma), RPMI-1640 (Sigma), and Dulbecco's Modified Eagle's Medium ((DMEM), Sigma) are suitable for culturing the host cells. In addition, any of the media described in Ham and Wallace, *Meth. Enz.*, 58: 44 (1979), Barnes and Sato, *Anal. Biochem.*, 102: 255 (1980), U.S. Pat. Nos. 4,767,704; 4,657,866; 4,927,762; or 4,560,655; WO 90/03430; WO 87/00195; U.S. Pat. Re. 30,985; or U.S. Pat. No. 5,122,469, the disclosures of all of which are incorporated herein by reference, may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics (such as Gentamycin™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

The host cells referred to in this disclosure encompass cells in in vitro culture as well as cells that are within a host animal.

In an intracellular expression system or periplasmic space secretion system, the recombinantly expressed Z domain variant peptide can be recovered from the culture cells by disprupting the host cell membrane/cell wall (e.g. by osmotic shock or solubilizing the host cell membrane in detergent). Alternatively, in an extracellular secretion system, the recombinant peptide can be recovered from the culture medium. As a first step, the culture medium or lysate is centrifuged to remove any particulate cell debris. The membrane and soluble protein fractions are then separated. The Z domain variant peptide can then be purified from the soluble protein fraction. If the peptide is expressed as a membrane bound species, the membrane bound peptide can be recovered from the membrane fraction by solubilization with detergents. The crude peptide extract can then be further purified by suitable procedures such as fractionation on immunoaffinity or ion-exchange columns; ethanol precipitation; reverse phase HPLC; chromatography on silica or on a cation exchange resin such as DEAE; chromatofocusing; SDS-PAGE; ammonium sulfate precipitation; gel filtration using, for example, Sephadex G-75; hydrophobic affinity resins and ligand affinity using IgG ligand immobilized on a matrix.

In cyclized embodiments of the invention, the recombinantly produced Z domain variant peptide can be cyclized by formation of an intramolecular disulfide bond as described in Section B(II)(1)(b) above.

III. Z Domain Variant Peptide Ligands for Affinity Chromatography of IgG

In one embodiment, the Z domain variant peptides are used as ligands in the affinity chromatography of IgG, IgG fusion proteins (immunoadhesins), and IgG-bearing cells. The Z domain variant peptides can be made as described in Section B(II) above. Next, the selected peptide can be coupled to a suitable macromolecular solid phase matrix, such as cellulose, cross-linked dextran derivatives (e.g. Sepharose), polyacrylamides, porous glass and ceramics, by any convenient method.

A commonly employed technique for attaching peptide ligands to polysaccharide matrices, e.g. agarose, dextran or cellulose, involves activation of the carrier with cyanogen halides and subsequent coupling of the peptide ligand's primary alphatic or aromatic amines to the activated matrix. The activation of polysaccharides with cyanogen bromide (CNBr) at alkaline pH was introduced to affinity chromatography by Axen et al., *Nature*, 214: 1302 (1967). In one aspect of the invention, the activation of polysaccharide matrices, particularly agarose matrices, is performed according to the titration-activation method. In this procedure, for example, 20 g of exhaustively washed moist agarose cake is added to 20 ml of water in a 100 ml beaker equipped with a 0–100° C. thermometer, a pH meter and a 25 mm magnetic stirring bar. The suspension is stirred slowly, the temperature lowered to about 10–15° C. by the addition of crushed ice and the pH adjusted to 10.8±0.1 by the addition of 1–2 drops of 4 N NaOH. The activation procedure is initiated by the addition of the CNBr and the pH of the reaction maintained at 10.8±0.1 by manual titration with the 4 N NaOH. The CNBr (100 g/mg moist weight gel) can be added as a crystalline solid, a crushed solid, an aqueous solution or by adding an aliquot of a stock solution. The latter can be prepared by dissolving CNBr in acetonitrile (1 g/ml) and storing in a tightly stoppered vial at −20° C. The temperature is subsequently allowed to rise to 18–20° C.

Despite the relative simplicity of the titration method, it may be preferable to use the faster and technically simplified method of March et al., *Anal. Biochem.*, 60: 149 (1974). The activation procedure is performed in concentrated carbonate buffer. The required amount of washed gel is suspended in an equal volume of 2 M $NaHCO_3$-$NaCO_3$ buffer (pH 10.9) in a beaker equipped with a thermometer and magnetic stirring bar. The slurry is cooled to approximately 4–5° C., the activated gel is transferred to a sintered funnel and washed.

The concentration of CNBr recommended in the procedures described above is satisfactory for moderate levels of ligand substitution. When lower or higher levels of activation are required, 50 mg and 200–300 mg CNBr/g moist weight gel respectively can be employed together with 2 M and 8 M NaOH for the titration.

It is generally recognized that the CNBr-activated intermediate functional groups of polysaccharide gels display limited stability and therefore it is preferable that the gel be washed as rapidly as possible prior to transferring the gel to the coupling-reaction medium. At the end of the activation step, the gel is rapidly cooled by the addition of crushed ice and poured into a large sintered glass funnel which has been pre-cooled with crushed ice. The suspension is rapidly filtered into a Buchner flask (2 liter) containing solid ferrous sulfate to remove unreacted CNBr and cyanides as harmless ferrocyanide. The gel is subsequently washed under suction with 1 liter ice-cold distilled water and 1 liter of the buffer to be used in the coupling stage, typically ice-cold 0.1 M $NaHCO_3$-$NaCO_3$ buffer (pH 8.5–9.5).

CNBr-activated Sepharose 4B is available commercially from Pharmacia and obviates the hazardous manipulation of CNBr. The activated gel is freeze dried in the presence of dextran and lactose to preserve the beaded form and supplied in 15 g air-tight packs. The required amount of freeze-dried powder is swollen in 1 mM HCl on a glass filter and washed with at least 200 ml of the same solution per gram of powder. 1 g of freeze-dried material is roughly equivalent to 3.5 ml final gel volume. The ligand-binding capacity of the gel is conserved more effectively by washing with solutions of low pH than with solutions of pH>7. The gel is then ready to couple ligand as soon as the washing is completed.

Pharmacia also markets CNBr-activated Sepharose 6 MB for use in cell biology and immunology for the separation of "functionally homogeneous cell populations". It is produced by activation of Sepharose 6MB macrobeads (diameter 200–300 µm) with cyanogen bromide and is handled in a manner analogous to CNBr-activated Sepharose 4B.

The peptide to be coupled is suspended in a volume of the cold buffer equal to the volume of the packed gel, added to the moist, washed gel, and then the suspension is immediately mixed (in a Buchner funnel) with a glass stirring rod. The entire procedure of washing, adding the peptide solution, and mixing preferably consumes less than 90 seconds. The suspension is transferred from the Buchner funnel to a beaker containing a magnetic mixing bar and is gently stirred at 4° C. Although the reaction is essentially complete in 2 to 3 hours, the mixture is allowed to stand at 4° C. for 16 to 20 hours to insure complete loss of reactive polysaccharide groups. The peptide-linked gel is then washed with large volumes of water until it is established that peptide is no longer being removed.

The quantity of peptide ligand coupled to the polysaccharide gel can in part be controlled by the amount of peptide added to the activated matrix. When highly substituted polysaccharide gel derivatives are desired, the amount of peptide added should be 20 to 30 times greater than that which is desired in the final product. For ordinary procedures, 100 to 150 mg of cyanogen bromide are used per ml of packed polysaccharide gel, but much higher coupling yields can be obtained if this amount is increased to 250 to 300 mg. The pH at which the coupling reaction is performed also affects the degree of coupling, since it is only the unprotonated form of a peptide's amino groups that reacts with CNBr-activated polysaccharides. Preferably, the N-terminal α-amino group of the peptide ligand is used for coupling with the activated polysaccharide matrix. α-amino groups will couple optimally at a pH of about 9.5 to 10.0. If coupling at the ε-amino group(s) of the selected peptide ligand (such as the ε-amino groups of the lysinyl residues) is desired, the coupling reaction should be conducted at a pH value of about 10.0, and a large excess of peptide should be added. If coupling at the aromatic amino groups in the histidyl or tryptophanyl residues of the selected peptide is desired, very high coupling efficiency can be obtained at pH values between 8 and 9.

In another embodiment, a spacer molecule is interposed between the peptide ligand and the matrix backbone. For example, it is possible to use the bromoacetyl, diazonium, or sulfhydryl polysaccharide matrix derivatives described in Cuatrecasas, *J. Biol. Chem.*, 245: 3059–3065 (1970) to couple the selected peptide to a solid support by means of an arm extending some distance from the matrix backbone. Alternatively, the spacer arms described in Lowe, "An Introduction to Affinity Chromatography", in *Laboratory Techniques in Biochemistry and Molecular Biology*, Work and Work, eds, North-Holland Publishing Co. (New York: 1979), pp.344–400 can be used to link the peptides of the invention to polysaccharide matrices.

The matrix coupled to the Z domain variant peptides of the invention can be used for affinity chromatographic purification of IgG, IgG fusion proteins or IgG-bearing cells by any of the techniques well known and widely used for protein A affinity chromatography. Since the peptides of the invention possess IgG-binding activities similar to that of wild type protein A, affinity chromatography with the insolubilized peptide ligand can be performed under the same or similar conditions as affinity chromatography with insolubilized protein A.

In one embodiment for affinity purification of IgG or IgG fusion proteins, a gravity-feed operated column of the desired size is packed with the affinity gel and washed with at least 5 bed volumes of Tris-saline Tween 20 (50 mM Tris buffer, pH 7.6, 150 mM NaCl and 0.05% Tween 20) (TST) prior to use. The column can then be equilibrated in 2–3 bed volumes each of 1) 0.5 M $CH_3OOH$ (HAc) adjusted to pH 3.4 with $NH_4CH_3COOH$ ($NH_4Ac$); 2) TST; 3)0.5 M HAc, pH 3.4; and 4) TST. The pH of the column eluate is determined, and the pH of the sample, cell supernatant or clarified growth medium is adjusted to match, if necessary. A suitable aliquot of the sample is applied to the top of a moist bed of the affinity adsorbent, allowed to run in, and the column is washed with 1) 10 bed volumes of TST and 2) 2 bed volumes of 5 mM $NH_4Ac$, pH 5.0. Next, the sample can be eluted from the column with 0.5 M HAc, pH 3.4 and aliquots of eluate collected and peak fractions identified by spectrophotometry at 280 nm. Alternatively, samples can be eluted from the column with concentrated solutions of the same peptide used as the column adsorbent.

It will be appreciated that affinity purification techniques using the Z domain variant peptides of the invention are not limited to column chromatographic procedures. In many cases, it may be preferable to use a batchwise technique. When relatively small amounts of IgG or IgG fusion protein are to be extracted from a mixture containing a significant proportion of inert protein, the purification may be achieved more readily by adding a slurry of the adsorbent. The non-adsorbed proteins can be washed off either under batchwise conditions or by placing the adsorbent in a chromatographic column and proceeding as described above.

IV. Z Domain Variant Peptide Affinity Handles for IRG Ligand Affinity Chromatograph of Fusion Proteins The ability of the Z domain variant peptides of the invention to bind to the Fc portion of most mammlian class G immunoglobulins makes them useful as "affinity handles" in gene fusion expression systems. This strong and specific affinity permits the purification of the fusion proteins in a single step by IgG affinity chromatography. The Z domain variant peptide "handle" can later be removed to release the desired, native sequence protein product. It has also been shown that many heterologous proteins are degraded when expressed directly in *E. coli*, but are stable when expressed as fusion proteins (Marston, *Biochem. J.*, 240: 1 (1986)).

The question of whether to remove the peptide purification handle (tail) is essentially dependent on the end-use of the selected or desired protein. Accordingly, the invention encompasses fusion proteins that either are or are not designed to facilitate the removal of the Z domain variant peptide to which the desired protein is fused. For lab-scale characterization of a protein that has previously been difficult to obtain in sufficient quantities, it can be convenient to leave the peptide "tail" on, after initial demonstration that the tail does not interfere with the biological function of the desired protein. If interference is encountered, removal of the tail may be necessary in order to obtain reliable results. In some applications, a slight or even considerable loss of activity can be justified by the ease of purification and assayability provided by the fusion moiety. Selected proteins in this category may include industrial enzymes, diagnostic proteins, and enzymes that are to be immobilized. In the latter case the tail could be designed to promote simultaneous purification and immobilization by binding to a solid support. For pharmaceutical applications, precise removal of the fusion tail is usually desired in order to achieve absolute product authenticity.

When a native gene product is desired, a site-specific cleavage of the fusion protein must be performed. There are two principal ways to obtain specific cleavages of proteins: chemical and enzymatic. Examples of chemical cleavage agents include hydroxylamine, formic acid, acetic acid, cyanogen bromide, NBPS-skatole, o-iodosobenzoic acid, and N-chlorosuccinimide. Chemical agents can be used in the site-specific cleavage of fusion proteins as described in Carter, "Site-Specific Proteolysis of Fusion Proteins", in *Protein Purification: From Molecular Mechanisms to Large Scale Processes*, Ladisch et al., eds, American Chemical Society Symposium Series No. 427, Ch. 13, pp. 181–193 (1990). Alternatively, fusion tails can be removed by cleavage with enzymes, such as chymotrypsin, collagenase, endoprotease Lys-C, enterokinase, factor Xa, kallikrein, renin, H64A subtilisin BPN', thrombin, trypsin and ubiquitin protein peptidase as described in Carter, supra.

Enzymatic cleavages are more affected by steric factors than chemical methods. Accordingly, it is preferred that the cleavage site be carefully engineered to be structurally accessible to the enzyme. One strategy for enhancing the accessiblity to proteases is to flank the target sequence on both sides with short stretches of glycine residues or on one side if the correct terminus of the protein of interest is required after cleavage. An alternative strategy to enhance substrate accessibility is to perform the digests under denaturing or reducing conditions (provided that this is compatible with the protease used) or by denaturation of the substrate prior to digestion.

The invention encompasses fusion proteins in which the present Z domain variant peptides are fused to either the C-terminus or the N-terminus, or both terminii, of the desired protein. If removal of some or all of the affinity handle peptide sequence is desired, a protease-specific cleavage site can be engineered into the fusion protein at or near the fusion joint between the affinity handle peptide and the desired protein. In the case of a fusion protein with the affinity handle fused to the N-terminus of the desired protein (N-terminal fusion proteins), the affinity handle can advantageously comprise a Z domain variant peptide wherein the peptide either comprises a specific cleavage site or is attached at its C-terminus to a specific cleavage site such that the affinity handle sequence can be substantially removed from the desired protein by site-specific proteolytic cleavage. The cleavage site can be recognizable by either a chemical cleavage agent or an enzymatic cleavage agent, and is preferably not found in the amino acid sequence of the desired protein, i.e. cleavage with the agent does not result in fragmentation of the desired protein product. Enzymatic cleavage is well suited for production of an authentic N-terminus for the desired protein in the case of N-terminal fusion proteins because the major specificity determinants for enzyme endoproteases are associated with residues on the N-terminal side of the scissile bond, not the C-terminal side of the scissile bond. The non-specificity on the C-terminal side of the scissile bond permits the design of N-terminal fusion proteins in which the specific cleavage site directly abuts the N-terminal residue of the desired protein.

In the case of a fusion protein with the affinity handle fused to the C-terminus of the desired protein, the affinity handle can advantageously comprise a Z domain variant peptide wherein the peptide either comprises a specific cleavage site or is attached at its N-terminus to a specific cleavage site such that the affinity handle sequence can be substantially removed from the desired protein by site-specific proteolytic cleavage. The cleavage site can be recognizable by either a chemical cleavage agent or an enzymatic cleavage agent, and is preferably not found in the amino acid sequence of the desired protein, i.e. cleavage with the agent does not result in fragmentation of the desired protein product.

Fusion proteins containing the Z domain variant peptides of the invention can be conveniently produced by any of the methods described in Section B(II) above. Preferably, the fusion protein of interest is produced by synthesizing DNA encoding the fusion protein, constructing an expression vector in which the coding sequence is operably linked to control sequences recognized by a host cell, transforming the host cell with the recombinant expression vector, culturing the transformed host cell under conditions wherein the fusion protein is expressed, and recovering the expressed fusion protein as described in Section B(II) above. In the case of a host cell secretion system, the cell culture fluid can be harvested, filtered, loaded onto an IgG-ligand affinity chromatography column, and the bound fusion protein can be eluted from the column and collected using the same procedures as those employed for affinity purification of IgG with the Z domain variant-ligand affinity columns described in Section B(III) above. In one embodiment, an IgG Sepharose 6 Fast Flow (Pharmacia, Sweden) affinity column is used to purify the fusion protein according to the manufacturer's instructions. In the case of an intracellular expression system or a periplasmic space secretion system, the host cells are disrupted or lysed, the cell debris is preferably removed from the lysate, e.g. by centrifugation, and the crude extract is passed over an IgG affinity column and the fusion protein recovered as described above.

The desired protein may or may not be be properly folded when expressed as a fusion protein. Also, in embodiments employing a specific cleavage site allowing removal of the affinity handle from the desired protein, the specific cleavage site may or may not be accessible to the protease used for cleavage. These factors determine whether the fusion protein must be denatured and then refolded, and if so, whether these procedures are employed before or after cleavage. When denaturation and refolding are needed, typically the protein is treated with a chaotrope, such as a guanidine hydrochloride, and is then treated with a redox buffer, containing, for example, reduced and oxidized dithiothreitol or glutathione at the appropriate ratios, pH, and temperature, such that the protein of interest is refolded to its native conformation.

Likewise, in embodiments of the invention employing cyclized Z domain variant peptides as affinity handles for fusion proteins, the cyclization of the affinity handle peptide may require denaturation followed by gradual renaturation of the fusion protein recovered in the event that misfolding or inappropriate disulfide bond formation has occurred in the fusion protein product. As above, when denaturation and/or disulfide bond exchange is needed, the fusion protein is typically treated with a chaotrope, such as a guanidine hydrochloride, and is then treated with a redox buffer, containing, for example, reduced and oxidized dithiothreitol or glutathione at the appropriate ratios, pH, and temperature, such that the protein of interest is refolded to its native conformation and the desired cyclization of the affinity handle peptide occurs.

V. Therapeutic Uses of Z Domain Variant Peptides

Protein A most likely contributes to the pathogenicity of *Staphylococcus aureus* by its IgG binding activity (Patel et al., *Infect. Immun.*, 55: 3103 (1987)). Protein A molecules on the surface of staphylococcal pathogens can cause the host's IgG to coat the bacterium such that the effector functions of the immune system are incapable of recognizing foreign antigens on the bacterial cell surface and are incapable of interacting with the Fc regions of the IgG molecules coating the bacterium. Thus, the IgG-coated staphylococcus would be "invisible" to the host's immune defenses. The Z domain variant peptides of the invention can be used to strip IgG from the surface of staphylococcal pathogens by outcompeting the staphylococcal cell surface-bound protein A molecules for interaction with IgG. In this way, the Z domain variant peptides would unmask the foreign antigens on the bacterial cell surface for recognition by the host's immune system.

Accordingly, the invention provides for the treatment or prophylaxis of diseases mediated by staphylococcal pathogens, including staphylococcal furunculosis, impetigo, pyemia, osteomyelitis, suppuration of wounds, food poisoning, staphylococcemia, and any other staphylococcic infection, by administering an effective amount of the compounds of the invention to a patient in need of such treatment or prophylaxis. Also provided herein are compositions containing an effective amount of the compounds of the invention, including the nontoxic addition salts, amides and esters thereof, which may, alone, serve to provide the above-recited therapteutic or prophylactic benefits. Such compositions can be provided together with physiologically tolerable liquid, gel or solid diluents, adjuvants and excipients.

In addition, the Z domain variant peptides of the invention can also be used for the treatment or prophylaxis of other disease states that are induced or mediated by the Fc region of IgG (e.g. conditions such as rheumatoid arthritis).

The compounds and compositions can be adminstered to humans in a manner similar to other therapeutic agents. The dosage to be administered will depend on the usual factors, including the age, weight, sex, and condition of the patient and the route of administration,. In general, the dosage required for therapeutic efficacy will range from about 0.01 to 1000 $\mu$g/kg, more usually 0.1 to 25 $\mu$g/kg of the patient's body weight. Alternatively, dosages within these ranges can be administered by constant infusion over an extended period of time until the desired therapeutic benefits have been obtained.

Typically, such pharmaceutical compositions are prepared as injectable liquid solutions or suspensions. Compositions may also be emulsified. The active ingredient is often mixed with diluents or excipients which are physiologically tolerable and compatible with the active ingredient. Suitable diluents and excipients are, for example, water, saline, dextrose, glycerol, or the like, and combinations thereof. In addition, if desired the compositions may contain minor amounts of auxiliary substances such as wetting or emulsifying agents, stabilizing or pH-buffering agents, and the like. For a more detailed description of the foregoing see a standard pharmaceutical text such as *Remington's Pharmaceutical Sciences*, Mack Publishing Co. Easton, Pa. (1970).

The pharmaceutical compositions of this invention are conventionally administered parenterally by injection, either subcutaneously or intravenously. Additional formulations which are suitable for other modes of administration include suppositories, intranasal aerosols, and, in some cases, oral formulations. For suppositories, traditional binders and excipients may include, for example, polyalkylene glycols or triglycerides; such suppositories may be formed from mixtures containing the active ingredient in the range of 0.5% to 10% preferably 1%–2%. Oral formulations include such normally employed excipients as, for example, pharmaceutical grades of mannitol, lactose, starch, magnesium stearate, sodium saccharin, cellulose, magnesium carbonate, and the like. These compositions take the form of solutions, suspensions, tablets, pills, capsules, sustained-release formulations, or powders, and contain 10%–95% if active ingredient, preferably 25%–70%.

The peptide compounds of the invention may be formulated into the compositions as neutral or salt forms. Pharmaceutically acceptable nontoxic salts include the acid salts (formed with the free amino groups) and which are formed with inorganic acids such as, for example, hydrochloric or phosphoric acids, or organic acids such as acetic, oxalic, tartaric, mandelic, and the like. Salts formed with the free carboxyl groups may be derived from inorganic bases such as, for example, sodium, potassium, ammonium, calcium, or ferric hydroxides, and such organic bases as isopropyl amine, 2-ethylamino ethanol, histidine, procaine, and the like.

Therapy of staphylococcal diseases with the compositions of the invention can be combined with other known therapies for staphylococcias, such as treatment with penicillins, cephalosporins, polymyxins, nitroaromatics, aminoglycosides, tetracyclines, macrolides, lincomycins, and the like, or any other agents traditionally used for such infections.

Further details of the invention can be found in the following examples, which further define the scope of the invention. All references cited throughout the specification, and the references cited therein, are hereby expressly incorporated by reference in their entirety.

EXAMPLE 1

The B-domain of protein A, and a more stable variant called the Z-domain (Nilsson, B. et al., *Protein Engng.* 1: 107–113 (1987)), are three-helix, 59 residue modules that bind the $F_c$-portion of IgG's with a $K_d$ of about 10–50 nM (Cedergren, L. et al., *Protein Engng.* 6: 441–448 (1993)) X-ray (Deisenhofer, J., *Biochemistry* 20: 2361–2370 (1981)), NMR (Gouda, H. et al., *Biochemistry* 31: 9665–9672 (1992)) and mutational studies (Cedergren, L. et al., supra) show that binding contacts are presented from helix-1 (residues 7–18) and helix-2 (residues 20–38) (FIG. 1). Nonetheless, when helix-3is deleted the remaining peptide loses its $\alpha$-helical character and binding affinity is reduced >$10^5$-fold (Huston, J. S., et al., *Biophys. J.,* 62: 87–91 (1992)). It was determined herein that the two-helix motif can be stabilized and affinity optimized by improving three regions of the 38-residue peptide: the exposed hydrophobic region from helix-1 and helix-2 that contacts helix-3 (the Exoface, FIG. 2A), the buried residues between helix-1 and helix-2 (the Intraface, FIG. 2B), and the residues from the Z-domain predicted to contact the IgG (the Interface, FIG. 2C).

Phage display of protein or peptide libraries offers a powerful methodology for the selection of novel binding partners with improved affinity, altered specificity, or improved stability (Smith, G. P., *Curr. Opin. Biotechnol.* 2: 668–673 (1991)). High affinity proteins, displayed in a monovalent fashion as fusions with the M13 gene III coat protein (Clackson, T., et al., *Trends Biotechnol.* 12: 173–183 (1994)), can be identified by cloning and sequencing the corresponding DNA packaged in the phagemid particles after a number of rounds of binding selection.

A functional Z-domain of Protein A can be displayed on M13 phage particles (Nord, K., et al., *Protein Engng.* 8,: 609–614 (1995) and Djojonegoro, B. M. et al., *Biol/Technology.* 12: 169–172 (1994)) and this binds with an $EC_{50}$ of about 20 nM to IgG. Starting with a peptide representing the first two helices of the Z-domain, phagemid libraries were constructed to allow selection of variants at the Exoface, Intraface, and Interface regions. The libraries were selected sequentially and combined such that the best selectant from the Exoface library was used as a starting scaffold for the Intraface library, and the best selectant from that was incorporated into the starting scaffold for the Interface library. Through successive compilation of selected mutations, a peptide was engineered to bind to $IgG_1$ with nearly the same affinity as the wild type Z-domain at about half the size.

Materials and Methods

Construction of Libraries: Monovalent phagemid libraries (Lowman, H. B. et al., *Methods: Companion Methods Enzymol.* 3: 205–216 (1991)) of the truncated Z peptide were generated by site directed mutagenesis (Kunkel, T. A., et al., *Methods Enzmol.* 204: 125–139 (1991)). Each library contained four or five codons fully randomized for all 20 amino acids (as shown in Table 1 below). The starting template for libraries 2 and included a frame shift as well as a TAA stop codon to eliminate the background wild type clones. Stocks of approximately $10^{14}$ phagemid per ML were prepared from PEG precipitates of culture broths from XL-1 Blue cells containing the plasmid and superinfected with KO7 helper phage.

TABLE 1

Consensus residues from each truncated Z-domain library[a].

| WT residue | Selected residues | $P_e$ | $P_f$ | $(P_f-P_e)/\sigma$ |
|---|---|---|---|---|
| Exoface-1 Library[b] | | | | |
| I17 | I | 0.031 | 0.47 | 10.5 |
|  | A | 0.062 | 0.53 | 8.1 |
| L23 | D | 0.031 | 0.67 | 15.6 |
|  | N | 0.031 | 0.17 | 3.4 |
| L23 | L | 0.094 | 0.94 | 12.3 |
| F31 | K | 0.031 | 0.47 | 10.5 |
|  | F | 0.031 | 0.18 | 3.5 |
| Intraface-2 Library[c] | | | | |
| A13 | R | 0.094 | 0.85 | 11.6 |
| I17 | A | 0.062 | 1.0 | 17.4 |
| R28 | R | 0.094 | 1.0 | 13.9 |
| I32 | I | 0.031 | 1.0 | 24.8 |
| L35 | I | 0.031 | 0.90 | 22.3 |
| Interface-3A Library[d] | | | | |
| D3 | A | 0.062 | 0.40 | 4.4 |
|  | R | 0.094 | 0.40 | 3.3 |
| N4 | N | 0.031 | 0.50 | 8.7 |
|  | Q | 0.031 | 0.30 | 5.0 |

TABLE 1-continued

Consensus residues from each truncated Z-domain library[a].

| WT residue | Selected residues | $P_e$ | $P_f$ | $(P_f-P_e)/\sigma$ |
|---|---|---|---|---|
| K5 | G | 0.062 | 0.60 | 7.1 |
|  | S | 0.094 | 0.30 | 2.2 |
| F6 | F | 0.031 | 1.0 | 17.9 |
| Interface-3B Library | | | | |
| F6 | F | 0.031 | 0.60 | 10.5 |
|  | G | 0.062 | 0.40 | 4.4 |
| N7 | N | 0.031 | 0.40 | 6.8 |
|  | W | 0.031 | 0.40 | 6.8 |
| K8 | M | 0.031 | 0.90 | 16.1 |
| E9 | Q | 0.031 | 0.40 | 6.8 |
|  | K | 0.031 | 0.20 | 3.1 |
| Interface-3C Library | | | | |
| Q10 | Q | 0.031 | 1.0 | 17.9 |
| Q11 | Q | 0.031 | 1.0 | 17.9 |
| N12 | R | 0.094 | 0.70 | 6.6 |
|  | E | 0.031 | 0.20 | 3.1 |
| R13 | R | 0.094 | 0.60 | 5.5 |
|  | A | 0.062 | 0.30 | 3.1 |
| Interface-3D Library | | | | |
| F14 | F | 0.031 | 1.0 | 17.9 |
| Y15 | Y | 0.031 | 1.0 | 17.9 |
| L18 | L | 0.094 | 1.0 | 9.8 |
| H19 | H | 0.031 | 1.0 | 17.9 |
| Interface-3E Library | | | | |
| N29 | N | 0.031 | 1.0 | 17.9 |
| A30 | A | 0.062 | 1.0 | 12.3 |
| Q33 | K | 0.031 | 0.80 | 14.2 |
| K36 | R | 0.094 | 1.0 | 9.8 |

[a]The sequence of the original 38 residue peptide derived from the Z-domain was: AVDNKFNKEQQNAFYEILHLPNLNE-EQRNAFIQSLKDD (SEQ ID NO: 47). A single oligonucleotide was used to generate random mutations except for the Intraface-2 library which introduced two oligonucleotides simultaneously. Randomized codons were synthesized as NNS, where N represents any of the four bases and S represents an equal mix of G/C. This generates 32 possible codons encoding all 20 amino acids and theoretically produces $32^n$ possible DNA sequences. The number of transformants in each library greatly exceeded the theoretical value in all cases except the Intraface-2 library where $3.4 \times 10^7$ possible sequences exist but only $2 \times 10^6$ transformants were obtained. Phagemid libraries were constructed and sorted for binding to immobilized IgG according to the Materials and Methods and Table 1. After various rounds of binding selection, clones were sequenced and scored for the number of times themost commonly selected residues appeared at each of the mutated positions. $P_e$ = number of possible NNS codons/32 (for example, Ile is 1/32 and Arg is 3/32, etc.); $P_f$ = number of times residue found/number of clones sequenced; standard deviations $\sigma_n = [P_e(1-P_e)/n]^{1/2}$; n = number of clones sequenced; residues for which $[P_f-P_e)/\sigma_n] < 2.0$ are not shown.
[b]The Exoface-1 library was carried through four rounds of selection and eighteen clones were sequenced. Seven of the L23 codons found were non NNS codons, and thus were derived from the wild-type template; one clone was illegible at two positions.
[c]The Intraface-2 library was carried through ten rounds of selection and twenty clones were sequenced. Five clones were sequenced at round three, and ten at round six to monitor library diversity.
[d]The Interface-3A through 3E libraries were carried through ten rounds of selection and ten clones from each were sequenced. Five clones were sequenced from each library at round three, and ten clones from each at round six to monitor library diversity.

Selection and analysis of IgG specific phagemids: Microtiter plates (Nunc Maxisorb, 96 well) were coated with human IgG (Zymed) at a concentration of 10 μg per mL in 5 mM sodium carbonate pH 9.6 overnight at 4° C. Wells were blocked with a 1:1 mixture of 50 mM sodium carbonate (pH 9.6) and binding buffer (phosphate buffered saline (pH 7.2) PBS, with 0.1% BSA (Sigma, globulin free) and 0.05% Tween 20 (Sigma) for 1 hour. Approximately $10^{12}$ phage from the appropriate stock diluted to 100 μL with binding buffer were incubated for 2 hours before washing 20 times with PBS containing 0.05% Tween 20. Bound phage were eluted with 100 μL of 0.2 M glycine pH 2.0, neutralized with 1M Tris pH 9.0 and then used to infect *E. coli* (XL-1 Blue, Stratagene) for phagemid production. Phage ELISA were determined according to the method of Cunningham, B. C. et al., *EMBO J.*, 13: 2508–2515 (1994) against human IgG coated at 10 μg per mL in microtiter plates using an anti-M13-horseradish peroxidase conjugate (Pharmacia) with an o-phenylene diamine substrate (Sigma). Clones of interest were transformed into 27C7 cells (a non-suppressor strain of *E. coli*) (U.S. Pat. No. 5,288,931; ATCC No. 55,244) and 250 mL cultures were grown in low phosphate AP5 minimal media for 16 hours according to method of Chang, C. N., et al., *Gene* 55: 189–196 (1987). Both the supernatants and the periplasmic shockates were purified by affinity chromatography on IgG-Sepharose (Pharmacia). Final purification was accomplished by reverse phase HPLC. The mass of each peptide was confirmed by electrospray mass spectrometry and the peptides were determined to be >95% pure by HPLC. Peptide concentrations were determined by quantitative amino acid analysis.

Binding Kinetics and Circular Dichroism studies: Association and dissociation rate constants for the binding of both Z-domain and the selected peptides were determined by surface plasmon resonance. A monoclonal $IgG_1$ was immobilized on the biosensor chip covalently through the primary amines according to the method of Johnsson, B. E et al., *Anal. Biochem.* 198: 268–277 (1991). A coupling density of approximately 6000 RUs was used for both association and dissociation constant determinations. Association and dissociation rates shown in Table 2 below were measured at flow rates of 20 and 25 μL per minute respectively in PBS buffer (pH 7.4) with 0.05% Tween 20 as described by Karlsson, R. et al., *J. Immunol. Methods.* 145: 229–240 (1991).

CD spectra were recorded on an AVIV 60DS spectropolarimeter in the wavelength range of 250–190 nm in 0.2 nm intervals in a thermostated circular cuvette with a path length of 0.05 cm. The final CD spectra represent an average of 3 scans with an integration time of 2 seconds. Results are reported as mean residue ellipticity ($\Theta MRW$, in deg·cm$^2$·dmol$^{-1}$). Spectra were recorded at 8° C. with peptide concentrations of 0.20 mg/mL in 100 mM sodium chloride, 10 mM Tris-HCl at pH 7.2. Curve fitting was accomplished using the method of Provencher and Glockner in *Biochemistry*, 20: 33–37 (1981).

Results and Discussion

The Exoface Selectants: For the Exoface library, four residues from helix-1 and helix-2 (Ile17, Leu20, Leu23 and Phe31) that form a hydrophobic core with helix-3 in the intact Z-domain (FIG. 2A) were mutated. After four rounds of binding selection to IgG, a clear consensus was seen as shown in Table 1 above. The wild-type residues, Leu20 and Phe31, were replaced by the charged residues Asp and Lys, respectively (FIG. 2A). At the other two positions the wild-type residues, Ile17 and Leu23, were predominantly retained, possibly because they stabilize the hydrophobic intraface between helix-1 and helix-2 or the type 1 β-turn that connects them. The consensus Exoface-1 selectant (L20D/F31K) exhibited an $EC_{50}$ by phage ELISA of 3.4 μM for binding to IgG as shown in Table 2 below. The truncated Z-domain peptide (residues 1–38) did not show any detectable binding by phage ELISA although a $K_d$ in the millimolar range has been reported for an analogous peptide (Huston, J. S., et al., supra).

TABLE 2

Phage ELISA and binding kinetics for representative selectants and consensus peptides.

| Protein | $k_{on}$ (×10$^5$M$^{-1}$ s$^{-1}$) | $k_{off}$ (s$^{-1}$) | $K_d$ (nM) | $EC_{50}$ (nM) |
|---|---|---|---|---|
| 3-helix Z domain | 2.09 | 0.0021 | 10 | 20 |
| 2-helix Z-domain | ND | ND | >1 × 10$^4$ | >1 × 10$^4$ |
| Exoface-1 variant: | | | | |
| A = L20D/F31K | ND | ND | ND | 3400 |
| Exoface-1 plus Intraface-2 variants: | | | | |
| B = A + I17A/L35A | ND | ND | ND | 930 |
| C = A + A13R/I17A/L35I | 1.78 | 0.133 | 750 | 420 |
| Exoface-1 plus Intraface-2 plus Interface-3 variants: | | | | |
| D = C + D3R/K5G | 2.06 | 0.091 | 440 | 230 |
| E = C + D3A/N4Q/K5S | 1.61 | 0.091 | 570 | 140 |
| F = C + K8M/E9Q | 1.48 | 0.135 | 910 | 300 |
| G = C + F6G/N7W/K8M/E9R | 2.97 | 0.099 | 333 | 150 |
| H = C + N12R | 3.08 | 0.094 | 310 | 180 |
| I = C + N12R/R13A | 1.97 | 0.125 | 630 | 260 |
| J = C + Q33K/K36R | 2.00 | 0.073 | 370 | 140 |
| Exoface-1 plus Intraface-2 plus combined Interface-3 variants: | | | | |
| K = D + F + H + J | 5.04 | 0.030 | 60 | 180 |
| L = E + F + H + J | 4.87 | 0.030 | 62 | 60 |
| M = F6–D38 of L | 4.60 | 0.020 | 43 | ND |

Kinetic measurements were determined on a BIAcore where a monoclonal $IgG_1$ was immobilized on the biosensor chip. The $k_{on}$ values were determined by measuring $k_s$ at 5 different concentrations, 4 μM, 3 μM, 2 μM, 1 μM, and 0.5 μM, and then plotting the $K_s$ values as a function of concentration. Standard error values were less than 2.5%. The $k_{off}$ values were measured in duplicate with saturating injections at a concentration of 25 μM. Reported values areaveraged, standard errors were less than 3.5%. The $K_d$ values are calculated from $k_{off}/k_{on}$. Variant M is a synthetic peptide prepared by standard solid phase synthesis using N-fluorenyl-methoxycarbonyl protocols.

The Intraface Selectants: Beginning with the consensus Exoface-1 peptide as a template, the Interface library was generated by mutating the hydrophobic core between helix-1 and helix-2 (Ala13, Ile17, Arg28, Ile32, and Leu35; FIG. 2B). Three of the five residues converged to a non-wild-type solution (A13R, I17A, and L35I) as shown in Table 1 above. These three residues form a cluster and apparently repack the core at the open end of the two helices (FIG. 2B). Positions 13 and 17 are next to each other on helix-1; the Ala/Ile wild-type combination is replaced by an Arg/Ala pair. Phage ELISA (Table 2 above) indicated that the consensus sequence of A13R/I17A/L35I possessed an $EC_{50}$ that is about 10-fold greater than that of consensus Exoface-1 variant.

The Interface Selectants: Beginning with the improved Exoface/Intraface selectants a template, five Interface libraries were generated by mutating nineteen residues, in groups of four, at or near the interface between the Z-domain and the $F_c$ portion of IgG (FIG. 2C). For the Interface-3A library, a weak consensus was found where Asn4 and Phe6 were largely conserved as shown in Table 1 above.

The Interface-3B library generated two different consensus sequences as shown in Table 1 above; one conserved Phe6 and Asn7 while the other mutated these residues to Gly6 and Trp7. The aliphatic portion of Lys8 in the wild-type sits at the helical intraface and does not make direct contact with the IgG; this position showed a strong consensus for Met. Concomitant with the K8M change, the negatively charged Glu9 was neutralized to Gln or inverted to Lys (FIG. 2C).

From the Interface-3C library, it was determined that the contact residues Gln10 and Gln11 were completely conserved. Asn12 was frequently converted to a charged residue (Arg or Glu), while Arg13 was mostly conserved. The four residues in the Interface-3D library (R14, Y15, L18, H19) were completely conserved, indicating that these residues cannot be improved upon with natural amino acids. In the Interface-3E library, two new consensus residues were determined in which Gln33 was replaced by Lys, and Lys36 was replaced by Arg (FIG. 2F). Phage ELISA's for the consensus selectants from each of these libraries (Table 2 above) showed improvements in affinity ranging from two to three-fold over the starting Exoface/Intraface variant.

Improvements in binding kinetics and affinities for the most preferred peptides: The binding kinetics and affinities for each of the purified consensus peptides were determined with respect to a monoclonal $IgG_1$ by surface plasmon resonance as shown in Table 2 above. The starting 38-residue peptide did not show any detectable binding at concentrations up to 25 µM. The binding affinity of the combined Exoface/Intraface selectant (Table 2, variant C) represents an approximately 1000-fold improvement over the starting 38 residue peptide. Variant C had a $k_{on}$ that was equivalent to the full-length Z-domain, but a $k_{off}$ that was approximately 100-fold greater.

The peptides derived from the Interface-3 libraries showed slight improvements in $k_{on}$ and/or $k_{off}$, as shown in the data for variants D through J in Table 2 above. Overall, each of these peptides showed a two to three-fold improvement in affinity over variant C based on a comparison of relative $K_d$ values. To further improve affinity, the consensus variants from the Interface libraries (variants K and L, in Table 2 above) were combined. The resulting peptides showed two fold-improvements in $k_{on}$ and five-fold improvements in $k_{off}$ relative to most of the selectants in any of the Interface-3 libraries. The affinities for these mutants are only 6-fold weaker than the full-length Z-domain and represent an improvement of greater than $10^4$-fold over the starting 38-residue peptide. These final derivatives associate about 2.5-times faster than the full-length Z-domain and dissociate only about 14-fold faster, indicating that the activity of the binding determinants on the analog is approaching that of the full length Z-domain. A synthetic peptide derived from variant L but with the N-terminal five residues deleted (Phe6-Asp38, variant M) actually has a slower $k_{off}$ than variant L and thus a $K_d$ value only four-fold higher than the full-length Z-domain as shown in Table 2 above. Surprisingly, this peptide has only about 50% of the size (33 residues) of the original 59 residue Z-domain.

Evolving binding affinity in the two-helix derivative increases the α-helical structure: The secondary structural characteristics of some of these peptides after various stages of affinity optimization were evaluated by CD spectroscopy (FIG. 2). The starting 38-residue peptide showed only 11% helical content. However, the helical content progressively increased in going from this to the Exoface/Intraface most preferred variant (50%), and then to the final combined Interface mutant (56%). This compares with a maximum helical content of 63% estimated from the number of residues in a helical conformation as determined from the x-ray coordinates (Deisenhofer, J., supra) of the two-helix segment present in the intact B-domain.

Additional evidence suggests that the evolved two-helix bundle is highly structured. First, the $k_{on}$ values are comparable to or greater than the full-length Z-domain, indicating that little reorganization is necessary. Many of the residues that are selected in either the Exoface, Intraface, or Interface libraries are buried in the two-helix bundle model (FIG. 2). It is likely that these residues were selected because they stabilize the core of the two-helix structure. Many of the residues that were absolutely conserved in the Interface libraries are highly buried in the complex with the IgG, indicating that determinants from the two-helix motif are the same ones used in the full-length Z-domain. This was confirmed by alanine-scanning mutagenesis of the two-helix variant L which shows that these conserved residues are critical for binding. Lastly, binding from a discontinuous epitope usually depends on precise display of determinants and therefore requires a highly ordered structure. Preliminary results from the structural characterization of a two helix variant by NMR confirm that this peptide adopts essentially the same conformation as helix-1 and helix-2 in the x-ray structure (Deisenhofer, J., supra).

Additionally, the alanine-scanning mutagenesis data for the variant L peptide indicated that an Arg12Ala substitution improved the IgG-binding affinity of the peptide.

EXAMPLE 2

Materials and Methods

A disulfide-linked 2 helix variant of the Z-domain was designed by incorporating a cysteine residue at the C-terminus and replacing glutamine 10 with cysteine in the peptide sequence of variant M in Example 1 above. A disulfide bond can be formed to covalently link the N and C terminus. The design was modeled in the context of both the 2-helix peptides of Example 1 above and the full length Z-domain.

The designed peptide, sequence FNMQCQRRFYEALH-DPNLNEEQRNAKIKSIRDDC (SEQ ID NO:36), was synthesized using standard N-fluorenyl-methoxycarbonyl protocols on a solid support according to the method of Fields and Noble, *Int. J. Peptide Protein Res.*, 35: 161–214 (1990). The peptide was synthesized and cleaved with the cysteine thiols in the reduced form. Oxidation to form the disulfide linkage was performed by raising the pH of a cold (40° C.) aqueous solution of the peptide to 8.5 with ammonium hydroxide, followed by the addition of a dilute aqueous solution of potassium ferricyanide until a persistant pale yellow color was obtained. Alternatively, the cyclization of the peptide can be performed at a somewhat slower rate under the same conditions in the absence of potassium ferricyanide.

RESULTS AND DISCUSSION

The thermal stability of the disulfide linked peptide was assessed by circular dichroism, monitoring $\Theta_{222}$ as a measure of α-helicity. It was determined that the disulfide linkage contributes significantly to the stability of the peptide structure, and that the peptide retained its helical conformation even at 75° C. This conformational stability is comparable to that of the native 3-helix Z-domain. Additional evidence of the enhanced structure of the disulfide linked peptide was obtained by NMR characterization.

The affinity of the disulfide linked peptide for IgG was determined by surface plasmon resonance. The cyclized peptide was found to possess a very fast $k_{on}$ rate of reaction for forming a complex with IgG ($1.2 \times 10^6$ sec$^{-1}$), approximately 6 fold faster than the native 3-helix Z-domain and about 2.5 fold faster than the nonlinked 2-helix peptide (variant M in Example 1 above). This increased $k_{on}$ indicates that the disulfide linked peptide is better organized for binding IgG. The rate of reaction for dissociation of the disulfide linked peptide/IgG complex ($k_{off}$) was determined to be about 30% slower than the nonlinked 2-helix peptide (variant M) but still 7 fold faster than the native Z-domain. Overall, the enhanced binding kinetics of the disulfide linked peptide yield a dissocation constant ($K_d$) of 11 nM. This value compares quite favorably with the $K_d$ of 10 nM for the native Z-domain. While the kinetics of IgG binding differ between the disulfide linked peptide and the wild type Z domain, the net $K_d$ is essentially the same.

We claim:

1. A compound represented by Formula (II):

(II)
(SEQ ID NO:3)

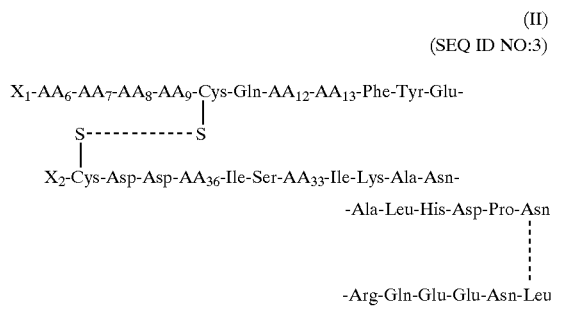

$X_1$-$AA_6$-$AA_7$-$AA_8$-$AA_9$-Cys-Gln-$AA_{12}$-$AA_{13}$-Phe-Tyr-Glu-
                              |
        S-----------S
        |
$X_2$-Cys-Asp-Asp-$AA_{36}$-Ile-Ser-$AA_{33}$-Ile-Lys-Ala-Asn-

-Ala-Leu-His-Asp-Pro-Asn

-Arg-Gln-Glu-Glu-Asn-Leu where $X_1$ is selected from the group consisting of H, $C_1$–$C_6$alkanoyl, and Z-Ala-Val-$AA_3$-$AA_4$-$AA_5$ (SEQ ID NO:2);

where

Z is selected from the group consisting of H and $C_1$–$C_6$alkanoyl;

$AA_3$ is selected from the group consisting of Asp, Arg, and Ala;

$AA_4$ is selected from the group consisting of Asn and Gln; and $AA_5$ is selected from the group consisting of Lys, Gly, and Ser;

$AA_6$ is selected from the group consisting of Phe and Gly;

$AA_7$ is selected from the group consisting of Asn and Trp;

$AA_8$ is selected from the group consisting of Lys and Met;

$AA_9$ is selected from the group consisting of Glu, Gln, and Arg;

$AA_{12}$ is selected from the group consisting of Asn, Ala, and Arg;

$AA_{13}$ is selected from the group consisting of Ala and Arg;

$AA_{33}$ is selected from the group consisting of Gln and Lys;

$AA_{36}$ is selected from the group consisting of Lys and Arg; and $X_2$ is selected from the group consisting of $OR_1$ and $NR_1R_2$ where $R_1$ and $R_2$ are independently selected from the group consisting of H, $C_1$–$C_6$alkyl, $C_6$–$C_{12}$aryl and $C_6$–$C_{12}$aryl-$C_1$–$C_6$alkyl;

which compound is covalently linked to a macromolecule to form a conjugate.

2. The conjugate of claim 1 wherein the macromolecule is a solid support.

3. The conjugate of claim 1 wherein the compound is selected from the group consisting of:

(SEQ ID NO:26)
```
        Phe-Lys-Asn-Asp-Val-Ala-Z
        |
        Asn-Lys-Glu-Cys-Gln-Asn-Arg-Phe-Tyr-Glu-Ala-Leu-His-Asp-Pro-Asn
                      |
        S-----------S
        |
X₂-Cys-Asp-Asp-Lys-Ile-Ser-Gln-Ile-Lys-Ala-Asn-Arg-Gln-Glu-Glu-Asn-Leu;
```

(SEQ ID NO:27)
```
        Phe-Gly-Asn-Arg-Val-Ala-Z
        |
        Asn-Lys-Glu-Cys-Gln-Asn-Arg-Phe-Tyr-Glu-Ala-Leu-His-Asp-Pro-Asn
                      |
        S-----------S
        |
X₂-Cys-Asp-Asp-Lys-Ile-Ser-Gln-Ile-Lys-Ala-Asn-Arg-Gln-Glu-Glu-Asn-Leu;
```

(SEQ ID NO:28)
```
        Phe-Ser-Gln-Ala-Val-Ala-Z
        |
        Asn-Lys-Glu-Cys-Gln-Asn-Arg-Phe-Tyr-Glu-Ala-Leu-His-Asp-Pro-Asn
                      |
        S-----------S
        |
X₂-Cys-Asp-Asp-Lys-Ile-Ser-Gln-Ile-Lys-Ala-Asn-Arg-Gln-Glu-Glu-Asn-Leu;
```

(SEQ ID NO:29)
```
        Phe-Lys-Asn-Asp-Val-Ala-Z
        |
        Asn-Met-Gln-Cys-Gln-Asn-Arg-Phe-Tyr-Glu-Ala-Leu-His-Asp-Pro-Asn
                      |
        S-----------S
        |
X₂-Cys-Asp-Asp-Lys-Ile-Ser-Gln-Ile-Lys-Ala-Asn-Arg-Gln-Glu-Glu-Asn-Leu;
```

(SEQ ID NO:30)
```
        Gly-Lys-Asn-Asp-Val-Ala-Z
        |
        Trp-Met-Arg-Cys-Gln-Asn-Arg-Phe-Tyr-Glu-Ala-Leu-His-Asp-Pro-Asn
                      |
        S-----------S
        |
X₂-Cys-Asp-Asp-Lys-Ile-Ser-Gln-Ile-Lys-Ala-Asn-Arg-Gln-Glu-Glu-Asn-Leu;
```

(SEQ ID NO:31)
```
        Phe-Lys-Asn-Asp-Val-Ala-Z
        |
        Asn-Lys-Glu-Cys-Gln-Arg-Arg-Phe-Tyr-Glu-Ala-Leu-His-Asp-Pro-Asn
                      |
        S-----------S
        |
X₂-Cys-Asp-Asp-Lys-Ile-Ser-Gln-Ile-Lys-Ala-Asn-Arg-Gln-Glu-Glu-Asn-Leu;
```

(SEQ ID NO:32)
```
        Phe-Lys-Asn-Asp-Val-Ala-Z
        |
        Asn-Lys-Glu-Cys-Gln-Arg-Ala-Phe-Tyr-Glu-Ala-Leu-His-Asp-Pro-Asn
                      |
        S-----------S
        |
X₂-Cys-Asp-Asp-Lys-Ile-Ser-Gln-Ile-Lys-Ala-Asn-Arg-Gln-Glu-Glu-Asn-Leu;
```

(SEQ ID NO:33)
```
        Phe-Lys-Asn-Asp-Val-Ala-Z
        |
        Asn-Lys-Glu-Cys-Gln-Asn-Arg-Phe-Tyr-Glu-Ala-Leu-His-Asp-Pro-Asn
                      |
        S-----------S
        |
X₂-Cys-Asp-Asp-Arg-Ile-Ser-Lys-Ile-Lys-Ala-Asn-Arg-Gln-Glu-Glu-Asn-Leu;
```

(SEQ ID NO:34)
```
        Phe-Gly-Asn-Arg-Val-Ala-Z
        |
        Asn-Met-Gln-Cys-Gln-Arg-Arg-Phe-Tyr-Glu-Ala-Leu-His-Asp-Pro-Asn
                      |
        S-----------S
        |
X₂-Cys-Asp-Asp-Arg-Ile-Ser-Lys-Ile-Lys-Ala-Asn-Arg-Gln-Glu-Glu-Asn-Leu;
```

-continued (SEQ ID NO:35)
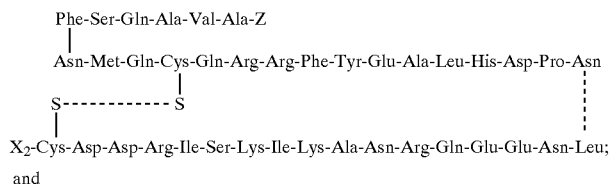
and (SEQ ID NO:36)
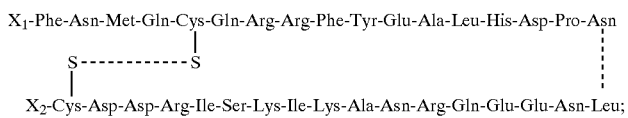

where $X_1$ is selected from the group consisting of H and $C_1$–$C_6$alkanoyl;

Z is selected from the group consisting of H and $C_1$–$C_6$alkanoyl; and $X_2$ is selected from the group consisting of $OR_1$ and $NR_1R_2$ where $R_1$ and $R_2$ are independently selected from the group consisting of H, $C_1$–$C_6$alkyl, $C_6$–$C_{12}$aryl and $C_6$–$C_{12}$aryl-$C_1$–$C_6$alkyl.

4. The conjugate of claim 1 wherein the compound is selected from the group consisting of:

(SEQ ID NO:37)
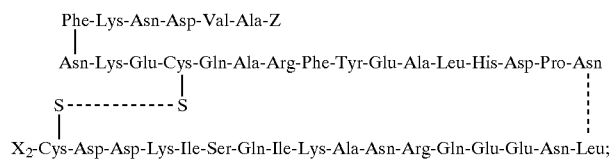

(SEQ ID NO:38)
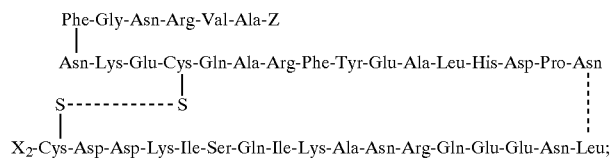

(SEQ ID NO:39)
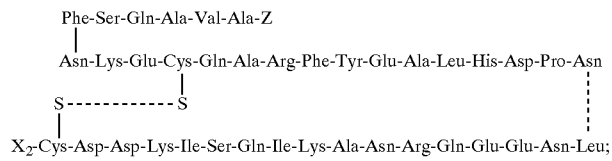

(SEQ ID NO:40)
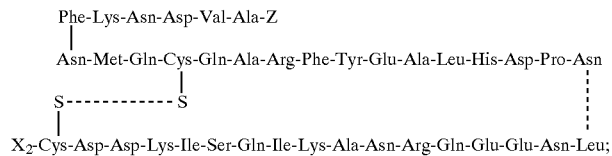

(SEQ ID NO:41)
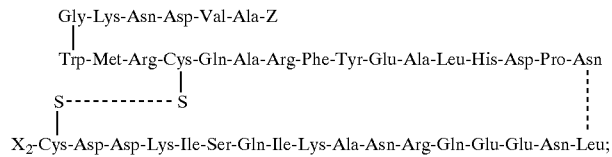

-continued (SEQ ID NO:42)
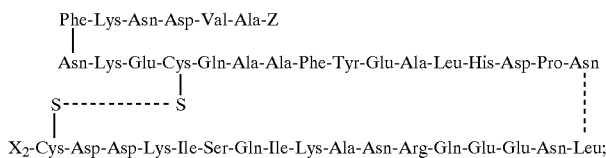

(SEQ ID NO:43)
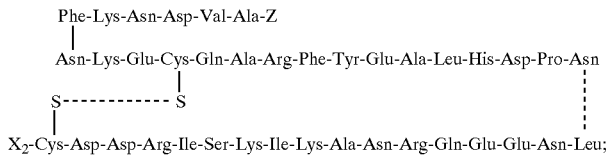

(SEQ ID NO:44)
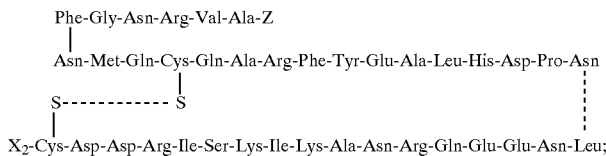

(SEQ ID NO:45)
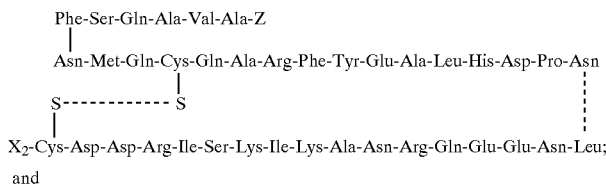
and (SEQ ID NO:46)
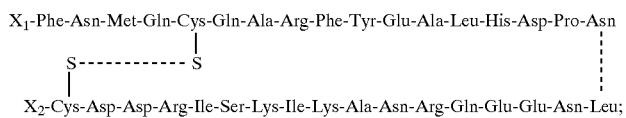

where
- $X_1$ is selected from the group consisting of H and $C_1$–$C_6$alkanoyl;
- Z is selected from the group consisting of H and $C_1$–$C_6$alkanoyl; and
- $X_2$ is selected from the group consisting of $OR_1$ and $NR_1R_2$ where $R_1$ and $R_2$ are independently selected from the group consisting of H, $C_1$–$C_6$alkyl, $C_6$–$C_{12}$aryl and $C_6$–$C_{12}$aryl-$C_1$–$C_6$alkyl.

5. A compound represented by Formula (II):

(II)
(SEQ ID NO:3)

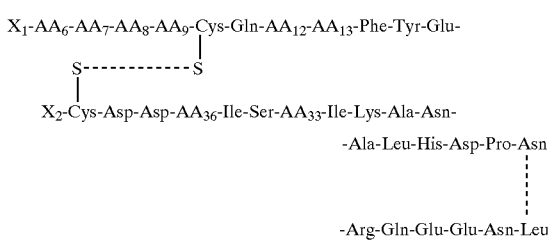

where
- $X_1$ is selected from the group consisting of H, $C_1$–$C_6$alkanoyl, and Z-Ala-Val-$AA_3$-$AA_4$-$AA_5$ (SEQ ID NO:2);

where
- Z is selected from the group consisting of H and $C_1$–$C_6$alkanoyl;
- $AA_3$ is selected from the group consisting of Asp, Arg, and Ala;
- $AA_4$ is selected from the group consisting of Asn and Gln; and
- $AA_5$ is selected from the group consisting of Lys, Gly, and Ser;
- $AA_6$ is selected from the group consisting of Phe and Gly;
- $AA_7$ is selected from the group consisting of Asn and Trp;
- $AA_8$ is selected from the group consisting of Lys and Met;
- $AA_9$ is selected from the group consisting of Glu, Gln, and Arg;
- $AA_{12}$ is selected from the group consisting of Asn, Ala, and Arg;
- $AA_{13}$ is selected from the group consisting of Ala and Arg;
- $AA_{33}$ is selected from the group consisting of Gln and Lys;
- $AA_{36}$ is selected from the group consisting of Lys and Arg; and
- $X_2$ is selected from the group consisting of $OR_1$ and $NR_1R_2$ where $R_1$ and $R_2$ are independently selected from the group consisting of H, $C_1$–$C_6$alkyl, $C_6$–$C_{12}$aryl and $C_6$–$C_{12}$aryl-$C_1$–$C_6$alkyl;

which compound is fused to a selected polypeptide to form a fusion protein.

6. The fusion protein of claim 5 wherein the compound of Formula (II) is specifically cleavable from the amino acid sequence of the selected polypeptide.

7. The fusion protein of claim 5 wherein the compound is selected from the group consisting of:

(SEQ ID NO:26)
```
          Phe-Lys-Asn-Asp-Val-Ala-Z
           |
          Asn-Lys-Glu-Cys-Gln-Asn-Arg-Phe-Tyr-Glu-Ala-Leu-His-Asp-Pro-Asn
                       |                                              
     S-----------S                                                    
     |                                                                
X₂-Cys-Asp-Asp-Lys-Ile-Ser-Gln-Ile-Lys-Ala-Asn-Arg-Gln-Glu-Glu-Asn-Leu;
```

(SEQ ID NO:27)
```
          Phe-Gly-Asn-Arg-Val-Ala-Z
           |
          Asn-Lys-Glu-Cys-Gln-Asn-Arg-Phe-Tyr-Glu-Ala-Leu-His-Asp-Pro-Asn
                       |
     S-----------S
     |
X₂-Cys-Asp-Asp-Lys-Ile-Ser-Gln-Ile-Lys-Ala-Asn-Arg-Gln-Glu-Glu-Asn-Leu;
```

(SEQ ID NO:28)
```
          Phe-Ser-Gln-Ala-Val-Ala-Z
           |
          Asn-Lys-Glu-Cys-Gln-Asn-Arg-Phe-Tyr-Glu-Ala-Leu-His-Asp-Pro-Asn
                       |
     S-----------S
     |
X₂-Cys-Asp-Asp-Lys-Ile-Ser-Gln-Ile-Lys-Ala-Asn-Arg-Gln-Glu-Glu-Asn-Leu;
```

(SEQ ID NO:29)
```
          Phe-Lys-Asn-Asp-Val-Ala-Z
           |
          Asn-Met-Gln-Cys-Gln-Asn-Arg-Phe-Tyr-Glu-Ala-Leu-His-Asp-Pro-Asn
                       |
     S-----------S
     |
X₂-Cys-Asp-Asp-Lys-Ile-Ser-Gln-Ile-Lys-Ala-Asn-Arg-Gln-Glu-Glu-Asn-Leu;
```

(SEQ ID NO:30)
```
          Gly-Lys-Asn-Asp-Val-Ala-Z
           |
          Trp-Met-Arg-Cys-Gln-Asn-Arg-Phe-Tyr-Glu-Ala-Leu-His-Asp-Pro-Asn
                       |
     S-----------S
     |
X₂-Cys-Asp-Asp-Lys-Ile-Ser-Gln-Ile-Lys-Ala-Asn-Arg-Gln-Glu-Glu-Asn-Leu;
```

(SEQ ID NO:31)
```
          Phe-Lys-Asn-Asp-Val-Ala-Z
           |
          Asn-Lys-Glu-Cys-Gln-Arg-Ala-Phe-Tyr-Glu-Ala-Leu-His-Asp-Pro-Asn
                       |
     S-----------S
     |
X₂-Cys-Asp-Asp-Lys-Ile-Ser-Gln-Ile-Lys-Ala-Asn-Arg-Gln-Glu-Glu-Asn-Leu;
```

(SEQ ID NO:32)
```
          Phe-Lys-Asn-Asp-Val-Ala-Z
           |
          Asn-Lys-Glu-Cys-Gln-Asn-Arg-Phe-Tyr-Glu-Ala-Leu-His-Asp-Pro-Asn
                       |
     S----------- S
     |
X₂-Cys-Asp-Asp-Lys-Ile-Ser-Gln-Ile-Lys-Ala-Asn-Arg-Gln-Glu-Glu-Asn-Leu;
```

(SEQ ID NO:33)
```
          Phe-Lys-Asn-Asp-Val-Ala-Z
           |
          Asn-Lys-Glu-Cys-Gln-Asn-Arg-Phe-Tyr-Glu-Ala-Leu-His-Asp-Pro-Asn
                       |
     S-----------S
     |
X₂-Cys-Asp-Asp-Arg-Ile-Ser-Lys-Ile-Lys-Ala-Asn-Arg-Gln-Glu-Glu-Asn-Leu;
```

-continued (SEQ ID NO:34)
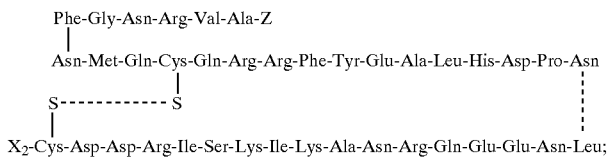

(SEQ ID NO:35)
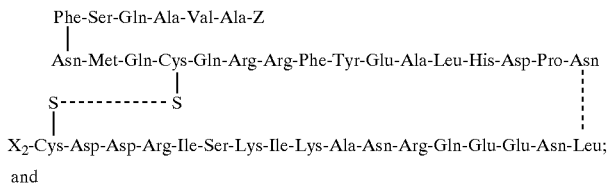
and (SEQ ID NO:36)
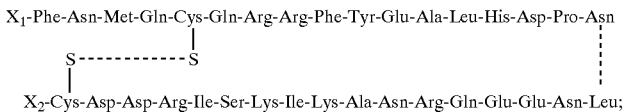

where $X_1$ is selected from the group consisting of H and $C_1$–$C_6$alkanoyl;

Z is selected from the group consisting of H and $C_1$–$C_6$alkanoyl; and $X_2$ is selected from the group consisting of $OR_1$ and $NR_1R_2$ where $R_1$ and $R_2$ are independently selected from the group consisting of H, $C_1$–$C_6$alkyl, $C_6$–$C_{12}$aryl and $C_6$–$C_{12}$aryl-$C_1$–$C_6$alkyl.

8. The fusion protein of claim 5 wherein the compound is selected from the group consisting of:

(SEQ ID NO:37)
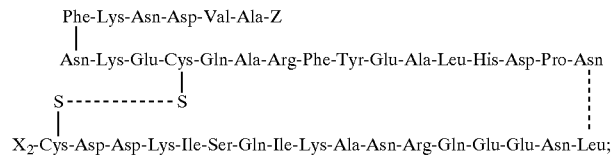

(SEQ ID NO:38)
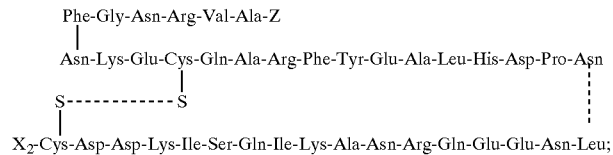

(SEQ ID NO:39)
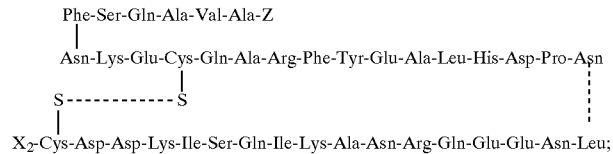

(SEQ ID NO:40)
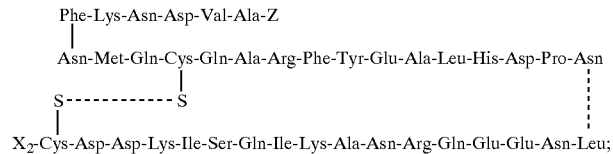

(SEQ ID NO:41)
```
      Gly-Lys-Asn-Asp-Val-Ala-Z
       |
      Trp-Met-Arg-Cys-Gln-Ala-Arg-Phe-Tyr-Glu-Ala-Leu-His-Asp-Pro-Asn
   S------------S                    |
   |                                 :
X₂-Cys-Asp-Asp-Lys-Ile-Ser-Gln-Ile-Lys-Ala-Asn-Arg-Gln-Glu-Glu-Asn-Leu;
```

(SEQ ID NO:42)
```
      Phe-Lys-Asn-Asp-Val-Ala-Z
       |
      Asn-Lys-Glu-Cys-Gln-Ala-Ala-Phe-Tyr-Glu-Ala-Leu-His-Asp-Pro-Asn
   S------------S                    |
   |                                 :
X₂-Cys-Asp-Asp-Lys-Ile-Ser-Gln-Ile-Lys-Ala-Asn-Arg-Gln-Glu-Glu-Asn-Leu;
```

(SEQ ID NO:43)
```
      Phe-Lys-Asn-Asp-Val-Ala-Z
       |
      Asn-Lys-Glu-Cys-Gln-Ala-Arg-Phe-Tyr-Glu-Ala-Leu-His-Asp-Pro-Asn
   S------------S                    |
   |                                 :
X₂-Cys-Asp-Asp-Arg-Ile-Ser-Lys-Ile-Lys-Ala-Asn-Arg-Gln-Glu-Glu-Asn-Leu;
```

(SEQ ID NO:44)
```
      Phe-Gly-Asn-Arg-Val-Ala-Z
       |
      Asn-Met-Gln-Cys-Gln-Ala-Arg-Phe-Tyr-Glu-Ala-Leu-His-Asp-Pro-Asn
   S------------S                    |
   |                                 :
X₂-Cys-Asp-Asp-Arg-Ile-Ser-Lys-Ile-Lys-Ala-Asn-Arg-Gln-Glu-Glu-Asn-Leu;
```

(SEQ ID NO:45)
```
      Phe-Ser-Gln-Ala-Val-Ala-Z
       |
      Asn-Met-Gln-Cys-Gln-Ala-Arg-Phe-Tyr-Glu-Ala-Leu-His-Asp-Pro-Asn
   S------------S                    |
   |                                 :
X₂-Cys-Asp-Asp-Arg-Ile-Ser-Lys-Ile-Lys-Ala-Asn-Arg-Gln-Glu-Glu-Asn-Leu;
```
and (SEQ ID NO:46)
```
X₁-Phe-Asn-Met-Gln-Cys-Gln-Ala-Arg-Phe-Tyr-Glu-Ala-Leu-His-Asp-Pro-Asn
   S------------S                    |
   |                                 :
X₂-Cys-Asp-Asp-Arg-Ile-Ser-Lys-Ile-Lys-Ala-Asn-Arg-Gln-Glu-Glu-Asn-Leu;
``` where $X_1$ is selected from the group consisting of H and $C_1$–$C_6$alkanoyl;

Z is selected from the group consisting of H and $C_1$–$C_6$alkanoyl; and $X_2$ is selected from the group consisting of $OR_1$ and $NR_1R_2$ where $R_1$ and $R_2$ are independently selected from the group consisting of H, $C_1$–$C_6$alkyl, $C_6$–$C_{12}$aryl and $C_6$–$C_{12}$aryl-$C_1$–$C_6$alkyl.

* * * * *